US009511342B2

(12) United States Patent
Meng et al.

(10) Patent No.: US 9,511,342 B2
(45) Date of Patent: Dec. 6, 2016

(54) ANTIBODY PREPARATION METHOD, AND ANTIBODY AND ANTIBODY LIBRARY THUS PREPARED

(75) Inventors: Xun Meng, Shanghai (CN); Xiaoqing Wang, Shanghai (CN); Zeyong Chen, Shanghai (CN); Guoxing Wang, Shanghai (CN)

(73) Assignee: ABMART (SHANGHAI) CO., LTD., Shanghai (CN)

( * ) Notice: Subject to any disclaimer, the term of this patent is extended or adjusted under 35 U.S.C. 154(b) by 512 days.

(21) Appl. No.: 13/982,820

(22) PCT Filed: Jan. 30, 2012

(86) PCT No.: PCT/CN2012/070768
§ 371 (c)(1),
(2), (4) Date: Jul. 31, 2013

(87) PCT Pub. No.: WO2012/103797
PCT Pub. Date: Aug. 9, 2012

(65) Prior Publication Data
US 2013/0310274 A1 Nov. 21, 2013

(30) Foreign Application Priority Data
Jan. 31, 2011 (CN) .......................... 2011 1 0034648

(51) Int. Cl.
| C40B 50/06 | (2006.01) |
| B01J 19/00 | (2006.01) |
| C07K 16/00 | (2006.01) |
| C07K 16/18 | (2006.01) |
| C07K 16/28 | (2006.01) |
| C07K 16/40 | (2006.01) |

(52) U.S. Cl.
CPC ............ *B01J 19/0046* (2013.01); *C07K 16/00* (2013.01); *C07K 16/18* (2013.01); *C07K 16/28* (2013.01); *C07K 16/40* (2013.01); *C40B 50/06* (2013.01)

(58) Field of Classification Search
None
See application file for complete search history.

(56) References Cited

U.S. PATENT DOCUMENTS

2003/0060409 A1 3/2003 Ramanathan et al.
2003/0224493 A1 12/2003 Eirich et al.

FOREIGN PATENT DOCUMENTS

| CN | 101012280 A | 8/2007 |
| WO | 01/12781 A1 | 2/2001 |
| WO | 2010/008587 A2 | 1/2010 |
| WO | 2010/124113 A1 | 10/2010 |

OTHER PUBLICATIONS

Barbas et al. (Sep. 15, 1991) Proceedings of the National Academy of Sciences USA vol. 88 pp. 7978 to 7982.*

(Continued)

*Primary Examiner* — Christian Boesen
(74) *Attorney, Agent, or Firm* — Rothwell, Figg, Ernst & Manbeck, p.c.

(57) ABSTRACT

Provided is a method for preparing antibodies against a protein of interest, through which highly specific antibodies against all proteins can be effectively and rapidly prepared with low cost, and the epitope to which the antibody is directed can be determined, so that a library covering epitopes on the surface of the proteins of interest and a library of antibodies against all the epitopes can be established. The antibodies are proved to be useful in detection, protein function investigation and antibody pharmaceuticals.

33 Claims, 4 Drawing Sheets

(56) References Cited

OTHER PUBLICATIONS

Zebedee et al. (Apr. 15, 1992) Proceedings of the National Academy of Sciences USA vol. 89 pp. 3175 to 3179.*
Kniskern et al. (1989) Immunobiology of Proteins and Peptides V pp. 83 to 98.*
Whitacre et al. (2009) Expert Reviews Vaccines vol. 8 pp. 1565 to 1573.*
Meng, L., "Research of Genetically Engineered Antibody Against BoNT/B Based on Epitope Prediction," Chinese Doctoral Dissertations Full-text Database (Doctor) Basic Science, Dec. 15, 2006, No. 12, ISSN 1671-6779, China Doctoral Dissertations Full-text Database [online], [retrieved on Mar. 23, 2012]. Retrieved from: CNKI, Beijing, China, 114 pages.
Huang, Z. et al., "Human Argonaute3 Protein: Preparation and Characterization of Polyclonal Antibody and the Antigen Distribution in Tumor Tissues by Tissue Array," Chinese Journal of Immunology, Mar. 2009, vol. 25, No. 3, pp. 243-246.
Pan, Y. et al., "Preparation of Antibody Against Utrophin Based on HBc Particles as the Expression Vector," Jiangsu Medical Journal, Nov. 2006, vol. 32, No. 11, pp. 1037-1039.
International Search Report, PCT/CN2012/070768, Date of Mailing: Apr. 26, 2012, 4 pages.

* cited by examiner

ANTIBODY PREPARATION METHOD, AND ANTIBODY AND ANTIBODY LIBRARY THUS PREPARED

CROSS-REFERENCE OF THE RELATED APPLICATION

The present application is a 35 U.S.C. §371 National Phase Entry Application of PCT/CN2012/070768, filed 30 Jan. 2012, designating the United States, which in turn claims priority to Chinese Patent Application No. 201110034648.7, filed on 31 Jan. 2011, both of which are incorporated herein by reference.

SEQUENCE SUBMISSION

The present application includes a Sequence Listing filed in electronic format. The Sequence Listing is entitled 2398105SequenceListingRevised.txt, created on 17 Dec. 2015 and is 68 kb in size. The information in the electronic format of the Sequence Listing is incorporated herein by reference in their entirety.

TECHNICAL FIELD

The present invention relates to a method for the preparation and/or screening of a specific antibody for a protein of interest. The present invention specifically relates to a high-throughput, low-cost method with high success rate, which can be used for predicting epitopes of a protein of interest at proteome level, preparing specific antibodies thereof, and screening and examining the thus produced antibodies.

TECHNICAL BACKGROUND

The developments of genomic techniques provide a great deal of basic information at gene level for the investigation of biological functions, diagnosis and treatment of disease, and development of medicaments etc. But for most of the biological systems, the gene information alone is not sufficient for illustrating the function mechanism thereof. Furthermore, if these information as well as the function mechanism are to be used for the purposes of applications, such as identification and analysis for pathological conditions, and verification and determination for the function mechanism of medicaments, then it will be necessary to further obtain more information at the protein level, such as analysis and investigation for various protein propertied like the structure, the function, the expression, the localization, the modification, and the interaction etc.

The identification for various properties of a protein will need many technical means, such as MS, chromatography, electrophoresis, chip, and various labeling techniques. Many of these technical means will need to be carried out based on antigen-antibody interactions. Further, antigen-antibody interaction per se is also an important technical means, which can be widely used in various fields like scientific researches, medical treatment, and medicament development, such as the development of therapeutic antibody medicament etc. With the development of protein researches, the demand for various antibodies as well as antibody libraries is increasing. For example, it could be necessary to prepare a specific antibody library against all the proteins in the proteome of a specie, or to prepare specific antibodies against a particular type of proteins like kinases or G-protein receptors. However, only limited amount of antibodies against several thousands of proteins are known in the art, and the specificities thereof are not sufficient for the requirements of many technical means. Therefore, it would be important to rapidly and effectively prepare large amount of antibodies against any protein of interest.

Currently, the commonly used methods for obtaining antibodies include hybridoma techniques, recombinant antibody techniques, various molecular display techniques, and the combination of these techniques with high-throughput techniques.

For the preparation of antibodies, generally a native or recombinant protein or fragment thereof is used to immunize an animal, so that an antibody that can specifically recognize and bind the protein is produced in the animal. Then various technical means can be used based on corresponding requirements to obtain antibody from the animal, such as monoclonal antibody or polyclonal antibody. The production of monoclonal antibody will typically rely on hybridoma techniques. In such techniques, after immunizing the animal, the cells of the animal will be taken and fused to generate an antibody-producing hybridoma, which will then be cloned to construct a strain for producing antibody, and subsequently the antibody will be purified and identified. The antigen's epitope for the antibody can also be further determined according to the requirements. Such hybridoma techniques for producing monoclonal antibodies were first applied in mouse model (Köhler and Milstein, Nature vol. 256, 1975). Currently they are widely used in various animal models, and the detailed procedure thereof can be seen in various textbooks and operation manuals (such as, Bazin, "Rat hybridomas and rat monoclonal antibodies", CRC Press, 1990; Goding, "Monoclonal antibodies: principles and practice", $3^{rd}$ edition, Academic Press, 1996; Shepherd and Dean "Monoclonal antibodies" Oxford University Press, 2000 etc.). Although these methods currently are widely used in the preparations of antibodies, they also have many disadvantages, such as very long preparation periods, very complicated preparation techniques, incomplete recognition of epitopes, and high cost etc. Further, such methods cannot be used for all the proteins, e.g. for many antigens with low immunogenicity or antigens with toxicity, such methods would be inappropriate (Sinclair N R (et al, 2004) B cell/antibody tolerance to our own antigens. Front Biosci 9: 3019-3028).

Furthermore, in order to obtain monoclonal antibodies with specificity, generally, a chemical synthesized peptide fragment is coupled to a carrier protein, which is then used to immunize a mouse. Such a method can generate an antibody against a single epitope of one protein. But due to the differences in the immunogenicity of different fragments, the overall success rate of such a strategy is relatively low, and especially for proteins with high homology, the fragments of which have poor immunogenicity and can hardly stimulate the mouse to produce potent immune responses. Another commonly used strategy is to produce the immunogen with full length protein or protein fragment, which can partially solve the above problem; but there still exists an disadvantage of poor overall success rate for protein expression (30-70% for commonly used expression and purification systems)(Thorsten Kohl, Christian Schmidt, Stefan Wiemann, Annemarie Poustka and Ulrike Korf. Drew, 2003). For protein fragments with high homology with the proteins of the animal used as model, the immune responses in the animal are generally very weak, and thus the success rate for preparing monoclonal antibody is quite low (Sinclair N R et al, 2004, Automated production of recombinant human proteins as resource for proteome research Proteome Science 2008, 6:4; Sinclair N R (2004) B cell/antibody tolerance to our own antigens. Front Biosci 9: 3019-3028).

The techniques of recombinant antibody can be various molecular display techniques, so as to produce antibodies (with high affinity to the target) against several antigens, and the antigen epitopes can also be simultaneously determined. Therefore, they are commonly used in the development of medicaments (Christine Rothe, Stefanie Urlinger, Makiko Yamashita et al. The Human Combinatorial Antibody Library HuCAL GOLD Combines Diversification of All Six CDRs According to the Natural Immune System with a Novel Display Method for Efficient Selection of High-Affinity Antibodies. J. Mol. Biol. (2008) 376, 1182-1200, 2007). However, the operation of the techniques of recombinant antibody is complicated, the cost thereof is high, and the yield thereof is relatively low. Further, there often exists non-specific binding. Therefore the large scale application of such techniques is limited. (Levitan, B. Stochastic modeling and optimization of phage display. *J. Mol. Biol.* 277, 893-916 (1998). Bradbury et al, 2004)

In order to increase the efficiency of immunization and screening, the above techniques can be combined with high-throughput methods, such as the high-throughput strategy in which several immunogens are simultaneously used for the immunization and chip techniques are used for the screening, e.g. as described in CN200510026873.0. However, such immunization strategy will require a great amount of immunogens with high immunogenicity. This can hardly be accomplished for proteins that are difficult to be expressed, or for proteins with very low immunogenicity.

Furthermore, in conventional immunization methods using several immunogens, the epitope that the produced antibody is directed to can only be passively determined based on the requirements using particular techniques such as epitope mapping after the antibody is produced (see, Glenn E. Morris, "Methods in Molecular Biology: Epitope Mapping Protocols", Humana Press, 1996). Sometimes the epitope is not unique for the protein of interest, and can present in many other proteins, such that the specificity of the produced antibody is relatively low.

In order to solve the various problems mentioned above, new methods for preparing and screening antibodies are desired, so as to effectively and rapidly prepare and screen high specific antibodies against all the proteins with low cost.

SUMMARY OF THE INVENTION

The present invention provides a method for preparing an antibody against a protein of interest, the method comprises: (a) predicting and/or selecting peptide fragment located on the surface of the protein of interest; (b) synthesizing or expressing one or more of said peptide fragments; (c) using the product of step (b) to immunize an animal, optionally in combination with an adjuvant; (d) using lymphocyte from the immunized animal of step (c) to obtain antibodies; (e) using the peptide fragment of step (a) or said protein of interest in native conformation thereof to screen the antibodies obtained in step (d), so as to obtain an antibody library against said protein of interest.

In one embodiment, in the method of the invention, said peptide fragment of step (a) is predicted or selected through the following process: (i) determining a surface peptide by calculating a parameter according to the sequence of the protein of interest, said parameter is selected from: solvent accessibility, disorder index, protein-protein interaction domain prediction, or any combination thereof; (ii) aligning the surface peptide determined in step (i) with the proteome of the specie that the protein of interest is originated from, so as to select a specific peptide fragment of said protein of interest; and (iii) aligning the surface peptide determined in step (i) with homologous proteins from other species, so as to screen a conservative sequence of said protein of interest.

In one embodiment, said peptide fragment of step (a) in the method of the invention is a linear surface signature peptide and/or a conformational surface signature domain of the protein of interest. In one embodiment, said signature peptide is characterized in that: it is 6-12 amino acids in length, it is high hydrophilic, it has high antigenicity, it is not a signal peptide, it is not located in trans-membrane region but rather in disordered region. In another embodiment, said signature domain is a sequence specific protein fragment which is 100-500 amino acids in length, and which is expected to have 3 dimensional structure.

In one embodiment, one or more of the peptide fragments of step (b) in the method of the invention are recombinantly expressed in the form of a fused protein with a protein which enhances the immunogenicity and/or increases the copy number. In one embodiment, the protein which enhances the immunogenicity and/or increases the copy number is a virus-like particle protein carrier. In one embodiment, said virus-like particle protein carrier is Hepatitis B virus nucleocapsid (HBc) protein. In one embodiment, said one or more peptide fragments are inserted into loop, N-terminus, or C-terminus of the HBC protein, e.g. the inserted site can be located between the amino acid residue at position 77 and the amino acid residue at position 82 of the HBC protein. In one embodiment, 2-10 of the peptide fragments linked by linker are inserted into the HBC protein. Said linker can be $(GGGGS)_n$, (SEQ ID NO:158)$_n$, wherein n is any integer, such as 1, 2, 3, or 4.

In one embodiment, the one or more peptide fragments expressed in step (b) are further coupled with an immune-enhancing protein carrier. In one embodiment, said immune-enhancing protein carrier is keyhole limpet hemocyanin (KLH).

In one embodiment, the one or more peptide fragments of step (b) are chemically synthesized.

In one embodiment, the immunization of step (c) in the method of the invention is optionally performed in combination with an adjuvant, e.g. an adjuvant selected from: Freund's complete adjuvant, aluminum, CpG, or any combination thereof.

In one embodiment, in said step (c) of the method of in invention, the animal is immunized at multiple sites, e.g. at least 2 sites selected from: neck and back, tail end, hind foot palm, hind leg inguen, front leg armpit, hind leg muscle.

In one embodiment, multiple immunizations are performed, with the time interval of 2-14 days, such as 3-4 days.

In one embodiment, the immunization protocol used in step (c) of the method of the invention comprises the following steps:
  (A) the first immunization: the expression product of step (b) together with Freund's complete adjuvant are used to immunize the animal at neck and back, tail end, hind foot palm, hind leg inguen, and front leg armpit; and the expression product of step (b) together with the adjuvant of aluminum+CpG are used to immunize the animal at hind leg muscle;
  (B) the second immunization: the expression product of step (b) together with Freund's complete adjuvant are used to immunize the animal at neck and back, hind leg inguen, and front leg armpit; and the expression product of step (b) together with the adjuvant of aluminum+ CpG are used to immunize the animal at hind leg muscle;

(C) the third immunization: the expression product of step (b) together with the adjuvant of aluminum+CpG are used to immunize the animal at hind leg muscle, tail end, and front leg armpit; and (D) the fourth immunization: the expression product of step (b) together with the adjuvant of aluminum+CpG are used to immunize the animal at hind leg muscle, tail end, and front leg armpit.

In one embodiment, the first immunization is performed on the first day, the second immunization is performed on the fifth day, the third immunization is performed on the eighth day, and the fourth immunization is performed on the eleventh day.

The antibody obtained in step (d) of the method of the invention is obtained through at least one process selected from: (1) fusing lymphocyte from the immunized animal of step (c) with amyeloma cell, so that a hybridoma is generated and then expressed to obtain the antibody; (2) isolating antigen specific B cell from lymphocyte of the immunized animal of step (c), and then using PCR to clone and express the gene of the antibody so as to obtain the antibody; or (3) isolating mRNA from lymphocyte of the immunized animal of step (c), and then obtaining the antibody through phage display, or ribosome display, or yeast display, or bacteria display, or baculovirus display, or mammal cell display, or mRNA display.

In one embodiment, the antibody produced in the method of the invention is singly IgG subtype.

In one embodiment, the antibody library produced in step (e) of the method of the invention is an antibody library against all the proteins of a specie. In another embodiment, the antibody library produced in step (e) of the method of the invention comprises antibodies against all the epitopes of the protein of interest.

In one embodiment, the antibodies produced in step (d) are screened through affinity sorting in step (e) of the method of the invention.

The method of the invention can also comprise a further step (f) of screening functional antibody and detection antibody. For example, said detection antibody is screened through Western blotting, IP, IF, IHC, flow cytometry, ELISA, or any combination thereof; said functional antibody is screened through blocking or neutralizing assay.

In another aspect, the invention provides a method for determining epitopes of a protein of interest, and said method comprises the step of using the peptide fragment predicted and/or screened in above mentioned step (a) to construct a detection antigen, which can be used to screen the produced antibodies so as to determine the epitopes.

DETAILED DESCRIPTION OF THE INVENTION

Figure 1:
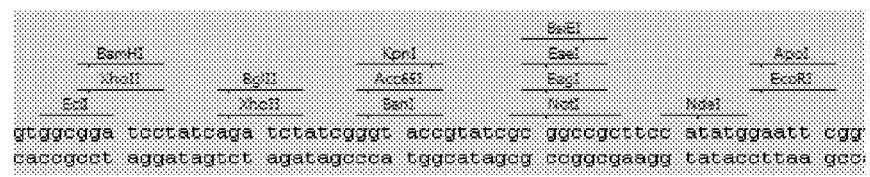
FIG. 1: the design diagram and nucleotide sequence of the multiple cloning site. The upper strand sequence is set forth in SQ ID NO:159, and the lower strand is set forth in SEQ ID NO:160.
Figure 2:
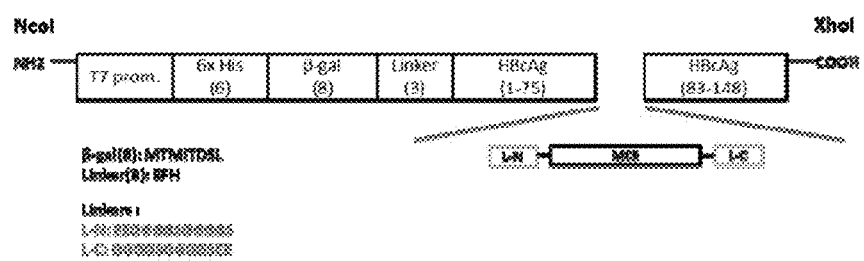
FIG. 2: schematic diagram of artificial HBc. The β-gal(8) sequence is set forth in SEQ ID NO:161. The L-N linker is set forth in SEQ ID NO:162. The L-C linker is set forth in SEQ ID NO:163.

Unless otherwise specified, all the technical and scientific terms have common meanings known to a person skilled in the art. The patents, patent applications, publications, GenBank sequences, websites and other published material are all incorporated herein as references in their entirety, unless otherwise specified.

The present invention provides a method for producing an antibody of a protein of interest, which can be used to efficiently and rapidly prepare highly specific antibodies of the protein with low-cost, so as to construct a epitope library encompassing the surface epitopes of a protein of interest and an antibody library against all the epitopes. The method also provides a method for indicating the specific epitope that an antibody is directed to.

The present invention provides a method for preparing an antibody against a protein of interest, the method comprises: (a) predicting and/or selecting peptide fragment located on the surface of the protein of interest; (b) synthesizing or expressing one or more of said peptide fragments; (c) using the product of step (b) to immunize an animal, optionally in combination with an adjuvant; (d) using lymphocyte from the immunized animal of step (c) to obtain antibodies; (e) using the peptide fragment of step (a) or said protein of interest in native conformation thereof to screen the antibodies obtained in step (d), so as to obtain an antibody library against said protein of interest.

As used herein, the term "a protein of interest" refers to any native protein, or an isoform of a native protein obtained through alternative splicing, or a mutant of a native protein, or any combination of the various proteins mentioned above. "Alternative splicing" as used herein refers to a process of producing different mRNA splicing isomers from a same mRNA precursor through different splicing manners (i.e. combining exons through different splicing sites). The protein products obtained through alternative splicing are isoforms to each other, which may exhibit different functional and structural properties, or may result in different phenotypes due to different expression levels in a same cell. "Mutant" as used herein refers to a mutated protein obtained through substitution, deletion, or addition of one or more amino acids in a native protein.

The term "peptide fragment" as used herein refers to a continuous or incontinuous amino acids sequence in the protein of interest, which can be a continuous linear polypeptide, and which can also be a combination of incontinuous polypeptides constituting the domain conformation.

In one embodiment of the invention, said peptide fragment of step (a) is predicted or selected through the following process: (i) determining a surface peptide by calculating a parameter according to the sequence of the protein of interest, said parameter is selected from: solvent accessibility, disorder index, protein-protein interaction domain prediction, or any combination thereof; (ii) aligning the surface peptide determined in step (i) with the proteome of the specie that the protein of interest is originated from, so as to select a specific peptide fragment of said protein of interest; and (iii) aligning the surface peptide determined in step (i) with homologous proteins from other species, so as to screen a conservative sequence of said protein of interest. In one embodiment, said peptide fragment in step (a) is linear surface signature peptide and/or a conformational surface signature domain of the protein of interest.

The term "surface peptide" as used herein refers to linear peptide fragment located on the surface of the protein of interest, and/or combination of incontinuous polypeptides located on the surface of the protein of interest that constitute the domain conformation. The term "signature peptide" as used herein refers to a unique linear continuous peptide sequence in the protein of interest when compared to other protein sequences in the proteome of the same specie. The term "signature domain" as used herein refers to a unique domain in the protein of interest when compared to the domains of other protein in the proteome of the same specie. The term "surface signature peptide" and "surface signature domain" respectively refer to "signature peptide" and "signature domain" located on the surface of the native conformation of a protein.

The term "solvent accessibility" refers to an indicator representing the degree that an amino acids within a protein exposes to the conformational surface of the protein (see, Bent Petersen, Thomas Nordahl Petersen, Pernille Andersen Morten Nielsen and Claus Lundegaard. A generic method for assignment of reliability scores applied to solvent accessibility predictions. *BMC Structural Biology* 2009, 9:51).

The term "disorder index" used herein is a parameter representing the complexity of amino acids (see, Predrag Radivojac, Lilia M. Iakoucheva, Christopher J. Oldfield, Zoran Obradovic, Vladimir N. Uversky, and A. Keith Dunker. Intrinsic Disorder and Functional Proteomics. Biophysical Journal Volume 92, 1439-1456 (2007)).

As used herein, "protein-protein interaction domain prediction" means that, in protein-protein interaction, some domains play a key role in the interaction, and binding manner of two proteins can be predicted by analyzing the amino acid composition of the proteins. Typical software such as Autodock can be used (see, Bin Liu, Xiaolong Wang, Lei Lin, Buzhou Tang, Qiwen Dong and Xuan Wang. Prediction of protein binding sites in protein structures using hidden Markov support vector machine. *BMC Bioinformatics* 2009, 10:381).

As used herein, the term "proteome" refers to the collection of all the proteins expressed by the genome of a certain specie, or by a certain cell or tissue or cell.

The sequence alignment in the invention can be performed using various methods known in the art, such as using various conventional softwares or online services, e.g. BLASTP as provided by NCBI.

The prediction and/or selection in the invention mean that: based on bioinformatics methods, through secondary structure prediction, comparison in the same genome, structural prediction of homologous proteins, signature peptides and/or signature domains are first defined for a certain protein as potential epitopes, wherein said signature peptides and/or signature domains have protein specificity and can cover relatively large portion of the protein.

Such bioinformatics methods are widely used for the prediction of protein structures, functions and interactions. For example, Berglund L. et al. (see, Protein Science, 17:606-613, 2008) introduced a method for screening specific epitopes at proteome level against the entire human proteome, wherein based on sequence alignment for sliding windows of 8, 10, 12 amino acid residues, heuristic processes are used to predict the sequence identity of every human protein against the entire human proteome. Based on such method, at least one specific epitop can be found for 90% of human protein. Anderson H P et al. (see, Protein Science, 15:2558-2567, 2006) introduced method Disco-Tope for predicting incontinuous epitopes using 3D structural data. This method assesses amino acids statistics, spatial information, and surface accessibility based on incontinuous epitopes determined in X-ray structure of antigen-antibody protein complex. Yan C H et al. (see, BMC Bioinformatics, 7:262, 2006) introduces a method for predicting potential DNA-biding sites through amino acid sequence, which uses Naïve Bayes classifier to predict whether a certain amino acid sequence is a DNA-binding site.

In one embodiment, the signature peptide of the invention is 6-12 amino acids in length, it is high hydrophilic, it has high antigenicity, it is not a signal peptide, and it is not located in trans-membrane region but rather in disordered region. In one embodiment, the signature domain of the invention is a sequence specific protein fragment which is 100-500 amino acids in length, and which is expected to have 3 dimensional structure.

In one embodiment, in step (a) of the method of the invention, several peptide fragments located on the surface of the protein of interest are predicted and/or selected, e.g. 2, 3, 4, 5, 6, 7, 8, 9, 10 peptide fragments, until all the peptide fragments located on the surface of the protein of interest that can be used as potential epitopes are predicted and/or selected.

In one embodiment, said several peptide fragments are designed as one tandem polypeptide of immunization antigens. For example, said tandem polypeptide of immunizing antigens can be designed as follows: predicting immunizing parameters of the protein of interest, such as antigenicity, hydrophilicity, accessibility, isoelectric point, predicting the signaling, and predicting the trans-membrane region; the setting rules for parameters like specificity can be seen in Kolaskar A S et al. FEBS Lett. 276 (1-2):172-4, 1990; Parker J M et al., Biochemistry. 25(19):5425-32, 1986; Emini E A et al., J. Virol. 55(3): 836-9, 1985. For any protein of interest, the prediction results for isoelectric point and signal-peptide are first used to exclude these regions in the protein. For example, a sliding window with the length of 5-20 amino acids can be set, and then sequentially moved for one amino acid along the protein. The sequences of the sliding windows are added into a collection. As an example, for a protein with the length of n amino acids (suppose it has no signal-peptide or trans-membrane region), all together n−9 short peptide sequences can be generated (the length of the sliding window is 10 amino acids). For every short peptide, the isoelectric point, accessibility, immunogenicity, hydrophilicity, and specie specificity according to BLAST methods can be calculated (see, Kolaskar A S et al., FEBS Lett. 276 (1-2):172-4, 1990; Parker J M et al., Biochemistry. 25(19):5425-32, 1986; Emini E A et al., J. Virol. 55(3): 836-9, 1985). When the isoelectric point is larger than 3.5, the weighted average value of the above parameters are calculated for every short peptide (0.2*immunogenicity+ 0.1*accessibility+0.2*hydrophilicity+0.5*specie specificity). These short peptides are sorted according to the weighted average value, and the short peptides having the highest score and with an inter-peptide overlap <3 are selected, e.g. 7 short peptides are selected.

The peptide fragment of the invention can be obtained by any known techniques in the art, e.g. by recombinant expression or by chemical synthesis. That is, the peptide fragment of the invention can be expressed in prokaryotic or eukaryotic expression systems using recombinant expression methods known in the art, or the peptide fragment can be synthesized using conventional chemical methods.

In one example, e.g. for a protein the expression and purification of which are difficult, or for a protein which has very low immunogenicity, in order to prepare specific antibodies, expression vectors with high immunogenicity and soluble protein expression systems with high success rate can be used to facilitate the production of these proteins as potential antigens. Virus-like particle protein carrier Hepatitis B virus nucleocapsid (HBc) protein can be mentioned as an example.

HBC protein is a non-infectious virus-like particle carrier that can carry peptides of various sources. It can be used to combine target peptide so as to generate high-titer antibody response, and thus is widely used in vaccine preparation. HBC protein can carry foreign amino acids at particular sites such as loops, N-terminus or C-terminus, and a foreign sequence of up to 238-amino acids can be displayed on the surface of the protein so as to promote the generation of immune-response. Detailed description of HBC carrier can be seen in: Good M F et al., Science, 235:1059-1063, 1987; Pumpens P and Grens E, Intervirology, 44:98-114, 2001; Clarke B E et al., Nature 330:381-384, 1987; Francis M J et al., Nature 330:168-170, 1987; Whitacre D C et al., Expert Rev. Vaccines 8:11 1565-1573, 2009.

In one embodiment, the one or more peptide fragments in step (b) of the method of the invention are inserted into loop, N-terminus, or C-terminus of the HBC protein, e.g. into a position between the amino acid residue at position 77 and the amino acid residue at position 82 of the HBC protein. 2-10 of the peptide fragments of the invention can also be linked by linker and then inserted into the HBC protein. Said linker can be any linker in the art, e.g. (GGGGS)$_n$, wherein n is any integer, such as 1, 2, 3, or 4.

For instance, in one example, N (5≤N≤20) peptide fragments with relatively high immunogenicity and specificity are selected, and the lengths thereof may be M (5≤M≤20) amino acids. In order to avoid the generation of new antigen epitope between different peptide fragments, one or more linkers GGGGS with low immunogenicity are inserted between different peptide fragments, so as to connect said peptide fragments in tandem. For different lengths of proteins, different lengths (5≤M≤20) of the peptide fragment can be selected. The number of the inserted fragments can be between 5-20, the length of the peptide fragment can be, e.g. 6-12 amino acids, and the number of the fragments can be, e.g. less than 10.

In an embodiment of the invention, the one or more peptide fragments expressed in step (b) can also be further coupled with an immune-enhancing protein carrier, and said immune-enhancing protein carrier can be, e.g. keyhole limpet hemocyanin (KLH). KLH protein is an oxygen-carrying metalloprotein originated from *Megathura crenulata*, which is commonly used as carrier protein for generating antibodies. The many epitopes contained therein and its differences with mammal-derived protein make KLH a good carrier protein for generating antibodies. The applications of KLH protein can be seen in Harris J R et al., Micron. 30(6):597-623, 1999 and WO 2001/047552.

The immunization of animal in step (c) can be conducted using any methods known in the art. The animal used for immunization in the invention can be conventional animals in the art, e.g. mouse, rat, rabbit, sheep, goat, horse, cattle etc.

In one embodiment, an appropriate adjuvant can be used, so as to rapidly and effectively obtain antibodies of a single subtype and with high titer. In one embodiment, the antibodies obtained through the method of the invention can be antibodies mainly comprising single IgG subtype. The adjuvant used in the invention can be selected from: Freund's complete adjuvant, aluminum, CpG, or any combination thereof.

In one embodiment, the method of the invention comprises multiple immunizations in an animal. The specific protocol of using multiple sites immunization strategy for rapid production of antibodies with high affinity can be seen in Kilpatrick K E et al., (Hybridoma 16:(4) 381-389, 1997). The protocol for adjusting the affinity and subtype of antibodies can be seen in Karagouni L et al., Scand. J. Immunol. 31:745-754, 1990, and Petty R E et al., Immunology 32:49-55, 1977.

The multiple immunizations in an animal of the invention can be conducted at at least 2 sites selected from: neck and back, tail end, hind foot palm, hind leg inguen, front leg armpit, hind leg muscle.

In one embodiment of the invention, multiple immunizations are conducted in an animal. The time interval between multiple immunizations can be determined based on common technical knowledge in the art, e.g. 2-14 days, such as 3 or 4 days.

In one embodiment, the immunization in step (c) of the method of the invention comprises the following steps:

(A) the first immunization: the expression product of step (b) together with Freund's complete adjuvant are used to immunize the animal at neck and back, tail end, hind foot palm, hind leg inguen, and front leg armpit; and the expression product of step (b) together with the adjuvant of aluminum+CpG are used to immunize the animal at hind leg muscle;

(B) the second immunization: the expression product of step (b) together with Freund's complete adjuvant are used to immunize the animal at neck and back, hind leg inguen, and front leg armpit; and the expression product of step (b) together with the adjuvant of aluminum+CpG are used to immunize the animal at hind leg muscle;

(C) the third immunization: the expression product of step (b) together with the adjuvant of aluminum+CpG are used to immunize the animal at hind leg muscle, tail end, and front leg armpit; and (D) the fourth immunization: the expression product of step (b) together with the adjuvant of aluminum+CpG are used to immunize the animal at hind leg muscle, tail end, and front leg armpit.

In a more specific embodiment, the immunization in step (c) of the method of the invention comprises the following steps:
- (A) the first immunization: 20 µg of the expression product of step (b) in 250 µl buffer together with 250 µl Freund's complete adjuvant are used to immunize the animal at neck and back, tail end, hind foot palm, hind leg inguen, and front leg armpit; and 20 µg of the expression product of step (b) in 500 µl buffer together with the adjuvant of 25 µl aluminum+10 µg CpG are used to immunize the animal at hind leg muscle;
- (B) the second immunization: 10 µg of the expression product of step (b) in 250 µl buffer together with 250 µl Freund's complete adjuvant are used to immunize the animal at neck and back, hind leg inguen, and front leg armpit; and 10 µg of the expression product of step (b) in 500 µl buffer together with the adjuvant of 25 µl aluminum+10 µg CpG are used to immunize the animal at hind leg muscle;
- (C) the third immunization: 10 µg of the expression product of step (b) in 500 µl buffer together with the adjuvant of 25 µl aluminum+10 µg CpG are used to immunize the animal at hind leg muscle, tail end, and front leg armpit; and
- (D) the fourth immunization: 10 µg of the expression product of step (b) in 500 µl buffer together with the adjuvant of 25 µl aluminum+10 µg CpG are used to immunize the animal at hind leg muscle, tail end, and front leg armpit.

In one embodiment, the first immunization is performed on the first day, the second immunization is performed on the fifth day, the third immunization is performed on the eighth day, the fourth immunization is performed on the eleventh day, and the fusion is performed on the fourteenth day. The obtained antibodies are mostly IgG subtype with matured affinity. Antibodies of IgG subtype have the advantages of higher affinity, better stability and easier for purification as compared to IgM.

The antibody obtained from lymphocyte of the immunized animal in step (d) of the method of the invention can be obtained through any methods known in the art. As used herein, the term "lymphocyte" refers to a cell of lymphoid organs or a cell produced in lymphoid organs, and the lymphoid organs include central lymphoid organs (also referred to as primary lymphoid organ) and peripheral lymphoid organ (also referred to as secondary lymphoid organ). The former includes thymus, bursa of fabricius and equivalent organs thereof (such as marrow of mammals), and the latter includes spleen and lymph nodes etc.

In one embodiment, the antibody is obtained through at least one process selected from: (1) fusing lymphocyte from the immunized animal of step (c) with amyeloma cell, so that a hybridoma is generated and then expressed to obtain the antibody; (2) isolating antigen specific B cell from lymphocyte of the immunized animal of step (c), and then using PCR to clone and express the gene of the antibody so as to obtain the antibody; or (3) isolating mRNA from lymphocyte of the immunized animal of step (c), and then obtaining the antibody through phage display, or ribosome display, or yeast display, or bacteria display, or Baculovirus display, or mammal cell display, or mRNA display.

Detailed introductions for hybridoma technique can be seen in Bazin, "Rat hybridomas and rat monoclonal antibodies", CRC Press, 1990; Goding, "Monoclonal antibodies: principles and practice", $3^{rd}$ edition, Academic Press, 1996; Shepherd and Dean "Monoclonal antibodies" Oxford University Press, 2000, etc.

In step (d) of the method of the invention, the antibody can also be obtained through phage display, or ribosome display, or yeast display, or bacteria display, or Baculovirus display, or mammal cell display, or mRNA display. These methods are all conventional techniques in the art, the specific operations thereof can be seen in corresponding textbooks or operation manuals, see, e.g. Mondon P et al., Front. Biosci. 13:1117-1129, 2008. Using phage display as an example, separate antibody genes are inserted into the DNA of phage, so that the variable regions on the antibody molecules that can bind the antigens are coupled to the capsid protein of phage. After the phage infecting E. coli., single stranded DNA is replicated in E. coli., and the phage is reassembled and secreted into the culture medium, while the E. coli. is not lysed. The phage is co-incubated with target antigens; and after the bound phages are isolated, amplification and purification are then conducted so that a great amount of clones can be screened. The phage display technique can be seen in Liu, J. et al., Chin. J. Cell Mol. Immunol., 2004: 20 (6) 773-775; CN03131796.0; WO 2009/109572, and WO 2009/085462.

The antibody produced in the method of the invention can be monoclonal antibody, and can also be polyclonal antibody. In one embodiment, the invention involves an antibody library screened and prepared using the method of the invention against all the proteins of interest of one specie. In another embodiment, the invention involves an antibody library screened and prepared using the method of the invention against all the epitopes of one protein of interest.

As used herein, the terms "antibody", "monoclonal antibody", "polyclonal antibody", "epitope" are common term in the art, the meanings of which are in accordance with the general understanding of a person skilled in the art and can also be referred to common textbooks and manuals.

As used herein, the term "antibody library" refers to a collection of antibodies comprising many different antibodies. An antibody library can comprise antibodies against several different proteins, and it can also comprise antibodies against different epitopes of a same protein.

The "screen" used in step (e) of method of the invention means using the peptide fragment of step (a) or the protein of interest in its native conformation to screen the antibodies obtained in step (d). In one embodiment, the antibodies produced in step (d) is screened through affinity sorting in step (e) of the method of the invention. The identification method for an antibody can be seen in Griswold W R et al., Immunology letters, 1984: 229-232; Van Heyningen V et al., Journal of Immunological Methods, 62: 147-153, 1983; and Rath S et al., Journal of Immunological Methods, 106: 245-249, 1988.

In one embodiment, the method of the invention can also comprise a further step (f) of screening functional antibody and detection antibody. For example, said detection antibody is screened through Western blotting, IP, IF, IHC, flow cytometry, ELISA, or any combination thereof; or said functional antibody is screened through blocking or neutralizing assay The detection antibody as used herein refers to an antibody that can react with an antigen and can then be detected through techniques in the art, such as Western blotting, IP, IF, IHC, flow cytometry, or ELISA etc.

The functional antibody as used herein refers to an antibody that can react with an antigen and can then affect (e.g. block or neutralize) a biological function of the antigen.

As an example, antibodies against the protein of interest are screened using the following method: the protein of interest or fragment thereof is biotinylated, and then over-expressed in eukaryotic cells like 293 cells; the over-expressed biotinylated protein or fragment thereof is added into a plate coated with streptavidin; then the antibodies obtained in step (e) of the invention are added for ELISA assay, so as to obtain antibodies with positive reaction.

One monoclonal antibody 4A1 of the invention is produced by hybridoma strain 4A1, and said hybridoma strain 4A1 was deposited in China Center for Type Culture Collection (CCTCC) on Jan. 28, 2011, with the deposition No. CCTCC C201107. Another monoclonal antibody 1A6 of the invention is produced by hybridoma strain 1A6, and said hybridoma strain 1A6 was deposited in China Center for Type Culture Collection (CCTCC) on Jan. 28, 2011, with the deposition No. CCTCC C201108. One monoclonal antibody 2F1 of the invention is produced by hybridoma strain 2F1, and said hybridoma strain 2F1 was deposited in China Center for Type Culture Collection (CCTCC) on Jan. 28, 2011, with the deposition No. CCTCC C201109.

In another aspect, the present invention provides an antibody library produced according to the method of the invention. In one embodiment, said antibody library comprises antibodies against all the proteins of interest. In one embodiment, said antibody library comprise antibodies against all the epitopes on the surface of one protein of interest. In one embodiment, said antibodies in the library are monoclonal antibodies.

In another aspect, the present invention also provides a method for determining the epitope that the produced antibody is directed to, comprising the step of using the peptide fragments predicted and/or screened in above mentioned step (a) to construct a detection antigen, which can be used to screen the produced antibodies so as to determine the epitopes.

As used herein, the term "detection antigen" refers to a fused protein constructed using the peptide fragments predicted and/or screened in above steps. Said detection antigen can be used for conducting screening against several proteins, wherein it contains one epitope for each of the protein to be screened.

In one embodiment, the present invention utilizes a strategy that can conducts a screening against N proteins, and the number of epitopes and the number of proteins designed for each protein can all be N (5≤N≤20), with the prerequisite that number of epitopes selected for each protein is identical.

As an example, for 5 proteins, 5 antigen epitopes are determined for each protein during the design of the immunization antigens, which are represented by A, B, C, D, E respectively (see table 1). For example, the epitopes for immunization antigen are A1, B1, C1, D1, and E1 respectively. The number of epitopes and the number of proteins here can both be N (5≤N≤20).

The detection antigen for 5 proteins uses the five polypeptide epitopes in one column as one new protein sequence (see table 1, e.g., detection antigen A comprises A1, A2, A3, A4, and A5).

During the screening process, every fused positive cloning well (obtained by screening of immunization antigens), is respectively screened using 5 detection antigens, and through typical ELISA screening, so as to determine which polypeptide epitope each positive clone is directed to. Based on such results, positive cells directed to each epitopes are preferably selected for strain construction and subsequent identification, so as to avoid the situation when the epitopes are unknown and the positive clones are mostly directed to a certain most advantageous epitope so that the obtained cell strains are homogeneous.

TABLE 1

The design method for immunization antigen

| | detection antigen A | detection antigen B | detection antigen C | detection antigen D | detection antigen E |
|---|---|---|---|---|---|
| immunization antigen 1 | A1 | B1 | C1 | D1 | E1 |
| immunization antigen 2 | A2 | B2 | C2 | D2 | E2 |
| immunization antigen 3 | A3 | B3 | C3 | D3 | E3 |
| immunization antigen 4 | A4 | B4 | C4 | D4 | E4 |
| immunization antigen 5 | A5 | B5 | C5 | D5 | E5 |

In summary, the method of the invention uses bioinformatics techniques to predict and/or select peptide fragments on the surface of a protein of interest as potential epitopes. The method of the invention can be used to effectively and rapidly obtain antibodies against a protein of interest with low cost, and the method of the invention can be used to obtain all the antibodies against epitopes on the surface of the native conformation of a protein of interest. Furthermore, the method of the invention can also use combination screening to determine epitopes on the surface of the native conformation of a protein of interest through, identify the particular epitope that an antibody is directed to, and further examine and screen the produced antibodies.

The several key factors for successful applications of an antibody include the recognition site of the antibody (epitope), affinity and specificity. As for monoclonal antibody, when the epitopes are unknown, the obtained antibodies are generally focused on a certain epitope with advantageous immunogenicity. The unity of epitopes can result in failure when applying an antibody, which is mainly related to the position of the epitope. In the case when the epitopes that the antibodies recognize are known, then antibodies of several epitopes are preferably obtained, so that the influences of incorrect epitope position can be decreased, and the success rate of cell strain applications can be greatly increased.

The advantage of the invention lies in the preparation of large amount of antibodies. The method has the propertied of high success rate (antibodies successfully used in Western applications can be obtained for >90% of the proteins), and low-cost. The success rates for proteins with high homology, receptor protein domains, and proteins of mouse are all very high. The significance of preparing antibodies against mouse proteins is in that, the functional antibodies screened therefrom, can be used for antibody treatment experiments in mouse models, which is important for clinical researches. As for membrane receptor proteins, when using functional domains to prepare antibodies, it will be more advantageous in obtaining antibodies with blocking functions, and benefits the developments of antibody medicaments. The antibody library constructed using the method of the invention can be further used for developing functional antibodies. Furthermore, the high-throughput epitope screening strategy ensures that the corresponding epitope recognition information is specifically clear for every cell strain obtained, which is important both for investigating antibody-protein interactions and for using several epitopes to determine the expression information of a certain protein.

The invention will be further illustrated using the following specific examples. The following examples are only used for describing the invention, with no intention of limiting the present invention. Various modifications and alterations may be made to the invention by one skilled in the art without departing from the spirit and scope of the invention, and such modifications and alterations are also encompassed in the protection scope as defined in the appended claims.

EXAMPLES

Example 1

Modification of Vectors

A The Design for HBC Vector Modification

First a segment of designed multiple cloning site (MCS: GGATCCTATCAGATCTATCGGGTACCGTATCGCGGC-CGCTTCCAT ATGG AA TTC (SEQ ID NO: 1)) was used to replace the c/e1 loop of the cDNA for Hepatitis B virus nucleocapsid protein (HBc), i.e. the nucleotides encoding the amino acids at positions 76-82 of HBc protein. The schematic diagram and sequence of said MCS can be seen in FIG. 1. Then, the nucleotide sequences encoding the two linkers L-N and L-C were linked to the two ends of said MCS, and the nucleotides encoding amino acids at position 76-82 of HBc protein were replaced, wherein in the two ends of the two linkers L-N and L-C, the E represented glutamic acid, G represented glycin, and S represented serine. Subsequently, the nucleotide sequences encoding the sequence elements 6×His tag (HHHHHH; SEQ ID NO:164), β-gal (MTMITDSL; SEQ ID NO:161), and linker (EFH) were added to in front of the cDNA. The nucleotide sequence of the modified HBc is shown in FIG. 2.

B Complete Gene Synthesis

DNA Works software (obtained from http colon slash slash helixweb dot nih dot gov slaxh dnaworks/) was used to design HBc nucleotide sequence through codon optimization, as shown below:

```
                                              (SEQ ID NO: 2)
CCATGGGCAGCAGCCACCATCATCACCACCACATGACCATGATCACCGA
TAGCCTGGAGTTCCATATCGATCCGTACAAGGAATTTGGCGCGACCGTG
GAACTGCTGAGCTTCCTGCCGAGCGACTTTTTTCCAAGCGTGCGTGACC
TGCTGGATACGGCGAGCGCACTGTATCGTGAAGCGCTGGAAAGCCCGGA
ACATTGCAGCCCGCATCATACCGCGCTGCGTCAGGCGATTCTGTGCTGG
GGCGAACTGATGACCCTGGCGACCTGGGTGGGCGGCAATGAAGAAGGTG
GTGGCGGTAGCGGCGGTGGCGGATCCTATCAGATCTATCGGGTACCGTA
TCGCGGCCGCTTCCATATGGAATTCGGTGGCGGCGGCAGCGGCGGTGGT
GGCAGCGAAGAAGACCTGGTTGTGAGCTATGTGAACACCAATATGGGCC
TGAAGTTTCGTCAGCTGCTGTGGTTTCATATTAGCTGCCTGACCTTTGG
CCGCGAAACCGTGATTGAATACCTGGTGAGCTTTGGCGTGTGGATTCGT
ACCCCACCGGCGTATCGTCCGCCGAATGCGCCAATTCTGAGCACCCTGC
CGGAAACGACCGTTTAAGAGCTCCGTCGACAAGCTTGCGGCCGCACTCG
AG
```

The optimized HBC nucleotide sequence was synthesized using the following primers as shown in table 2, and primers as shown were synthesized by SBSGENE co. ltd. (Shanghai, China).

TABLE 2

The primer sequences for complete gene synthesis

| Name of primers | Sequences of the primers (5'-3') |
|---|---|
| H_01 | CATG CCATGGGCAGCAGCCACCATCATCACCACCACATGACC (SEQ ID NO: 3) |
| H_02 | CTCCAGGCTATCGGTGATCATGGTCATGTGGTGGTGATGA (SEQ ID NO: 4) |
| H_03 | TGATCACCGATAGCCTGGAGTTCCATATCGATCCGTACAAGG(SEQ ID NO: 5) |
| H_04 | CCACGGTCGCGCCAAATTCCTTGTACGGATCGATATGGAA(SEQ ID NO: 6) |
| H_05 | TGGCGCGACCGTGGAACTGCTGAGCTTCCTGCCGAGCGAC(SEQ ID NO: 7) |
| H_06 | CAGGTCACGCACGCTTGGAAAAAAGTCGCTCGGCAGGAAG(SEQ ID NO: 8) |
| H_07 | CAAGCGTGCGTGACCTGCTGGATACGGCGAGCGCACTGTA(SEQ ID NO: 9) |
| H_08 | TCCGGGCTTTCCAGCGCTTCACGATACAGTGCGCTCGCCG(SEQ ID NO: 10) |
| H_09 | CGCTGGAAAGCCCGGAACATTGCAGCCCGCATCATACCGC(SEQ ID NO: 11) |
| H_10 | CAGCACAGAATCGCCTGACGCAGCGCGGTATGATGCGGGC(SEQ ID NO: 12) |
| H_11 | GTCAGGCGATTCTGTGCTGGGGCGAACTGATGACCCTGGC(SEQ ID NO: 13) |
| H_12 | TTCATTGCCGCCCACCCAGGTCGCCAGGGTCATCAGTTCG(SEQ ID NO: 14) |

TABLE 2-continued The primer sequences for complete gene synthesis

| Name of primers | Sequences of the primers (5'-3') |
|---|---|
| H_13 | GGTGGGCGGCAATGAAGAAGGTGGTGGCGGTAGCGGCGGT(SEQ ID NO: 15) |
| H_14 | ACCCGATAGATCTGATAGGATCCGCCACCGCCGCTACCGC(SEQ ID NO: 16) |
| H_15 | GGATCCTATCAGATCTATCGGGTACCGTATCGCGGCCGCT(SEQ ID NO: 17) |
| H_16 | CCGCCGCCACCGAATTCCATATGGAAGCGGCCGCGATACG(SEQ ID NO: 18) |
| H_17 | ATTCGGTGGCGGCGGCAGCGGCGGTGGTGGCAGCGAAGAA(SEQ ID NO: 19) |
| H_18 | TCACATAGCTCACAACCAGGTCTTCTTCGCTGCCACCACC(SEQ ID NO: 20) |
| H_19 | CCTGGTTGTGAGCTATGTGAACACCAATATGGGCCTGAAG(SEQ ID NO: 21) |
| H_20 | AACCACAGCAGCTGACGAAACTTCAGGCCCATATTGGTGT(SEQ ID NO: 22) |
| H_21 | TCGTCAGCTGCTGTGGTTTCATATTAGCTGCCTGACCTTT(SEQ ID NO: 23) |
| H_22 | AATCACGGTTTCGCGGCCAAAGGTCAGGCAGCTAATATGA(SEQ ID NO: 24) |
| H_23 | GCCGCGAAACCGTGATTGAATACCTGGTGAGCTTTGGCGT(SEQ ID NO: 25) |
| H_24 | CGCCGGTGGGGTACGAATCCACACGCCAAAGCTCACCAGG(SEQ ID NO: 26) |
| H_25 | CGTACCCCACCGGCGTATCGTCCGCCGAATGCGCCAATTC(SEQ ID NO: 27) |
| H_26 | GTCGTTTCCGGCAGGGTGCTCAGAATTGGCGCATTCGGCG(SEQ ID NO: 28) |
| H_27 | ACCCTGCCGGAAACGACCGTTTAAGAGCTCCGTCGACAAG(SEQ ID NO: 29) |
| H_28 | CCG CTCGAGTGCGGCCGCAAGCTTGTCGACGGAGCTCTTAAA(SEQ ID NO: 30) |

5 μl of each of the synthesized primers H_01 to H_28 were taken (with the concentration of 25 μM/L) and mixed. Such mixed primers were used as template, and the first round of PCR amplification was conducted under the catalysis of PFU enzyme (ShenNengBoCai co. ltd., Shanghai, China) The PCR conditions were as: 94° C., 2 min; 30 cycles (94° C., 30 s; 60° C., 30 s; 72° C., 1 min); 72° C., 10 min; 10° C., 10 min. 2 μl of the PCR product of the first round was then taken as template, and primers H_01 and H_28 (with the concentration of 25 μM/L) were used for conducting the amplification, with the amplification conditions as set forth above. 1.5% agarose gel electrophoresis was performed, and the target fragments (having the fragment of the above mentioned optimized HBC nucleotide sequence) were recovered.

Figure 3:
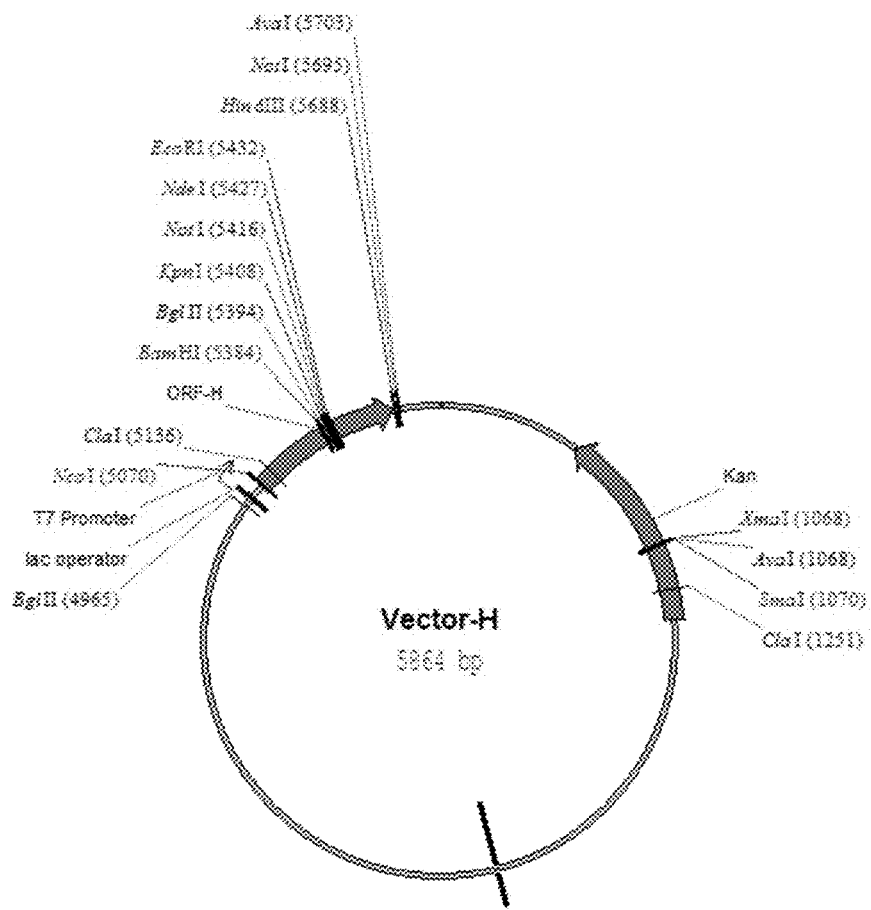
FIG. 3: the structure of H vector.

The above obtained HBc DNA was digested by NcoI/XhoI (NEB, MA) for 4 h. The digested products were recovered (DNA recovery kit obtained from TIANGEN Biotech (Beijing) co., ltd), ligated onto digested pET28a vector (Novagen, Merck, Germany) by T4 ligase (NEB, MA), and then transformed into TOP10 competent cells. After the clones grown the next day were verified by colony PCR and BamHI/EcoRI (NEB, MA) digestion, 3 of the positive clones were picked for sequencing, and the sequencing primers were T7 promoter primers (Biosune, co. ltd. Shanghai, China) The new vector that was sequenced and successfully identified was named as H vector, the structure of which is shown in FIG. 3.

Example 2

The Design, Expression and Purification of Desmin Immunization Antigen

The Desmin protein has an identity of 97% with corresponding mouse protein, and the full length amino acid sequence of Desmin is:

(SEQ ID NO: 31)

```
  1 MSQAYSSSQR VSSYRRTFGG APGFPLGSPL SSPVFPRAGF GSKGSSSSVT SRVYQVSRTS

61 GGAGGLGSLR ASRLGTTRTP SSYGAGELLD FSLADAVNQE FLTTRTNEKV ELQELNDRFA

121 NYIEKVRFLE QQNAALAAEV NRLKGREPTR VAELYEEELR ELRRQVEVLT

NQRARVDVER

181 DNLLDDLQRL KAKLQEEIQL KEEAENNLAA FRADVDAATL ARIDLERRIE SLNEEIAFLK

241 KVHEEEIREL QAQLQEQQVQ VEMDMSKPDL TAALRDIRAQ YETIAAKNIS

EAEEWYKSKV
```

-continued
301 SDLTQAANKN NDALRQAKQE MMEYRHQIQS YTCEIDALKG TNDSLMRQMR ELEDRFASEA

361 SGYQDNIARL EEEIRHLKDE MARHLREYQD LLNVKMALDV EIATYRKLLE GEESRINLPI

421 QTYSALNFRE TSPEQRGSEV HTKKTVMIKT IETRDGEVVS EATQQQHEVL

Trans-membrane helixes, lysis sites, and signal peptides in the protein sequence were predicted based on several artificial neural networks and hidden Markov analysis, and the results showed that the protein do not have trans-membrane domain or signal peptide, and the distribution of hydrophilic and hydrophobic amino acids was relatively even.

Peptides of 11-12 amino acids were generated according to the design method for tandem polypeptide of immunization antigens mentioned in the Section of Detailed Description of the Invention. For every short peptide, the isoelectric point, accessibility, immunogenicity, hydrophilicity, and specie specificity according to BLAST methods were calculated. When the isoelectric point was larger than 3.5, the weighted average value of the above parameters were calculated for every short peptide (0.2*immunogenicity+ 0.1*accessibility+0.2*hydrophilicity+0.5*specie specificity). These short peptides were sorted according to the weighted average values, and the short peptides having the highest score and with an inter-peptide overlap <3 are selected. 5 linear surface signature peptides with the length of 11-12 amino acids were selected (see table 3), and these peptides were linked using linker GGGGS (SEQ ID NO:158), to form tandem polypeptide of immunization antigens.

According to the searching for said protein, it was discovered that it do not contain trans-membrane structures or signal-peptide. Analysis according to the above principle was performed for the full length protein, and 5 surface signature sequences were determined. The sequence of the finally determined tandem polypeptide of immunization antigens of Desmin H vector was:

(SEQ ID NO: 32)
RETSPEQRGSEV-GGGGS-KVSDLTQAANK-GGGGS-RLKGREPTRVAE
-GGGGS-VEVLTNQRARVD-GGGGS-EESRINLPIQTY.

B Complete Gene Synthesis Method for Tandem Polypeptide of Immunization Antigens After codon optimization, it was determined that the nucleotide sequence (encoding the tandem polypeptide of immunization antigens of SEQ ID NO:32) that needs to be completely synthesized is:

(SEQ ID NO: 38)
GACACggatccCGTGAAACCAGCCCGGAACAGCGTGGCAGCGAA

GTGGGTGGTGGAGGTTCTAAAGTGAGCGATCTGACCCAGGCGGCG

AATAAAGGGGAGGCGGCAGCCGTCTGAAAGGCCGTGAACCGACC

CGTGTGGCGGAAGGTGGGGTGGAAGCGTGGAAGTGCTGACCAAT

CAGCGTGCGCGTGTGGATGGCGGTGGCGGCTCGGAAGAAAGCCGT

ATTAATCTGCCGATTCAGACCTATGgaatttcgTGTC

According to complete gene synthesis method, all together 10 primer sequences were designed, see table 4. The complete gene synthesis method can be seen in Example 1. Briefly, 5 µl of the synthesized primers 1_01 to 1_10 were taken (with the concentration of 25 µM) and mixed. Such mixed primers were used as template, and the first round of PCR amplification was conducted under the catalysis of PFU enzyme (ShenNengBoCai co. ltd., Shanghai, China). The PCR conditions were as: 94° C., 2 min; 30 cycles (94° C., 30 s; 60° C., 30 s; 72° C., 1 min); 72° C., 10 min; 10° C., 10 min. 2 µl of the PCR product of the first round was then taken as template, and primers 1_01 and 1_10 (with the concentration of 25 µM) were used for conducting the amplification, with the amplification conditions as set forth above. 1.5% agarose gel electrophoresis was performed, and the target fragments (i.e. the nucleotide sequence to be completely synthesized) were recovered.

TABLE 3

The selection of tandem polypeptide of immunization antigens

| Peptide sequences | length/ aa | Starting site (based on Genbank: AAF15400.1 amino acid numbering) | Ending site (based on Genbank: AAF15400.1 amino acid numbering) |
| --- | --- | --- | --- |
| RETSPEQRGSEV (SEQ ID NO: 33) | 12 | 429 | 440 |
| KVSDLTQAANK (SEQ ID NO: 34) | 11 | 299 | 309 |
| RLKGREPTRVAE (SEQ ID NO: 35) | 12 | 142 | 153 |
| VEVLTNQRARVD (SEQ ID NO: 36) | 12 | 166 | 177 |
| EESRINLPIQTY (SEQ ID NO: 37) | 12 | 412 | 423 |

TABLE 4

The nucleotide sequences for the complete gene synthesis of immunization antigens

| Primer names | Primer sequences(5'-3') | Nucleotides number of each primer |
|---|---|---|
| 1_01 | GACACggatccCGTGAAACCAGCCCGGAACAGCGTGG(SEQ ID NO: 39) | 37 |
| 1_02 | AGAACCTCCACCACCCACTTCGCTGCCACGCTGTTCCGGG(SEQ ID NO: 40) | 40 |
| 1_03 | TGGGTGGTGGAGGTTCTAAAGTGAGCGATCTGACCCAGGC(SEQ ID NO: 41) | 40 |
| 1_04 | CTGCCGCCTCCCCCTTTATTCGCCGCCTGGGTCAGATCGC(SEQ ID NO: 42) | 40 |
| 1_05 | GGGGGAGGCGGCAGCCGTCTGAAAGGCCGTGAACCGACCC(SEQ ID NO: 43) | 40 |
| 1_06 | CTTCCACCCCCACCTTCCGCCACACGGGTCGGTTCACGGC(SEQ ID NO: 44) | 40 |
| 1_07 | GAAGGTGGGGGTGGAAGCGTGGAAGTGCTGACCAATCAGC(SEQ ID NO: 45) | 40 |
| 1_08 | CACCGCCATCCACACGCGCACGCTGATTGGTCAGCACTTC(SEQ ID NO: 46) | 40 |
| 1_09 | CGTGTGGATGGCGGTGGCGGCTCGGAAGAAAGCCGTATTA(SEQ ID NO: 47) | 40 |
| 1_10 | GACACgaattcATAGGTCTGAATCGGCAGATTAATACGGCTTTCTTCCGAG(SEQ ID NO: 48) | 51 |

Example 3

Expression and Purification of the Tandem Polypeptide of Immunization Antigens The sequence of SEQ ID NO: 38 which was completely synthesized in Example 2 was digested using BamHI/EcoRI, and then was ligated through T4 ligase at room temperature for 2 h with the H vector digested with BamHI/EcoRI and recovered in Example 1. The ligated product was incubated on ice (4° C.) for 0.5 h with Rosetta competent cells (Novagen, Merck, Germany) prepared by $CaCl_2$ method, and was heat-activated at 42° C. for 90 s. The heat-activated bacteria liquid was supplemented with 200 μl-500 μl LB liquid medium with no antibiotics. The composition of the medium was: 10 g/L Tryptone (Oxoid, England), 5 g/L Yeast Extract (Oxoid, England), 10 g/L NaCl (Sinopharm Group, Shanghai, China). The bacteria liquid was then slowly shaked on a 37° C. shaker at 100 rpm for 45 min, and finally was plated on LB plates with corresponding antibiotics. The bacteria plates were cultured in 7° C. incubator overnight.

The next day, the transformed colonies were picked into auto-induction system culture medium, and the composition of the medium was: 10 g/L Tryptone (Oxoid, England), 5 g/L yeast extract (Oxoid, England), 3.3 g/L $(NH_4)_2SO_4$ (Sinopharm Group, Shanghai, China), 6.8 g/L $KH_2PO_4$ (Sinopharm Group, Shanghai, China), 7.1 g/L $Na_2HPO_4$ (Sinopharm Group, Shanghai, China), 0.5 g/L glucose (Sinopharm Group, Shanghai, China), 2.0 g/L a-Lactose (Sinopharm Group, Shanghai, China), 0.15 g/L $MgSO_4$(Sinopharm Group, Shanghai, China). The culture was expressed at 37° C., 250 rpm overnight. The next day, the bacteria liquid was centrifuged (6,000 g, 5 min), the supernatant was discarded, and the pellet was resuspended using lysis buffer (50 mM Tris, 500 mM NaCl, 4M urea, 1 mM PMSF, pH7.4) and was lysed overnight at room temperature.

25 ml (5 times of the column volume) of the lysis buffer was used for pre-equilibration of $Ni^{2+}$-NTA column (Qiagen, Germany), and the column was placed in still for future uses. After centrifugation (15,000 g, 10 min) of the cell lysis liquid, the supernatant was applied on the column and incubated at room temperature for 1 h. After the incubation, the liquid to be lysed naturally flew out from the column, 30 ml washing buffer (4M urea, 50 mM Tris, 500 mM NaCl, 30 mM imidazole, pH 7.4) was used for washing, and finally 5 ml elution buffer (4M urea, 50 mM Tris, 500 mM NaCl, 500 mM imidazole, pH 7.4) was used for eluting and collecting the protein. The eluted protein was dialysed into buffer (phosphate buffer of pH5.8), and the composition of the buffer was: 25.39 g/L $NaH_2PO_4$—$H_2O$ (Sinopharm Group, Shanghai, China), 5.73 g/L $Na_2HPO_4$-$12H_2O$ (Sinopharm Group, Shanghai, China). The buffer was changed twice during the process, and the dialysis was all together performed for 24 h.

1.5 mg polypeptide was obtained after the dialysis, the concentration was 0.3 mg/ml, and the purity was >95%.

Example 4

The Design, Expression and Purification of Detection Antigens

A The Design of Detection Antigens

The information for the polypeptide of immunization antigens of the following 5 proteins including Desmin was collected, and the sequences are in

TABLE 5

Table 5: The design of immunization antigens for proteins

| Protein name | The sequence of the polypeptide of immunization antigens |
|---|---|
| Desmin | RETSPEQRGSEV-GGGGS-KVSDLTQAANK-GGGGS-RLKGREPTRVAE-GGGGS-VEVLTNQRARVD-GGGGS-EESRINLPIQTY(SEQ ID NO: 49) |

TABLE 5-continued

Table 5: The design of immunization antigens for proteins

| Protein name | The sequence of the polypeptide of immunization antigens |
|---|---|
| vimentin | LRPSTSRSLYAS-GGGGS-INETSQHHDDLE-GGGGS-AINTEFKN TRT-GGGGS-EQLKGQGKSRLG-GGGGS-QREEAENTLQSF(SEQ ID NO: 50) |
| CD3g | KKKWNLGSNAKD-GGGGS-DGVRQSRASDK-GGGGS-CKGSQN KSKPL-GGGGS-VKVYDYQEDGSV-GGGGS-EAKNITWFKDGK(SEQ ID NO: 51) |
| CD3e | DKNIGGDEDDK-GGGGS-EEMGGITQTPYK-GGGGS-CYPRGSKP EDA-GGGGS-DHLSLKEFSELE-GGGGS-GQRDLYSGLNQR(SEQ ID NO: 52) |
| CD79a | VQEGNESYQQSC-GGGGS-EDAHFQCPHNSS-GGGGS-RKRWQN EKLGLD-GGGGS-EDISRGLQGTY-GGGGS-GPGEDPNGTLII(SEQ ID NO: 53) |

The sequences of corresponding detection antigens were determined according to the design strategy of detection antigens. The main strategy was to respectively name 5 surface signature peptide sequences of each protein as ABCDE according to the 5 sequences of the polypeptide of immunization antigens of 5 proteins, and then combined the A epitopes of each protein to get detection antigen A. Similarly detection antigens B-E were obtained. The specific information for the detection antigens was shown in Table 6.

TABLE 6

The amino acids sequences for detection antigens

| | |
|---|---|
| Detection antigen A | RETSPEQRGSEV-LRPSTSRSLYAS-KKKWNLGSNAKD-DKNIGGDEDDK-VQEGNESYQQSC(SEQ ID NO: 54) |
| Detection antigen B | KVSDLTQAANKN-INETSQHHDDLE-DGVRQSRASDK-EEMGGITQTPYK-EDAHFQCPHNSS(SEQ ID NO: 55) |
| Detection antigen C | RLKGREPTRVAE-AINTEFKNTRT-CKGSQNKSKPL-CYPRGSKPEDA-RKRWQNEKLGLD(SEQ ID NO: 56) |
| Detection antigen D | VEVLTNQRARVD-EQLKGQGKSRLG-VKVYDYQEDGSV-DHLSLKEFSELE-EDISRGLQGTY(SEQ ID NO: 57) |
| Detection antigen E | EESRINLPIQTY-QREEAENTLQSF-EAKNITWFKDGK-GQRDLYSGLNQR-GPGEDPNGTLII (SEQ ID NO: 58) |

B Complete Gene Synthesis of the Detection Antigens

DNA Works software was used for codon optimization of the sequences of the designed detection antigens in Table 6, and the primers for synthesizing the optimized nucleotide sequences of the detection antigens were synthesized by SBSGENE co. ltd. (Shanghai, China) The nucleotide sequences of the optimized 5 detection antigens were:

```
Detection antigen A:
                                    (SEQ ID NO: 59)
CGTGAAACCAGCCCGGAACAGCGTGGCAGCGAAGTGCTGCGTCCG

AGCACCAGCCGTAGCCTGTATGCGAGCAAGAAAAAATGGAATCTG
```

-continued

```
GGCAGCAATGCGAAAGATGACAAAAACATTGGCGGCGACGAGGAT

GATAAGGTGCAGGAAGGCAACGAAAGCTATCAGCAAAGCTGC

Detection antigen B:
                                    (SEQ ID NO: 60)
AAAGTGTCAGACCTGACCCAGGCGGCGAATAAGAACATTAACGAA

ACCAGCCAGCATCACGATGATCTGGAAGATGGCGTGCGTCAGAGC

CGTGCGAGCGATAAAGAAGAAATGGGCGGCATTACCCAGACCCCG

TATAAAGAGGATGCACATTTTCAGTGCCCGCATAATAGCAGC

Detection antigen C:
                                    (SEQ ID NO: 61)
CGTCTGAAAGGCCGTGAACCGACCCGTGTGGCGGAAGCGATTAAC

ACCGAATTTAAGAATACCCGTACCTGCAAAGGCAGCCAGAATAAA

TCGAAACCGCTGTGCTATCCGCGTGGCAGCAAACCGGAAGATGCG

CGTAAACGGTGGCAGAATGAAAAACTGGGCCTGGAT

Detection antigen D:
                                    (SEQ ID NO: 62)
GTGGAAGTGCTGACCAATCAGCGTGCGCGTGTGGATGAACAGCTG

AAAGGCCAGGGCAAAAGCCGTCTGGGTGTGAAAGTGTATGATTAT

CAGGAAGATGGCAGCGTGGATCATCTGAGCCTGAAAGAATTTAGC

GAACTGGAAGAAGACATCAGCCGTGGGCTGCAGGGCACCTAT

Detection antigen E:
                                    (SEQ ID NO: 63)
GAAGAAAGTCGTATTAATCTGCCGATTCAGACCTATCAGCGTGAGG

AAGCGGAAAATACCCTGCAGTCGTTTGAAGCGAAAAACATTACCT

GGTTCAAAGATGGCAAAGGCCAGCGGGATCTGTATAGCGGCCTGA

ACCAACGTGGTCCGGGCGAAGATCCGAATGGCACCCTGATTATT
```

According to the nucleotide sequences of the detection antigens and the BamH I and EcoR I digestions sites introduced into the synthesized sequences, 8 primers were respectively designed, and the sequences thereof were in Tables 7-11. The complete gene synthesis method was the same to Example 1.

5 μl of the synthesized primers 2_01 to 2_10 for detection antigen A were taken (with the concentration of 25 μM) and mixed. Such mixed primers were used as template, and the first round of PCR amplification was conducted under the catalysis of PFU enzyme (ShenNengBoCai co. ltd., Shanghai, China). The PCR conditions were as: 94° C., 2 min; 30 cycles (94° C., 30 s; 60° C., 30 s; 72° C., 1 min); 72° C., 10 min; 10° C., 10 min. 2 µl of the PCR product of the first round was then taken as template, and primers 2_01 and 2_10 (with the concentration of 25 µM) were used for conducting the amplification, with the amplification conditions as set forth above. 1.5% agarose gel electrophoresis was performed, and the target fragments (i.e. the nucleotide sequence to be completely synthesized) were recovered.

The complete gene synthesis methods for detection antigens B-E were completely the same to that of detection antigen A, only with the exception that the sequences of the primers were different.

After being double-digested with the two enzymes BamH I and EcoR I, the completely synthesized nucleotide sequences of the detection antigens were ligated into pET32a vectors (Novagen, Merck, Germany) digested by the same enzymes.

TABLE 7 the primers for the complete gene synthesis of the detection antigen A

| Primer names | Primer sequences (5'-3') | Nucleotides number of each primer |
|---|---|---|
| 2_01 | GACACggatccCGTGAAACCAGCCCGGAACAGCGTGGCA (SEQ ID NO: 64) | 39 |
| 2_02 | CTGGTGCTCGGACGCAGCACTTCGCTGCCACGCTGTTCCG (SEQ ID NO: 65) | 40 |
| 2_03 | GCGTCCGAGCACCAGCCGTAGCCTGTATGCGAGCAAGAAA (SEQ ID NO: 66) | 40 |
| 2_04 | ATTGCTGCCCAGATTCCATTTTTTCTTGCTCGCATACAGG (SEQ ID NO: 67) | 40 |
| 2_05 | TGGAATCTGGGCAGCAATGCGAAAGATGACAAAAACATTG (SEQ ID NO: 68) | 40 |
| 2_06 | TATCATCCTCGTCGCCGCCAATGTTTTTGTCATCTTTCGC (SEQ ID NO: 69) | 40 |
| 2_07 | CGGCGACGAGGATGATAAGGTGCAGGAAGGCAACGAAAGC (SEQ ID NO: 70) | 40 |
| 2_08 | GACACgaattcGCAGCTTTGCTGATAGCTTTCGTTGCCTTCCTG (SEQ ID NO: 71) | 44 |

TABLE 8 the primers for the complete gene synthesis of the detection antigen B

| Primer names | Primer sequences (5'-3') | Nucleotides number of each primer |
|---|---|---|
| 3_01 | GACACggatccAAAGTGTCAGACCTGACCCAGGCGGCGAATAA (SEQ ID NO: 72) | 43 |
| 3_02 | TGCTGGCTGGTTTCGTTAATGTTCTTATTCGCCGCCTGGG (SEQ ID NO: 73) | 40 |
| 3_03 | AACGAAACCAGCCAGCATCACGATGATCTGGAAGATGGCG (SEQ ID NO: 74) | 40 |
| 3_04 | CGCTCGCACGGCTCTGACGCACGCCATCTTCCAGATCATC (SEQ ID NO: 75) | 40 |
| 3_05 | GAGCCGTGCGAGCGATAAAGAAGAAATGGGCGGCATTACC (SEQ ID NO: 76) | 40 |
| 3_06 | CATCCTCTTTATACGGGGTCTGGGTAATGCCGCCCATTTC (SEQ ID NO: 77) | 40 |
| 3_07 | AGACCCCGTATAAAGAGGATGCACATTTTCAGTGCCCGCA (SEQ ID NO: 78) | 40 |
| 3_08 | GACACgaattcGCTGCTATTATGCGGGCACTGAAAATG (SEQ ID NO: 79) | 38 |

TABLE 9

The primers for the complete gene synthesis of the detection antigen C

| Primer names | Primer sequences (5'-3') | Nucleotides number of each primer |
|---|---|---|
| 4_01 | GACACggatccCGTCTGAAAGGCCGTGAACCGAC (SEQ ID NO: 80) | 34 |
| 4_02 | TGTTAATCGCTTCCGCCACACGGGTCGGTTCACGGCCTTT (SEQ ID NO: 81) | 40 |
| 4_03 | TGGCGGAAGCGATTAACACCGAATTTAAGAATACCCGTAC (SEQ ID NO: 82) | 40 |
| 4_04 | TTCTGGCTGCCTTTGCAGGTACGGGTATTCTTAAATTCGG (SEQ ID NO: 83) | 40 |
| 4_05 | TGCAAAGGCAGCCAGAATAAATCGAAACCGCTGTGCTATC (SEQ ID NO: 84) | 40 |
| 4_06 | TCTTCCGGTTTGCTGCCACGCGGATAGCACAGCGGTTTCG (SEQ ID NO: 85) | 40 |
| 4_07 | GGCAGCAAACCGGAAGATGCGCGTAAACGGTGGCAGAATG (SEQ ID NO: 86) | 40 |
| 4_08 | GACACgaattcATCCAGGCCCAGTTTTTCATTCTGCCACCGTTTACG (SEQ ID NO: 87) | 47 |

TABLE 10

The primers for the complete gene synthesis of the detection antigen D

| Primer names | Primer sequences (5'-3') | Nucleotides number of each primer |
|---|---|---|
| 5_01 | GACACggatccGTGGAAGTGCTGACCAATCAGCGTGCGCGTG (SEQ ID NO: 88) | 42 |
| 5_02 | GCCCTGGCCTTTCAGCTGTTCATCCACACGCGCACGCTGA (SEQ ID NO: 89) | 40 |
| 5_03 | GCTGAAAGGCCAGGGCAAAAGCCGTCTGGGTGTGAAAGTG (SEQ ID NO: 90) | 40 |
| 5_04 | TGCCATCTTCCTGATAATCATACACTTTCACACCCAGACG (SEQ ID NO: 91) | 40 |
| 5_05 | ATGATTATCAGGAAGATGGCAGCGTGGATCATCTGAGCCT (SEQ ID NO: 92) | 40 |
| 5_06 | TTCCAGTTCGCTAAATTCTTTCAGGCTCAGATGATCCACG (SEQ ID NO: 93) | 40 |
| 5_07 | GAAAGAATTTAGCGAACTGGAAGAAGACATCAGCCGTGGG (SEQ ID NO: 94) | 40 |
| 5_08 | GACACgaattcATAGGTGCCCTGCAGCCCACGGCTGATGTCTT (SEQ ID NO: 95) | 43 |

TABLE 11

The primers for the complete gene synthesis of the detection antigen E

| Primer names | Primer sequences (5'-3') | Nucleotides number of each primer |
|---|---|---|
| 6_01 | GACACggatccGAAGAAAGTC

TABLE 11-continued

The primers for the complete gene synthesis of the detection antigen E

| Primer names | Primer sequences (5'-3') | Nucleotides number of each primer |
|---|---|---|
| 6_02 | CCGCTTCCTCACGCTGATAGGTCTGAATCGGCAGATTAAT (SEQ ID NO: 97) | 40 |
| 6_03 | CAGCGTGAGGAAGCGGAAAATACCCTGCAGTCGTTTGAAG (SEQ ID NO: 98) | 40 |
| 6_04 | TTGAACCAGGTAATGTTTTTCGCTTCAAACGACTGCAGGG (SEQ ID NO: 99) | 40 |
| 6_05 | CGAAAAACATTACCTGGTTCAAAGATGGCAAAGGCCAGCG (SEQ ID NO: 100) | 40 |
| 6_06 | TTGGTTCAGGCCGCTATACAGATCCCGCTGGCCTTTGCCA (SEQ ID NO: 101) | 40 |
| 6_07 | ATAGCGGCCTGAACCAACGTGGTCCGGGCGAAGATCCGAA (SEQ ID NO: 102) | 40 |
| 6_08 | GACACgaattcAATAATCAGGGTGCCATTCGGATCTTCGCCCG (SEQ ID NO: 103) | 43 |

G The Expression and Purification of the Detection Antigens

The above DNA sequences of the 5 corresponding detection antigens that were prepared by complete gene synthesis were integrated into PET32a vectors (Novagen) through BamHI/EcoRI restriction sites, and then 5 plasmids were obtained.

The composition of auto-induction system culture medium was: 10 g/L Tryptone (Oxoid, England), 5 g/L yeast extract (Oxoid, England), 3.3 g/L $(NH_4)_2SO_4$ (Sinopharm Group, Shanghai, China), 6.8 g/L $KH_2PO_4$ (Sinopharm Group, Shanghai, China), 7.1 g/L $Na_2HPO_4$ (Sinopharm Group, Shanghai, China), 0.5 g/L glucose (Sinopharm Group, Shanghai, China), 2.0 g/L a-Lactose (Sinopharm Group, Shanghai, China), 0.15 g/L $MgSO_4$ (Sinopharm Group, Shanghai, China).

Said plasmids were respectively transformed into Rosseta strains. Transformed colonies were picked into auto-induction system culture medium (see example 3), and were expressed at 37° C. 250 rpm overnight. The next day, the bacteria liquid was centrifuged (6,000 g, 5 min), and the supernatant was discarded. The pellet was resuspended using lysis buffer (50 mM Tris, 500 mM NaCl, 4M urea, protease inhibitor, pH 7.4) and was lysed overnight.

25 ml (5 times of the column volume) of the lysis buffer was used for pre-equilibration of $Ni^{2+}$-NTA column, and the column was placed in still for future uses. After centrifugation (15,000 g, 10 min) of the cell lysis liquid, the supernatant was applied on the column and incubated at room temperature for 1 h. After the incubation, the liquid to be lysed naturally flew out from the column, 30 ml washing buffer (4M urea, 50 mM Tris, 500 mM NaCl, 30 mM imidazole, pH 7.4) was used for washing, and finally 5 ml elution buffer (4M urea, 50 mM Tris, 500 mM NaCl, 500 mM imidazole, pH 7.4) was used for eluting and collecting the protein.

The purified amount of detection antigen A was 0.8 mg, with the purity of 80%; the purified amount of detection antigen B was 0.65 mg, with the purity of 90%; the purified amount of detection antigen C was 1.2 mg, with the purity of 85%; the purified amount of detection antigen D was 1.5 mg, with the purity of 75%; the purified amount of detection antigen E was 0.9 mg, with the purity of 95%.

Example 5

Preparation of Monoclonal Antibodies

A Immunization Method

Oligonucleotide adjuvant: 50 μl aluminum adjuvant (Thermo Fisher, USA)+1 μg DNA adjuvant, and the sequence thereof was tccatgacgttcctgacgtT (SEQ ID NO: 104), wherein the bases in lower case were sites that need thio-modifications, the oligonucleotide was synthesized by SBSGENE co. ltd. (Shanghai, China).

As for protein antigens in the experiments, the dosage for each mouse and each immunization can be any dosage between 2-200 μg, and the time interval for each immunization can be 2-14 days. The immunization method and dosages for the synthesized protein Desmin (SEQ ID NO:32) were as follows.

Immunization method: 3 Balb/c mice, 8-10 weeks old, body weight 18-20 g. 20 μg antigen was completely emulsified with Freund's complete adjuvant (Sigma), and the immunization sites were hind foot palm, tail end, and front leg armpit as well as inguen, wherein about 50 μL was applied for each site. 20 μg antigen was completely mixed with the oligonucleotide adjuvant, and was then used to immunize the mice at hind leg muscle, wherein 50-100 μL was applied for each site.

On the eighth day, 10 μg antigen was taken and completely emulsified with Freund's complete adjuvant (Sigma), which was used to immunize the mice at front leg armpit and inguen, wherein 50-100 μL was applied for each site. 20 μg antigen was completely mixed with the oligonucleotide adjuvant, and was then used to immunize the mice at hind leg muscle, wherein 50-100 μL was applied for each site.

On the twelfth day, 10 μg antigen was completely mixed with the oligonucleotide adjuvant, and was then used to immunize the mice at hind leg muscle.

On the fourteenth day, blood was taken from eyepit of the mice, and ELISA method was used to examine the serum titer, wherein the serum titers of the mice were all higher than 1:32000.

B Cell Fusion and Screening

The preparation of relevant media: the basic medium used was 1640 medium (Thermo, USA), and the serum concentration in the complete medium was 15%, wherein the serum was purchased from Biowest, Spain, and HAT and HT stock solutions were purchased from Sigma, Germany.

On the fifteenth day, the mice were sacrificed by cervical dislocation. The lymph-node cells of 2 mice were taken for the fusion with SP20 cells (ATCC, USA), the cells were suspended (final cell density was about $10^6$/ml), and then were plated on 4 384 plates, with 80 μL for each well. The cell plates were cultured at 37° C., 5% $CO_2$ for 6 days, and then were completely changed to HT complete medium. 8 days after the fusion, 10 μL cell supernatant was taken, and diluted 5 times, for ELISA assay.

The immunogen (H carrier protein carrying the polypeptide sequence of SEQ ID NO:32) was diluted to 1 μg/ml using 0.01M $Na_2CO_3$/$NaHCO_3$ buffer. 100 μL was added into each well, and coating was performed at 4 degree overnight. The plates were swung to clean the solution therein, and were washed by PBST for 3 times, with 250 μL/well. 5% milk was used for blocking at 37° C. for 1 h, and the plates were swung to clean the solution therein, and were washed by PBST for 3 times, with 250 μL/well. The cell fusion plate supernatant was taken, 20 μL for each well, 80 μL of 5% milk was supplemented, and the plates were then incubated at 37° C. for 1 h. The plates were swung to clean the solution therein, and were washed by PBST for 3 times, with 250 μL/well. 100 μL of HRP labeled caprice-anti-mouse antibody (Abmart, 1:8000) was added into each well, and the plates were then incubated at 37° C. for 1 h. The plates were swung to clean the solution therein, and were washed by PBST for 3 times, with 250 μL/well. Horse radish peroxidase substrate TMB (Sigma) solution was added, and the plates were then incubated at 37° C. for 15 min 50 μL of 2M $H_2SO_4$ solution was added into each well to terminate the reaction, and the absorption at 450 nm was read.

The detection antigens A-E were respectively diluted to 1 μg/ml using 0.01M $Na_2CO_3$/$NaHCO_3$ buffer, and 100 μL was added into each well, and coating was performed at 4 degree overnight. The plates were swung to clean the solution therein, and were washed by PBST for 3 times, with 250 μL/well. 5% milk was used for blocking at 37° C. for 1 h, and the plates were swung to clean the solution therein, and were washed by PBST for 3 times, with 250 μL/well.

50 μL of supernatant was taken from wells that were preliminarily identified as positive, 200 μL of 5% milk was supplemented, and 50 μL was respectively taken and added into the ELISA plates for detection antigens 1-5. The plates were incubated at 37° C. for 1 h, swung to clean the solution therein, and then washed by PBST for 3 times, with 250 μL/well. 100 μL of HRP labeled caprice-anti-mouse antibody (Abmart, 1:8000) was added into each well, and the plates were then incubated at 37° C. for 1 h. The plates were swung to clean the solution therein, and were washed by PBST for 3 times, with 250 μL/well. Horse radish peroxidase substrate TMB (Sigma) solution was added, and the plates were then incubated at 37° C. for 15 min. 50 μL of 2M $H_2SO_4$ solution was added into each well to terminate the reaction, and the absorption at 450 nm was read.

The data for the epitopes screening were shown in table 12. The wells that were positive to different detection antigens were just the antibodies against different antigen epitopes, and the screening results can be seen in table 13. 5 polypeptide fragments of SEQ ID NO:32 were named as epitopes A, B, C, D, E according to the sequence from N-terminus to C-terminus.

Since each detection antigen only carried one protein surface signature peptide related to the immunization antigen, every detection antigen positive clone (OD larger than 0.5), was directed to the first polypeptide of the immunization antigen (the polypeptide of SEQ ID NO:32). For example, the well of detection antigen A4 was positive for ELISA detection (see table 12, OD=2.092), since the detection antigen A carried the sequence of RETSPEQRGSEV—the first surface linear signature peptide of SEQ ID NO:32 polypeptide (see tables 5 and 6), it can be determined from such results that the recognition epitope of the antibody clone in A4 well was the first surface linear signature peptide—RETSPEQRGSEV. Such strategy was used to determine the sequences recognized by different positive wells.

TABLE 12

The epitopes screening results for the wells of fusion positive clone

| Detection antigens | 1 | 2 | 3 | 4 | 5 | 6 | 7 | 8 | 9 | 10 | 11 | 12 | |
|---|---|---|---|---|---|---|---|---|---|---|---|---|---|
| Detection antigen A | 0.058 | 0.077 | 0.132 | 2.092 | 0.089 | 0.066 | 0.085 | 0.069 | 0.073 | 0.084 | 2.148 | 0.117 | A |
|  | 0.08 | 0.071 | 0.074 | 0.08 | 0.072 | 0.089 | 0.106 | 0.089 | 1.942 | 0.093 | 0.107 | 0.088 | B |
| Detection antigen B | 0.087 | 2.595 | 0.062 | 0.066 | 0.085 | 0.069 | 0.084 | 2.045 | 0.089 | 0.088 | 0.081 | 0.069 | C |
|  | 0.074 | 2.181 | 0.061 | 0.072 | 0.089 | 1.942 | 0.093 | 0.093 | 0.107 | 0.065 | 0.063 | 0.063 | D |
| Detection antigen C | 0.062 | 0.132 | 2.595 | 0.103 | 0.085 | 0.066 | 0.101 | 0.093 | 0.13 | 2.027 | 0.058 | 0.063 | E |
|  | 0.07 | 0.074 | 0.066 | 0.13 | 0.092 | 0.069 | 2.075 | 0.082 | 0.075 | 0.125 | 0.058 | 0.058 | F |
| Detection antigen D | 0.068 | 0.068 | 0.136 | 0.076 | 0.06 | 1.994 | 0.075 | 0.139 | 1.923 | 0.067 | 0.053 | 0.070 | G |
|  | 0.085 | 0.062 | 1.575 | 0.059 | 0.066 | 0.083 | 0.067 | 0.064 | 0.076 | 0.072 | 0.064 | 0.080 | H |
| Detection antigen E | 0.076 | 0.061 | 0.086 | 0.06 | 0.067 | 0.09 | 0.064 | 0.101 | 0.106 | 0.077 | 0.073 | 0.068 | I |
|  | 0.054 | 0.066 | 0.065 | 0.073 | 0.073 | 0.062 | 0.083 | 0.07 | 0.065 | 0.068 | 0.062 | 0.066 | J |

TABLE 13

The epitopes screening results and corresponding clone number

| Epitopes | The sequences of epitopes | Number of cell strains |
|---|---|---|
| A | RETSPEQRGSEV (SEQ ID NO: 105) | 3 |
| B | KVSDLTQAAN (SEQ ID NO: 106) | 4 |
| C | RLKGREPTRVAE (SEQ ID NO: 107) | 3 |
| D | VEVLTNQRARVD (SEQ ID NO: 108) | 3 |
| E | EESRINLPIQTY (SEQ ID NO: 109) | 0 |

2 positive wells of each epitopes were respectively picked to conduct limiting dilution for sub-cloning. After 3 rounds of sub-clonings, 10 strains of stable hybridoma cell strains were obtained, and corresponding cell strain culture supernatants were collected for the antibody verification in Example 6. These cell strains were respectively directed to the 4 polypeptide epitopes (SEQ ID NO: 105-108) of Desmin, wherein 7 cell strains were identified as having an affinity KD lower than 10 nM.

Example 6

The Data for Antibody Verification

A The Experiment Procedure of Western Blotting

C2C12 cells (ATCC, USA) were lysed with RIPA buffer (50 mM Tris pH7.4, 150 mM NaCl, 1% Triton-X-100, 1% sodium deoxycholate, 0.1% SDS lysis buffer) containing protease inhibitor (Roche), quantified by BCA (ShenNeng-BoCai co. ltd.), and diluted by 5× loading buffer. After 10 minutes denaturation at 100° C., 20-30 ng was loaded for each lane, and 10% SDS-PAGE gel electrophoresis was performed. After PVDF membrane transfer, 5% skimmed milk was used for blocking for 1 h. The supernatant of monoclonal cell strain against Desmin (the cell culture supernatant of the cell strain selected in Example 5) 1:5 was added, and then incubation at room temperature was conducted for 1 hour. 1×PBST was used for washing 3×5 min. The secondary antibody-HRP coupled anti-mouse IgG (Abmart, M21001 S) was added at 1:5000, and then incubation at room temperature was conducted for 30 min. 1×PBST was used for washing 3×5 min. ECL Plus (Amersham, USA) was used for the detection.

B The Experiment Procedure of Immuno-Fluorescence (IF)

5×10³ BHK cells (ATCC, USA) were inoculated on a cell slide (SUPER GRADE MICROSCOPE SLIDES) and cultured at 37° C. overnight, after being fixed with chilled methanol (−20° C.) for 15 min, washed with 1×PBS for 2×3 min, and blocked with 1% BSA at room temperature for 1 h, they were then incubated at room temperature for 1 hour with the addition of 1:1 supernatant of monoclonal antibody cell strain culture as primary antibody, and washed with 1×PBST for 3×5 min; they were incubated at room temperature for 1 hour with the addition of secondary antibody anti-mouse Dylight 549 (Abcam) at 1:400 and DAPI at 1:4000, washed with 1×PBST for 3×5 min, and then examined with fluorescence microscope (Olympus) with a picture being taken.

Figure 4:
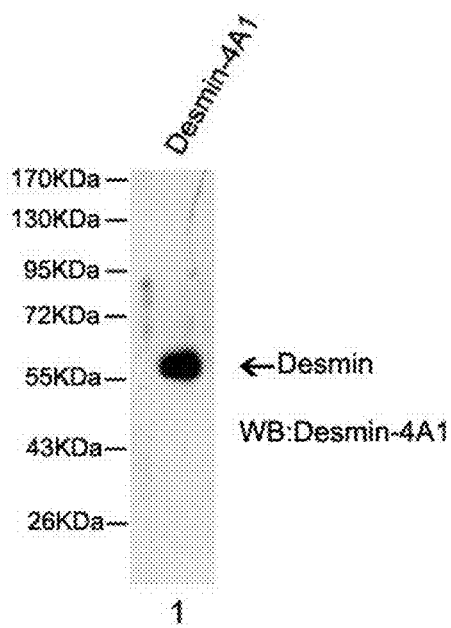
FIG. 4: Western result for the verification of 4A1 antibody. C2C12 cells were lysed with RIPA buffer (50 mM Tris pH7.4, 150 mM NaCl, 1% Triton-X-100, 1% sodium deoxycholate, 0.1% SDS lysis buffer) containing protease inhibitor (Roche), electrophoresed with SDS-PAGE, and then transferred to PVDF membrane; 1:5 diluted supernatant of monoclonal antibody cell strain culture was added, ECL Plus (Amersham) was used for the examination. WB: Western blotting.
Figure 5:
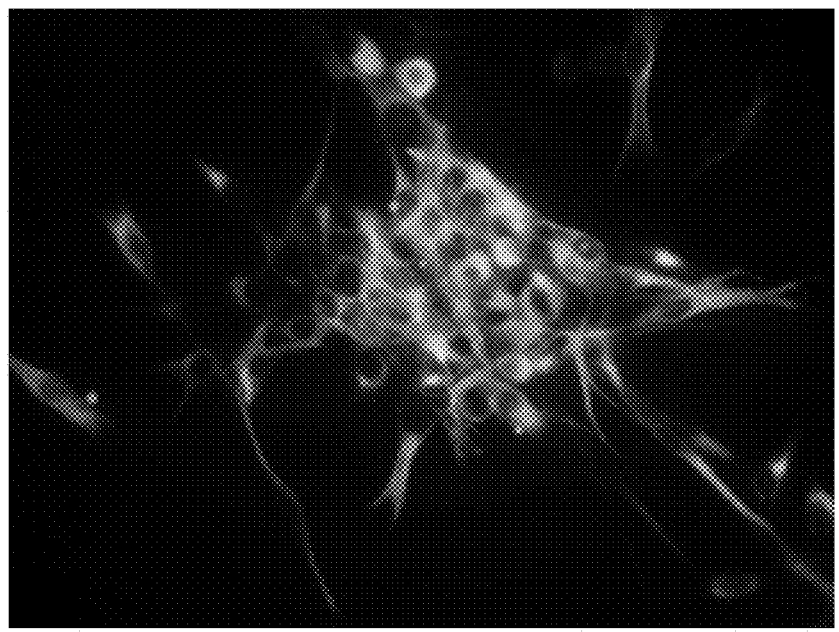
FIG. 5: IF verification data for 4A1 antibody. $5 \times 10^3$ BHK cells were inoculated on a cell slide and cultured at 37° C. overnight, after being fixed with chilled methanol (−20° C.) for 15 min, washed with 1×PBS for 2×3 min, and blocked with 1% BSA at room temperature for 1 h, they were then incubated at room temperature for 1 hour with the addition of 1:1 supernatant of monoclonal antibody cell strain culture, and washed; they were incubated at room temperature for 1 hour with the addition of secondary antibody anti-mouse Dylight 549 (Abcam) at 1:400 and DAPI at 1:4000, washed, and then examined with fluorescence microscope (Olympus) with a picture being taken.

The antibodies against different epitopes were verified by Western. The 7 cell strains obtained in Example 5 can specifically recognize endogenous Desmin of C2C12 cell line, wherein the antibody 4A1 produced by the cell strain named 4A1 (deposited in China Center for Type Culture Collection (CCTCC) on Jan. 28, 2011, with the deposition No. CCTCC C201107) had the best affinity and specificity, and favorite results were obtained in both Western blotting and immuno-fluorescence (see, FIGS. 4 and 5).

Example 7

Preparation of Domain-Specific Antibodies of Membrane Receptor Protein GPR116

A The Selection of Protein Surface Signature Domain:

GPR116 protein is a membrane receptor protein, the specie thereof is human, and the NCBI No. thereof is NP_001091988.1. The full length protein is as following:

(SEQ ID NO: 110)

```
  1  MKSPRRTTLC LMFIVIYSSK AALNWNYEST IHPLSLHEHE
     PAGEEALRQK RAVATKSPTA

61  EEYTVNIEIS FENASFLDPI KAYLNSLSFP IHGNNTDQIT
     DILSINVTTV CRPAGNEIWC

121  SCETGYGWPR ERCLHNLICQ ERDVFLPGHH CSCLKELPPN
     GPFCLLQEDV TLNMRVRLNV

181  GFQEDLMNTS SALYRSYKTD LETAFRKGYG ILPGFKGVTV
     TGFKSGSVVV TYEVKTTPPS

241  LELIHKANEQ VVQSLNQTYK MDYNSFQAVT INESNFFVTP
     EIIFEGDTVS LVCEKEVLSS

301  NVSWRYEEQQ LEIQNSSRFS IYTALFNNMT SVSKLTIHNI
     TPGDAGEYVC KLILDIFEYE

361  CKKKIDVMPI QILANEEMKV MCDNNPVSLN CCSQGNVNWS
     KVEWKQEGKI NIPGTPETDI

421  DSSCSRYTLK ADGTQCPSGS SGTTVIYTCE FISAYGARGS
     ANIKVTFISV ANLTITPDPI

481  SVSEGQNFSI KCISDVSNYD EVYWNTSAGI KIYQRFYTTR
     RYLDGAESVL TVKTSTREWN

541  GTYHCIFRYK NSYSIATKDV IVHPLPLKLN IMVDPLEATV
     SCSGSHHIKC CIEEDGDYKV

601  TFHTGSSSLP AAKEVNKKQV CYKHNFNASS VSWCSKTVDV
     CCHFTNAANN SVWSPSMKLN
```

```
661   LVPGENITCQ  DPVIGVGEPG  KVIQKLCRFS  NVPSSPESPI
      GGTITYKCVG  SQWEEKRNDC

721   ISAPINSLLQ  MAKALIKSPS  QDEMLPTYLK  DLSISIDKAE
      HEISSSPGSL  GAIINILDLL

781   STVPTQVNSE  MMTHVLSTVN  VILGKPVLNT  WKVLQQQWTN
      QSSQLLHSVE  RFSQALQSGD

841   SPPLSFSQTN  VQMSSMVIKS  SHPETYQQRF  VFPYFDLWGN
      VVIDKSYLEN  LQSDSSIVTM

901   AFPTLQAILA  QDIQENNFAE  SLVMTTTVSH  NTTMPFRISM
      TFKNNSPSGG  ETKCVFWNFR

961   LANNTGGWDS  SGCYVEEGDG  DNVTCICDHL  TSFSILMSPD
      SPDPSSLLGI  LLDIISYVGV

1021  GFSILSLAAC  LVVEAVVWKS  VTKNRTSYMR  HTCIVNIAAS
      LLVANTWFIV  VAAIQDNRYI

1081  LCKTACVAAT  FFIHFFYLSV  FFWMLTLGLM  LFYRLVFILH
      ETSRSTQKAI  AFCLGYGCPL

1141  AISVITLGAT  QPREVYTRKN  VCWLNWEDTK  ALLAFAIPAL
      IIVVVNITIT  IVVITKILRP

1201  SIGDKPCKQE  KSSLFQISKS  IGVLTPLLGL  TWGFGLTTVF
      PGTNLVFHII  FAILNVFQGL

1261  FILLFGCLWD  LKVQEALLNK  FSLSRWSSQH  SKSTSLGSST
      PVFSMSSPIS  RRFNNLFGKT

1321  GTYNVSTPEA  TSSSLENSSS  ASSLLN
```

Protein surface signature domain was predicted according to http colon slash slash pfam dot sanger dot ac dot uk slash search slash sequence, and the protein fragment of the amino acid residues at positions 166-307 was used for constructing immunization antigen and detection antigen, wherein the fragment of the amino acid residues at positions 166-307 comprised two important domains.

B Amplification of the Target Fragment

The forward primer: CGCGGATCCCTTCAGGAAGAT-GTTACCCTGAA (SEQ ID NO: 111) and the reverse primer: CGCGAATTCAACATCTA TTTTCTTCTTG-CACT (SEQ ID NO: 112) were designed according to the amino acid sequences of the two ends of the above fragment and the insertion of restriction sites.

The purchased GPR116 cDNA plasmid (Yeli co. ltd., China) was use as template, and the amount of the template was 50 ng. PCR conditions were: 94° C., 2 min; 94° C. 30 s-60° C. 30 s-72° C. 1 min, 30 cycles; 72° C., 10 min; 10° C., 10 min.

The target fragments around 450 bp were recovered from gel. After the BamHI/EcoRI restriction sites were integrated to the H vector of Example 1, 5 plasmids were obtained. The target fragment was respectively inserted into H vectors and PET32a vectors digested by the same enzymes, and then were respectively used for expressing immunization antigen and detection antigen.

The constructed H and PET32a expression vectors were respectively transformed to Rosetta competent cells (Novagen, Merck, Germany). The expression and purification methods for immunization antigens and detection antigens can respectively be seen in Example 3 and Example 4. The produced amount of immunization antigen was 1.7 mg, with the purity of 80%; produced amount of detection antigen was 2.3 mg, with the purity of 95%.

C Immunization Method

The immunization method and dosage for protein GPR116 were as follows.

3 Balb/c mice (Shanghai sippr bk laboratory animals co. ltd., Shanghai) which were 8-10 weeks old were selected for the immunization.

On the first day, 20 μg (the dosage can be 2-200 ug) of the above prepared immunization antigen was completely emulsified with Freund's complete adjuvant (Sigma), and the immunization sites were front leg armpit and inguen, 4 sites all together, wherein about 50 μL was applied for each site.

On the fourteenth day, 10 μg antigen was taken and completely emulsified with Freund's complete adjuvant (Sigma), and then used to immunize the mice at front leg armpit and inguen.

On the 21st day, blood was taken from eyepit of the mice, and ELISA method was used to examine the serum titer, wherein the serum titers of the mice were all higher than 1:32000.

On the 28th day, the mouse with the highest titer was selected, and 50 μg antigen was used for strengthening at abdominal cavity.

D Cell Fusion and Hybridoma Screening

On the 31st day, the mice were sacrificed by cervical dislocation. Spleen cells of the mice were fused with SP20 cells. The cells were suspended in HAT complete medium, and the plated for 4 384 well plates, with 80 μL in each well. The cell plates were cultured at 37° C., 5% $CO_2$ for 6 days, and then totally changed to HT medium. 8 days after the fusion, 10 μL cell supernatant was taken, and diluted 5 times, which was used for ELISA assay.

The operation of the primary screening ELISA was the same to that of Example 5, with the difference that the coating antigen was detection antigen which was expressed by PET32a and which was fused with TRX. The detection antigen per se also contained the selected domain sequence of aa 166-307, and the other components thereof were totally different to H vector. Since the detection also contained other parts of the H vector besides the sequence of the domain parts, and these other parts also produced corresponding antibodies. The detection antigen fused with TRX was used to confirm that the obtained cell strain recognized said surface signature domain rather than other parts expressed by the H vector. The concentration for coating the plates was 1 μg/ml, and the solutions for coating the plated was pH9.6 bicarbonate buffer ($Na_2CO_3$/$NaHCO_3$).

100 clones with highest OD values were selected for sub-cloning and cell strain construction. An antibody library (68 strains) against the surface signature domains of GPR116 protein (the specific domains selected above) was obtained. Cell strains with various applications can be selected from the library. The antibodies secreted by more than 50 cell strains were assayed as having an affinity less than 10 nM, indicating that affinity of the antibodies in the antibody library was in a relatively high level.

E Verification Data

Figure 6:
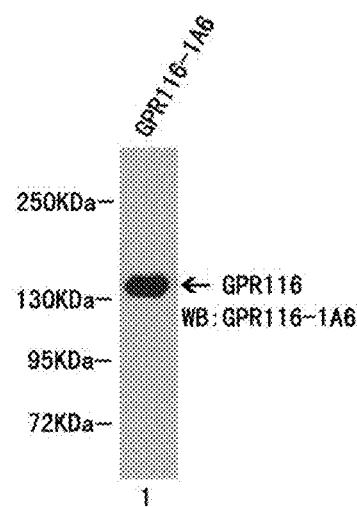
FIG. 6: Western result for the verification of the antibody 1A6 produced against GPR116 protein. WB: Western blotting.

The basis verification method of Western was the same to that of Example 6, and the lysate selected for the verification was Y79 cell (ATCC, USA) lysate. FIG. 6 showed the Western results of a monoclonal antibody 1A6 produced by one cell strain 1A6 of the above 50 cell strains, and said cell strain was deposited in China Center for Type Culture Collection (CCTCC) on Jan. 28, 2011, with the deposition No. CCTCC C201108. 50 cell strains can be used to specifically detect endogenous GPR116 protein. More than 50% of the cell strains were successful in the verification applications of co-immuno-precipitation and immuno-fluorescence.

Example 8

Preparation of Antibodies of Mouse Protein-Aof1

A Design and Expression of the Immunization Antigen

Aof1 protein (a protein containing flavin amine oxidase domain) is a self-protein of mouse. As for self-protein, traditional recombinant protein expression method can hardly be used to prepare antibodies with high affinity. Using the method of the invention, an antibody library with high affinity was successfully prepared.

The full length amino acids of Aof1 protein is:

```
                                           (SEQ ID NO: 113)
  1  MAASRGRSKK RSNLELSPDN LPLRSSGRQA KKKAVEIPDE
     DEDGSSEKKY RKCEKAGCTA

61  AYPVCFASAS ERCAKNGYTS RWYHLSCGEH FCNECFDHYY
     RSHKDGYDKY SAWKRVWTSN

121  GKTEPSPKAF MADQQLPYWV QCTKPECGKW RQLTKEIQLT
     PHMARTYRCG MKPNTITKPD

181  TPDHCSFPED LRVLEVSNHW WYPMLIQPPL LKDSVAAPLL
     SAYYPDCVGM SPSCTSTHRA

241  TVTAATTTTG SASPGEMEPS KAAPSSLVLG MNRYFQPFYQ
     PNECGKALCV RPDVMELDEL

301  YEFPEYSRDP TMYLALRNLI LALWYTNCKE ALTPQKCIPH
     IIVRGLVRIR CVQEVERILY

361  FMTRKGLINT GVLTVAAGQH LLPKHYHNKS VLVVGAGPAG
     LAAARQLHNF GMKVTVLEAK

421  DRIGGRVWDD KSFKGVVVGR GPQIVNGCIN NPVALMCEQL
     GISMRKLGER CDLIQEGGRI

481  TDPTVDKRMD FHFNALLDVV SEWRKDKTLL QDVPLGEKIE
     EIYRAFVKES GIQFSELEGQ

541  VLQFHLSNLE YACGSSLHQV SARSWDHNEF FAQFAGDHTL
     LTPGYSTIIE KLAEGLDIRL

601  KSPVQSIDYT GDEVQVTTTD GMGHSAQKVL VTVPLAILQR
     GAIQFNPPLS EKKMKAINSL

661  GAGIIEKIAL QFPYRFWDSK VQGADFFGHV PPSASQRGLF
     AVFYDMDSQQ SVLMSVITGE

721  AVASLRTMDD KQVLQQCMGI LRELFKEQEI PEPTKYFVTR
     WSTEPWIQMA YSFVKTFGSG

781  EAYDIIAEEI QGTVFFAGEA TNRHFPQTVT GAYLSGVREA
     SKIAAF
```

According to searching in the protein, it was discovered that the protein does not contain trans-membrane domain or signal peptide. Based on the above mentioned principle, the full length of the protein was analyzed, and 5 surface signature peptide sequences were determined.

The method for constructing the tandem polypeptide of immunization antigens was the same to that of Example 2. 7 short peptides were selected, and the sequences can be seen in Table 14.

TABLE 14

| | | | Starting site (based on SEQ ID NO: 113) | Ending site (based on SEQ ID NO: 113) | |
|---|---|---|---|---|---|
| Numbering | Peptide sequences | length/aa | | | Specific Score |
| 1 | KKYRKCEKAG (SEQ ID NO: 114) | 10 | 48 | 57 | 90.2 |
| 2 | AASRGRSKKR (SEQ ID NO: 115) | 10 | 2 | 11 | 89.8 |
| 3 | RSSGRQAKKK (SEQ ID NO: 116) | 10 | 24 | 33 | 88.6 |
| 4 | VRGLVRIRCV (SEQ ID NO: 117) | 10 | 343 | 352 | 89.9 |
| 5 | KYSAWKRVWT (SEQ ID NO: 118) | 10 | 109 | 118 | 90.8 |
| 6 | RILYFMTRKG (SEQ ID NO: 119) | 10 | 357 | 366 | 90.7 |
| 7 | MARTYRCGMK (SEQ ID NO: 120) | 10 | 163 | 172 | 91.1 |

Specific Score Calculation:

1, The protein was cut into segments of 10 aa (gradually cutting, 1-10, 2-11, 3-12 . . . )

2, Blast was conducted for all the 10 aa peptide segments against the specie of the protein 3, The formula for calculating the specific score of each target peptide was: i) the most homogenous 20 sequences of each target polypeptide were selected; ii) the number of identical amino acids in each of the 20 sequences when compared to the target polypeptide was listed; iii) the average of these numbers of identical amino acids was calculated; iv) the specific score of the target polypeptide was: 100−the average 4, The polypeptide fragments with highest specific score were selected, and surface signature peptides were selected based on the specific score in combination with the factors of antigenicity, hydrophilicity, trans-membrane structure, signal peptide etc.

Finally, it was determined that the sequence of the tandem polypeptide displayed by H carrier of the Aof1 protein was: KKYRKCEKAG-GGGGS-AASRGRSKKR-GGGGS-RSSGRQAKKK-GGGGS-VRGLVRIRC V-GGGGS-KYSAWKRVWT-GGGGS-RILYFMTRKG-GGGGS-MARTYR CGMK (SEQ ID NO: 121)

After codon optimization, it was determined that the complete gene sequence to be synthesized was:

```
                                          (SEQ ID NO: 122)
GACACggatccAAGAAATACCGTAAATGCGAGAAAGCAGGAGGTGGCGGC

GGAAGCGCGGCTTCCCGTGGCCGTTCAAAAAAACGTGGCGGTGGAGGGTC

CCGGAGCAGCGGCCGTCAGGCGAAAAAGAAGGGTGGTGGGGATCTGTGC

GTGGCCTGGTGCGTATTCGTTGCGTTGGGGGGGTGGATCAAAATACTCT
```

```
-continued
GCGTGGAAACGTGTGTGGACCGGCGGAGGCGGCAGTCGTATCCTGTATTT

CATGACCCGTAAAGGAGGAGGGGGAGGCTCGATGGCGCGTACCTATCGTT

GTGGGATGAAAgaattcGTGTC
```

Based on the above, the primers used for the complete gene synthesis were determined and can be seen in the following table. The complete gene synthesis method was the same to that of Example 4.

5 μl of the synthesized primers 164_01 to 164_14 were taken (with the concentration of 25 μM) and mixed. Such mixed primers were used as template, and the first round of PCR amplification was conducted under the catalysis of PFU enzyme (ShenNengBoCai co. ltd., Shanghai, China) The PCR conditions were as: 94° C., 2 min; 30 cycles (94° C., 30 s; 60° C., 30 s; 72° C., 1 min); 72° C., 10 min; 10° C., 10 min. 2 μl of the PCR product of the first round was then taken as template, and primers 164_01 and 164_10 (with the concentration of 25 μM) were used for conducting the amplification, with the amplification conditions as set forth above. 1.5% agarose gel electrophoresis was performed, and the target fragments (i.e. the nucleotide sequence to be completely synthesized) were recovered.

TABLE 15

The list of the primers for the complete gene synthesis of Aof1

| Primer names | Primer sequences (5'-3') | The number of bases in each primer |
| --- | --- | --- |
| 164_01 | GACACggatccAAGAAATACCGTAAATGCGAGAAAGCAGGA (SEQ ID NO: 123) | 41 |
| 164_02 | GCCGCGCTTCCGCCGCCACCTCCTGCTTTCTCGCATTTAC (SEQ ID NO: 124) | 40 |
| 164_03 | GCGGAAGCGCGGCTTCCCGTGGCCGTTCAAAAAAACGTGG (SEQ ID NO: 125) | 40 |
| 164_04 | CTGCTCCGGGACCCTCCACCGCCACGTTTTTTTGAACGGC (SEQ ID NO: 126) | 40 |
| 164_05 | AGGGTCCCGGAGCAGCGGCCGTCAGGCGAAAAAGAAGGGT (SEQ ID NO: 127) | 40 |
| 164_06 | GCCACGCACAGATCCCCCACCACCCTTCTTTTTCGCCTGA (SEQ ID NO: 128) | 40 |
| 164_07 | GGGATCTGTGCGTGGCCTGGTGCGTATTCGTTGCGTTGGG (SEQ ID NO: 129) | 40 |
| 164_08 | CAGAGTATTTTGATCCACCCCCCCCAACGCAACGAATACG (SEQ ID NO: 130) | 40 |
| 164_09 | GGGGTGGATCAAAATACTCTGCGTGGAAACGTGTGTGGAC (SEQ ID NO: 131) | 40 |
| 164_10 | GATACGACTGCCGCCTCCGCCGGTCCACACACGTTTCCAC (SEQ ID NO: 132) | 40 |
| 164_11 | GAGGCGGCAGTCGTATCCTGTATTTCATGACCCGTAAAGG (SEQ ID NO: 133) | 40 |
| 164_12 | ATCGAGCCTCCCCCTCCTCCTTTACGGGTCATGAAATACA (SEQ ID NO: 134) | 40 |
| 164_13 | GAGGGGGAGGCTCGATGGCGCGTACCTATCGTTGTGGGAT (SEQ ID NO: 135) | 40 |
| 164_14 | GACACgaattcTTTCATCCCACAACGATAGGTACG (SEQ ID NO: 136) | 35 |

B Expression of the Tandem Polypeptide of Immunization Antigens

The expression method was the same to that of Example 3. All together 1.5 mg of recombinantly expressed tandem polypeptide of immunization antigens was obtained, with the purity of the protein as 85%.

C Synthesis of the Detection Antigens

The construction strategy of the detection antigens was the same to that of Example 4, based on 7 immunogen including the Aof1 protein (see table 16), 7 detection antigens were constructed (see table 17). The expression and purification methods were the same to that of Example 4.

The purified amount of detection antigen 1 was 0.75 mg, with the purity of 85%; the purified amount of detection antigen 2 was 0.9 mg, with the purity of 70%; the purified amount of detection antigen 3 was 1.3 mg, with the purity of 75%; the purified amount of detection antigen 4 was 0.95 mg, with the purity of 95%; the purified amount of detection antigen 5 was 1.9 mg, with the purity of 65%; the purified amount of detection antigen 6 was 1.1 mg, with the purity of 80%; the purified amount of detection antigen 7 was 0.9 mg, with the purity of 85%.

TABLE 16

Tandem polypeptide sequences of 7 immunization antigens

| Protein Name | The sequence of the tandem polypeptide of immunization antigens |
|---|---|
| Aof1 | GKLLGQGAFGggggsPDSPETSKEVggggsGGSVKDQLKAggggsRKYTRQIL EGggggsVKLGDFGASKggggsMDEQEALNSIggggsLTHHFAQLMY (SEQ ID NO: 137) |
| Histone deacetylase 1 | AQTQGTRRKVggggsSVASAVKLNKggggsRDGIDDESYEggggsPDFKLHISP SggggsGGRKNSSNFKggggsKGVKEEVKLAggggsKPVMSKVMEM (SEQ ID NO: 138) |
| OsSPX1 | AADGGEEEAggggsQDRVARAAGREggggsMKFGKSLSSQggggsKDLKKRL KLIggggsEERQAKRARVggggsGDSSPEEQQEggggsKIPVIEQAAK (SEQ ID NO: 139) |
| Vivax | QKMEVQGNLFggggsKKKHANDLQHggggsETYDPEGKFLggggsPKRDDDN AKGggggsEKKHSSETPQggggsEKRNYTNLKKggggsERNEPYNIVD (SEQ ID NO: 140) |
| Knowlesi | DGVYSKKKHAggggsRAKKNNVEKIggggsKNFMEEKDKQggggsPKPDDAK AKGggggsDAQIKKQENKggggsKKKITNHSNRggggsEKRNYTNLKK (SEQ ID NO: 141) |
| Chabaudi | KTNKTFKIKKggggsNKKKHENDLRggggsETYDPKGEFLggggsPGFLYNEQ DKggggsEKYKPLIEQVggggsKTPENINAVKggggsEKRNYTNLKK (SEQ ID NO: 142) |
| Ber | NKKKHENDLKggggsETYDPKGEFLggggsDTKNQGLKVDggggsGEMGLDF DRLggggsEKYKPLIEQVggggsEKRNYTNLKKggggsDRNEPYNIVD (SEQ ID NO: 143) |

TABLE 17

7 detection antigens

| Detection antigen | Sequence |
|---|---|
| Detection antigen 1 | KKYRKCEKAGAQTQGTRRKVAADGGEEEAQKMEVQGNLFDGVYSKKKHA KTNKTFKIKKNKKKHENDLK (SEQ ID NO: 144) |
| Detection antigen 2 | AASRGRSKKRSVASAVKLNKQDRVARAAGREKKKHANDLQHRAKKNNVEK INKKKHENDLRETYDPKGEFL (SEQ ID NO: 145) |
| Detection antigen 3 | RSSGRQAKKKRDGIDDESYEMKFGKSLSSQETYDPEGKFLKNFMEEKDKQET YDPKGEFLDTKNQGLKVD (SEQ ID NO: 146) |
| Detection antigen 4 | VRGL C Immunization Method The immunization method and dosage for protein Aof1 were as follows.

On the first day, 10 μg antigen (H carrier protein carrying the polypeptide sequence of SEQ ID NO:121) was completely mixed with the oligonucleotide adjuvant (detailed method can be seen in the explanation of the oligonucleotide adjuvant in Example 5), and was then used to immunize the mice at hind leg muscle, and two sites all together, wherein 50-100 μL was applied for each site.

On the eighth day, 20 μg antigen was taken and mixed with the oligonucleotide adjuvant, and was then used to immunize the mice at tail end and hind leg muscle, wherein 50-100 μL was applied for each site.

On the twelfth day, 10 μg antigen was completely mixed with the oligonucleotide adjuvant, and was then used to immunize the mice at hind leg muscle.

On the fourteenth day, blood was taken from eyepit of the mice, and ELISA method was used to examine the serum titer, wherein the serum titers of the mice were all higher than 1:32000.

D Cell Fusion and Epitopes Screening

On the fifteenth day, lymph-node cells of 2 mice were taken for conducting the fusion. The methods for cell fusion, positive clone screening, and epitopes screening, were the same to that of Example 5.

The wells that were positive to different detection antigens were just the antibodies against different antigen epitopes, and the screening results can be seen in table 18. Antibodies against all together 6 epitopes were obtained, and the numbers of positive clones were different.

TABLE 18

The data for the recognition epitopes of the monoclonal antibodies of Aof1 protein

| Epitopes | The sequence of epitopes | Clone number |
|---|---|---|
| A | GKLLGQGAFG (SEQ ID NO: 151) | 5 |
| B | PDSPETSKEV (SEQ ID NO: 152) | 8 |
| C | GGSVKDQLKA (SEQ ID NO: 153) | 10 |
| D | RKYTRQILEG (SEQ ID NO: 154) | 0 |
| E | VKLGDFGASK (SEQ ID NO: 155) | 38 |
| F | MDEQEALNSI (SEQ ID NO: 156) | 15 |
| G | LTHHFAQLMY (SEQ ID NO: 157) | 6 |

2-5 positive wells of each epitopes were respectively picked to conduct limiting dilution for sub-cloning. After 3 rounds of sub-clonings, 30 strains of stable hybridoma cell strains were obtained, which were directed to 6 epitopes.

E The Data for Antibody Verification

Figure 7:
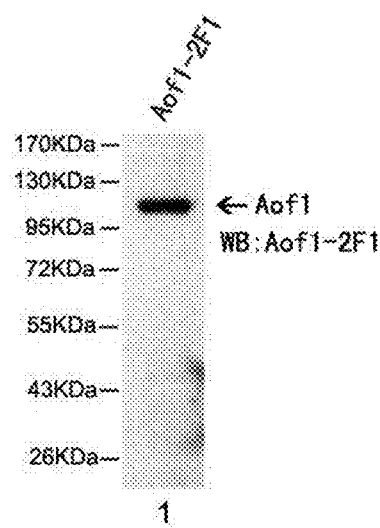
FIG. 7: Western result for the verification of the antibody 2F1 produced against Aof1 protein. WB: Western blotting

The basic method of Western verification was the same to that of Example 6, and the cell line used was Hela cervical cancer cell line (ATCC, USA). FIG. 7 showed the Western results of a monoclonal antibody 2F1 produced by one cell strain 2F1 of the above 30 cell strains, and said cell strain was deposited in China Center for Type Culture Collection (CCTCC) on Jan. 28, 2011, with the deposition No. CCTCC C201109. 5 epitopes, 15 cell strains were successful in Western applications.

The invention claimed is:

1. A method for preparing an antibody against a protein of interest, comprising:
   (a) predicting and/or selecting peptide fragment located on the surface of the protein of interest, wherein said peptide fragment is a linear surface signature peptide and/or a conformational surface signature domain of the protein of interest;
   (b) synthesizing or expressing one or more of said peptide fragments;
   (c) using the product of step (b) to immunize an animal, optionally in combination with an adjuvant;
   (d) using lymphocyte from the immunized animal of step (c) to obtain antibodies;
   (e) using the peptide fragment of step (a) or said protein of interest in native conformation thereof to screen the antibodies obtained in step (d), so as to obtain an antibody library against said protein of interest,
   wherein said peptide fragment of step (a) is predicted or selected through the following process:
   (i) determining a surface peptide by calculating a parameter according to the sequence of the protein of interest, said parameter is selected from: solvent accessibility, disorder index, protein-protein interaction domain prediction, or any combination thereof;
   (ii) aligning the surface peptide determined in step (i) with the proteome of the species that the protein of interest is originated from, so as to select a specific peptide fragment of said protein of interest;
   (iii) aligning the surface peptide determined in step (i) with homologous proteins from other species, so as to screen a conservative sequence of said protein of interest.

2. The method of claim 1, wherein said protein of interest is a native protein, and/or an alternative splicing isoform thereof, and/or a mutant thereof.

3. The method of claim 1, wherein said signature peptide is a peptide, which is 6-12 amino acids in length, which is high hydrophilic, which has high antigenicity, which is not signal peptide, which is not in the trans-membrane region, and which is located in disordered region.

4. The method of claim 1, wherein said signature domain is a sequence specific protein fragment which is 100-500 amino acids in length, and which is expected to have 3 dimensional structure.

5. The method of claim 1, which is used for producing an antibody library against all the proteins of a species.

6. The method of claim 1, wherein the antibody library produced in step (e) comprises antibodies against all the epitopes of the protein of interest.

7. The method of claim 1, wherein the antibody obtained in step (d) is obtained through at least one process selected from:
   (1) fusing lymphocyte from the immunized animal of step (c) with amyeloma cell, so that a hybridoma is generated and then expressed to obtain the antibody;

(2) isolating antigen specific B cell from lymphocyte of the immunized animal of step (c), and then using PCR to clone and express the gene of the antibody so as to obtain the antibody;

(3) isolating mRNA from lymphocyte of the immunized animal of step (c), and then obtaining the antibody through phage display, or ribosome display, or yeast display, or bacteria display, or Baculovirus display, or mammal cell display, or mRNA display.

8. The method of claim 1, wherein one or more of the peptide fragments of step (b) are recombinantly expressed in the form of a fused protein with a protein which enhances the immunogenicity and/or increases the copy number.

9. The method of claim 8, wherein the protein which enhances the immunogenicity and/or increases the copy number is a virus-like particle protein carrier.

10. The method of claim 9, wherein the protein which enhances the immunogenicity and/or increases the copy number is Hepatitis B virus nucleocapsid (HBC) protein.

11. The method of claim 10, wherein said one or more peptide fragments are inserted into loop, N-terminus, or C-terminus of the HBC protein.

12. The method of claim 11, wherein the position into which said one or more peptide fragments are inserted is located between the amino acid residue at position 77 and the amino acid residue at position 82 of the HBC protein.

13. The method of claim 10, wherein 2-10 of the peptide fragments are linked by a linker and inserted into the HBC protein.

14. The method of claim 13, wherein said linker is $(GGGGS)_n$, (SEQ ID NO:158)$_n$, and wherein n=1, 2, 3 or 4.

15. The method of claim 14, wherein n=1 or 2.

16. The method of claim 1, wherein the one or more peptide fragments expressed in step (b) are further coupled with an immune-enhancing protein carrier.

17. The method of claim 16, wherein said immune-enhancing protein carrier is keyhole limpet hemocyanin (KLH).

18. The method of claim 1, wherein the one or more peptide fragments of step (b) are chemically synthesized.

19. The method of claim 1, wherein the adjuvant is selected from: Freund's complete adjuvant, aluminum, CpG, or any combination thereof.

20. The method of claim 1, wherein in said step (c) the animal is immunized at multiple sites.

21. The method of claim 20, wherein the immunization at multiple sites is performed at at least 2 sites selected from: neck and back, tail end, hind foot palm, hind leg inguen, front leg armpit, hind leg muscle.

22. The method of claim 20, wherein multiple immunizations are performed, with the time interval of 2-14 days.

23. The method of claim 22, wherein the immunization protocol used in step (C) comprises the following steps:
 (A). the first immunization: the expression product of step (b) together with Freund's complete adjuvant are used to immunize the animal at neck and back, tail end, hind foot palm, hind leg inguen, and front leg armpit; and the expression product of step (b) together with the adjuvant of aluminum+CpG are used to immunize the animal at hind leg muscle;
 (B). the second immunization: the expression product of step (b) together with Freund's complete adjuvant are used to immunize the animal at neck and back, hind leg inguen, and front leg armpit; and the expression product of step (b) together with the adjuvant of aluminum+CpG are used to immunize the animal at hind leg muscle;
 (C). the third immunization: the expression product of step (b) together with the adjuvant of aluminum+CpG are used to immunize the animal at hind leg muscle, tail end, and front leg armpit;
 (D). the fourth immunization: the expression product of step (b) together with the adjuvant of aluminum+CpG are used to immunize the animal at hind leg muscle, tail end, and front leg armpit.

24. The method of claim 23, wherein the first immunization is performed on the first day, the second immunization is performed on the fifth day, the third immunization is performed on the eighth day, the fourth immunization is performed on the eleventh day.

25. The method of claim 1, wherein the produced antibody is singly IgG subtype.

26. The method of claim 25, wherein the produced antibody is monoclonal antibody.

27. The method of claim 25, wherein the produced antibody is polyclonal antibody.

28. The method of claim 1, wherein the antibodies produced in step (d) is screened through affinity sorting in said step (e).

29. The method of claim 1, further comprising a step (f) of screening functional antibody and detection antibody.

30. The method of claim 29, wherein said detection antibody is screened through Western blotting, IP, IF, IHC, flow cytometry, ELISA, or any combination thereof.

31. The method of claim 29, wherein said functional antibody is screened through blocking or neutralizing assay.

32. The method of claim 1, wherein said method can be used to produce detection antibody and/or functional antibody against more than 90% of proteins of interest.

33. The method of claim 22, wherein multiple immunizations are performed with the time interval of 3-4 days.

* * * * *

SEQUENCE LISTING

<160> NUMBER OF SEQ ID NOS: 164

<210> SEQ ID NO 1
<211> LENGTH: 54
<212> TYPE: DNA
<213> ORGANISM: Artificial
<220> FEATURE:
<223> OTHER INFORMATION: multiple cloning site

<400> SEQUENCE: 1
ggatcctatc agatctatcg ggtaccgtat cgcggccgct tccatatgga attc        54

<210> SEQ ID NO 2
<211> LENGTH: 639
<212> TYPE: DNA
<213> ORGANISM: Artificial
<220> FEATURE:
<223> OTHER INFORMATION: HBc nucleotide sequence after codon
      optimization

<400> SEQUENCE: 2
ccatgggcag cagccaccat catcaccacc acatgaccat gatcaccgat agcctggagt    60
tccatatcga tccgtacaag gaatttggcg cgaccgtgga actgctgagc ttcctgccga   120 gcgactttt tccaagcgtg cgtgacctgc tggatacggc gagcgcactg tatcgtgaag   180
cgctggaaag cccggaacat tgcagcccgc atcataccg gctgcgtcag gcgattctgt   240
gctggggcga actgatgacc ctggcgacct gggtgggcgg caatgaagaa ggtggtggcg   300
gtagcggcgc tggcggatcc tatcagatct atcgggtacc gtatcgcggc cgcttccata   360
tggaattcgg tggcggcggc agcggcggtg gtggcagcga agaagacctg gttgtgagct   420
atgtgaacac caatatgggc ctgaagtttc gtcagctgct gtggtttcat attagctgcc       480
tgacctttgg ccgcgaaacc gtgattgaat acctggtgag ctttggcgtg tggattcgta       540
ccccaccggc gtatcgtccg ccgaatgcgc caattctgag caccctgccg gaaacgaccg       600
tttaagagct ccgtcgacaa gcttgcggcc gcactcgag                              639

<210> SEQ ID NO 3
<211> LENGTH: 42
<212> TYPE: DNA
<213> ORGANISM: Artificial
<220> FEATURE:
<223> OTHER INFORMATION: Primer

<400> SEQUENCE: 3
catgccatgg gcagcagcca ccatcatcac caccacatga cc                          42

<210> SEQ ID NO 4
<211> LENGTH: 40
<212> TYPE: DNA
<213> ORGANISM: Artificial
<220> FEATURE:
<223> OTHER INFORMATION: Primer

<400> SEQUENCE: 4
ctccaggcta tcggtgatca tggtcatgtg gtggtgatga                             40

<210> SEQ ID NO 5
<211> LENGTH: 42
<212> TYPE: DNA
<213> ORGANISM: Artificial
<220> FEATURE:
<223> OTHER INFORMATION: Primer

<400> SEQUENCE: 5
tgatcaccga tagcctggag ttccatatcg atccgtacaa gg                          42

<210> SEQ ID NO 6
<211> LENGTH: 40
<212> TYPE: DNA
<213> ORGANISM: Artificial
<220> FEATURE:
<223> OTHER INFORMATION: Primer

<400> SEQUENCE: 6
ccacggtcgc gccaaattcc ttgtacggat cgatatggaa                             40

<210> SEQ ID NO 7
<211> LENGTH: 40
<212> TYPE: DNA
<213> ORGANISM: Artificial
<220> FEATURE:
<223> OTHER INFORMATION: Primer

<400> SEQUENCE: 7
tggcgcgacc gtggaactgc tgagcttcct gccgagcgac                             40

<210> SEQ ID NO 8
<211> LENGTH: 40
<212> TYPE: DNA
<213> ORGANISM: Artificial
<220> FEATURE:
<223> OTHER INFORMATION: primer

<400> SEQUENCE: 8
caggtcacgc acgcttggaa aaaagtcgct cggcaggaag                                40

<210> SEQ ID NO 9
<211> LENGTH: 40
<212> TYPE: DNA
<213> ORGANISM: Artificial
<220> FEATURE:
<223> OTHER INFORMATION: primer

<400> SEQUENCE: 9
caagcgtgcg tgacctgctg gatacggcga gcgcactgta                                40

<210> SEQ ID NO 10
<211> LENGTH: 40
<212> TYPE: DNA
<213> ORGANISM: Artificial
<220> FEATURE:
<223> OTHER INFORMATION: primer

<400> SEQUENCE: 10
tccgggcttt ccagcgcttc acgatacagt gcgctcgccg                                40

<210> SEQ ID NO 11
<211> LENGTH: 40
<212> TYPE: DNA
<213> ORGANISM: Artificial
<220> FEATURE:
<223> OTHER INFORMATION: primer

<400> SEQUENCE: 11
cgctggaaag cccggaacat tgcagcccgc atcataccgc                                40

<210> SEQ ID NO 12
<211> LENGTH: 40
<212> TYPE: DNA
<213> ORGANISM: Artificial
<220> FEATURE:
<223> OTHER INFORMATION: primer

<400> SEQUENCE: 12
cagcacagaa tcgcctgacg cagcgcggta tgatgcgggc                                40

<210> SEQ ID NO 13
<211> LENGTH: 40
<212> TYPE: DNA
<213> ORGANISM: Artificial
<220> FEATURE:
<223> OTHER INFORMATION: primer

<400> SEQUENCE: 13
gtcaggcgat tctgtgctgg ggcgaactga tgaccctggc                                40

<210> SEQ ID NO 14
<211> LENGTH: 40
<212> TYPE: DNA
<213> ORGANISM: Artificial
<220> FEATURE:
<223> OTHER INFORMATION: primer

<400> SEQUENCE: 14
ttcattgccg cccacccagg tcgccagggt catcagttcg                                40

<210> SEQ ID NO 15
<211> LENGTH: 40
<212> TYPE: DNA
<213> ORGANISM: Artificial

```
<220> FEATURE:
<223> OTHER INFORMATION: primer

<400> SEQUENCE: 15
ggtgggcggc aatgaagaag gtggtggcgg tagcggcggt                          40

<210> SEQ ID NO 16
<211> LENGTH: 40
<212> TYPE: DNA
<213> ORGANISM: Artificial
<220> FEATURE:
<223> OTHER INFORMATION: primer

<400> SEQUENCE: 16
acccgataga tctgatagga tccgccaccg ccgctaccgc                          40

<210> SEQ ID NO 17
<211> LENGTH: 40
<212> TYPE: DNA
<213> ORGANISM: Artificial
<220> FEATURE:
<223> OTHER INFORMATION: primer

<400> SEQUENCE: 17
ggatcctatc agatctatcg ggtaccgtat cgcggccgct                          40

<210> SEQ ID NO 18
<211> LENGTH: 40
<212> TYPE: DNA
<213> ORGANISM: Artificial
<220> FEATURE:
<223> OTHER INFORMATION: primer

<400> SEQUENCE: 18
ccgccgccac cgaattccat atggaagcgg ccgcgatacg                          40

<210> SEQ ID NO 19
<211> LENGTH: 40
<212> TYPE: DNA
<213> ORGANISM: Artificial
<220> FEATURE:
<223> OTHER INFORMATION: primer

<400> SEQUENCE: 19
attcggtggc ggcggcagcg gcggtggtgg cagcgaagaa                          40

<210> SEQ ID NO 20
<211> LENGTH: 40
<212> TYPE: DNA
<213> ORGANISM: Artificial
<220> FEATURE:
<223> OTHER INFORMATION: primer

<400> SEQUENCE: 20
tcacatagct cacaaccagg tcttcttcgc tgccaccacc                          40

<210> SEQ ID NO 21
<211> LENGTH: 40
<212> TYPE: DNA
<213> ORGANISM: Artificial
<220> FEATURE:
<223> OTHER INFORMATION: primer

<400> SEQUENCE: 21
cctggttgtg agctatgtga acaccaatat gggcctgaag                          40
```

<210> SEQ ID NO 22
<211> LENGTH: 40
<212> TYPE: DNA
<213> ORGANISM: Artificial
<220> FEATURE:
<223> OTHER INFORMATION: primer

<400> SEQUENCE: 22
aaccacagca gctgacgaaa cttcaggccc atattggtgt                             40

<210> SEQ ID NO 23
<211> LENGTH: 40
<212> TYPE: DNA
<213> ORGANISM: Artificial
<220> FEATURE:
<223> OTHER INFORMATION: primer

<400> SEQUENCE: 23
tcgtcagctg ctgtggtttc atattagctg cctgaccttt                             40

<210> SEQ ID NO 24
<211> LENGTH: 40
<212> TYPE: DNA
<213> ORGANISM: Artificial
<220> FEATURE:
<223> OTHER INFORMATION: primer

<400> SEQUENCE: 24
aatcacggtt tcgcggccaa aggtcaggca gctaatatga                             40

<210> SEQ ID NO 25
<211> LENGTH: 40
<212> TYPE: DNA
<213> ORGANISM: Artificial
<220> FEATURE:
<223> OTHER INFORMATION: primer

<400> SEQUENCE: 25
gccgcgaaac cgtgattgaa tacctggtga gctttggcgt                             40

<210> SEQ ID NO 26
<211> LENGTH: 40
<212> TYPE: DNA
<213> ORGANISM: Artificial
<220> FEATURE:
<223> OTHER INFORMATION: primer

<400> SEQUENCE: 26
cgccggtggg gtacgaatcc acacgccaaa gctcaccagg                             40

<210> SEQ ID NO 27
<211> LENGTH: 40
<212> TYPE: DNA
<213> ORGANISM: Artificial
<220> FEATURE:
<223> OTHER INFORMATION: primer

<400> SEQUENCE: 27
cgtaccccac cggcgtatcg tccgccgaat gcgccaattc                             40

<210> SEQ ID NO 28
<211> LENGTH: 40
<212> TYPE: DNA
<213> ORGANISM: Artificial
<220> FEATURE:
<223> OTHER INFORMATION: primer

<400> SEQUENCE: 28
gtcgtttccg gcagggtgct cagaattggc gcattcggcg                                    40

<210> SEQ ID NO 29
<211> LENGTH: 40
<212> TYPE: DNA
<213> ORGANISM: Artificial
<220> FEATURE:
<223> OTHER INFORMATION: primer

<400> SEQUENCE: 29
accctgccgg aaacgaccgt ttaagagctc cgtcgacaag                                    40

<210> SEQ ID NO 30
<211> LENGTH: 42
<212> TYPE: DNA
<213> ORGANISM: Artificial
<220> FEATURE:
<223> OTHER INFORMATION: primer

<400> SEQUENCE: 30
ccgctcgagt gcggccgcaa gcttgtcgac ggagctctta aa                                 42

<210> SEQ ID NO 31
<211> LENGTH: 470
<212> TYPE: PRT
<213> ORGANISM: Homo sapiens

<400> SEQUENCE: 31

```
Met Ser Gln Ala Tyr Ser Ser Gln Arg Val Ser Tyr Arg Arg
1               5                   10                  15

Thr Phe Gly Gly Ala Pro Gly Phe Pro Leu Gly Ser Pro Leu Ser Ser
            20                  25                  30

Pro Val Phe Pro Arg Ala Gly Phe Gly Ser Lys Gly Ser Ser Ser Ser
        35                  40                  45

Val Thr Ser Arg Val Tyr Gln Val Ser Arg Thr Ser Gly Gly Ala Gly
    50                  55                  60

Gly Leu Gly Ser Leu Arg Ala Ser Arg Leu Gly Thr Thr Arg Thr Pro
65                  70                  75                  80

Ser Ser Tyr Gly Ala Gly Glu Leu Leu Asp Phe Ser Leu Ala Asp Ala
                85                  90                  95

Val Asn Gln Glu Phe Leu Thr Thr Arg Thr Asn Glu Lys Val Glu Leu
            100                 105                 110

Gln Glu Leu Asn Asp Arg Phe Ala Asn Tyr Ile Glu Lys Val Arg Phe
        115                 120                 125

Leu Glu Gln Gln Asn Ala Ala Leu Ala Ala Glu Val Asn Arg Leu Lys
    130                 135                 140

Gly Arg Glu Pro Thr Arg Val Ala Glu Leu Tyr Glu Glu Glu Leu Arg
145                 150                 155                 160

Glu Leu Arg Arg Gln Val Glu Val Leu Thr Asn Gln Arg Ala Arg Val
                165                 170                 175

Asp Val Glu Arg Asp Asn Leu Leu Asp Asp Leu Gln Arg Leu Lys Ala
            180                 185                 190

Lys Leu Gln Glu Glu Ile Gln Leu Lys Glu Glu Ala Glu Asn Asn Leu
        195                 200                 205

Ala Ala Phe Arg Ala Asp Val Asp Ala Ala Thr Leu Ala Arg Ile Asp
    210                 215                 220
```

Leu Glu Arg Arg Ile Glu Ser Leu Asn Glu Glu Ile Ala Phe Leu Lys
225                 230                 235                 240

Lys Val His Glu Glu Ile Arg Glu Leu Gln Ala Gln Leu Gln Glu
            245                 250                 255

Gln Gln Val Gln Val Glu Met Asp Met Ser Lys Pro Asp Leu Thr Ala
            260                 265                 270

Ala Leu Arg Asp Ile Arg Ala Gln Tyr Glu Thr Ile Ala Ala Lys Asn
        275                 280                 285

Ile Ser Glu Ala Glu Glu Trp Tyr Lys Ser Lys Val Ser Asp Leu Thr
    290                 295                 300

Gln Ala Ala Asn Lys Asn Asn Asp Ala Leu Arg Gln Ala Lys Gln Glu
305                 310                 315                 320

Met Met Glu Tyr Arg His Gln Ile Gln Ser Tyr Thr Cys Glu Ile Asp
            325                 330                 335

Ala Leu Lys Gly Thr Asn Asp Ser Leu Met Arg Gln Met Arg Glu Leu
        340                 345                 350

Glu Asp Arg Phe Ala Ser Glu Ala Ser Gly Tyr Gln Asp Asn Ile Ala
    355                 360                 365

Arg Leu Glu Glu Glu Ile Arg His Leu Lys Asp Glu Met Ala Arg His
370                 375                 380

Leu Arg Glu Tyr Gln Asp Leu Leu Asn Val Lys Met Ala Leu Asp Val
385                 390                 395                 400

Glu Ile Ala Thr Tyr Arg Lys Leu Leu Glu Gly Glu Glu Ser Arg Ile
            405                 410                 415

Asn Leu Pro Ile Gln Thr Tyr Ser Ala Leu Asn Phe Arg Glu Thr Ser
        420                 425                 430

Pro Glu Gln Arg Gly Ser Glu Val His Thr Lys Lys Thr Val Met Ile
    435                 440                 445

Lys Thr Ile Glu Thr Arg Asp Gly Glu Val Val Ser Glu Ala Thr Gln
450                 455                 460

Gln Gln His Glu Val Leu
465                 470

<210> SEQ ID NO 32
<211> LENGTH: 79
<212> TYPE: PRT
<213> ORGANISM: Artificial
<220> FEATURE:
<223> OTHER INFORMATION: tandem antigen

<400> SEQUENCE: 32

Arg Glu Thr Ser Pro Glu Gln Arg Gly Ser Glu Val Gly Gly Gly Gly
1               5                   10                  15

Ser Lys Val Ser Asp Leu Thr Gln Ala Ala Asn Lys Gly Gly Gly Gly
            20                  25                  30

Ser Arg Leu Lys Gly Arg Glu Pro Thr Arg Val Ala Glu Gly Gly Gly
        35                  40                  45

Gly Ser Val Glu Val Leu Thr Asn Gln Arg Ala Arg Val Asp Gly Gly
    50                  55                  60

Gly Gly Ser Glu Glu Ser Arg Ile Asn Leu Pro Ile Gln Thr Tyr
65                  70                  75

<210> SEQ ID NO 33
<211> LENGTH: 12
<212> TYPE: PRT
<213> ORGANISM: Artificial
<220> FEATURE:

<223> OTHER INFORMATION: antigen

<400> SEQUENCE: 33

Arg Glu Thr Ser Pro Glu Gln Arg Gly Ser Glu Val
1               5                   10

<210> SEQ ID NO 34
<211> LENGTH: 11
<212> TYPE: PRT
<213> ORGANISM: Artificial
<220> FEATURE:
<223> OTHER INFORMATION: antigen

<400> SEQUENCE: 34

Lys Val Ser Asp Leu Thr Gln Ala Ala Asn Lys
1               5                   10

<210> SEQ ID NO 35
<211> LENGTH: 12
<212> TYPE: PRT
<213> ORGANISM: Artificial
<220> FEATURE:
<223> OTHER INFORMATION: antigen

<400> SEQUENCE: 35

Arg Leu Lys Gly Arg Glu Pro Thr Arg Val Ala Glu
1               5                   10

<210> SEQ ID NO 36
<211> LENGTH: 12
<212> TYPE: PRT
<213> ORGANISM: Artificial
<220> FEATURE:
<223> OTHER INFORMATION: antigen

<400> SEQUENCE: 36

Val Glu Val Leu Thr Asn Gln Arg Ala Arg Val Asp
1               5                   10

<210> SEQ ID NO 37
<211> LENGTH: 12
<212> TYPE: PRT
<213> ORGANISM: Artificial
<220> FEATURE:
<223> OTHER INFORMATION: antigen

<400> SEQUENCE: 37

Glu Glu Ser Arg Ile Asn Leu Pro Ile Gln Thr Tyr
1               5                   10

<210> SEQ ID NO 38
<211> LENGTH: 261
<212> TYPE: DNA
<213> ORGANISM: Artificial
<220> FEATURE:
<223> OTHER INFORMATION: nucleic acid encoding tandem antigen

<400> SEQUENCE: 38

```
gacacggatc cgtgaaacc agcccggaac agcgtggcag cgaagtgggt ggtggaggtt      60
ctaaagtgag cgatctgacc caggcggcga ataaaggggg aggcggcagc cgtctgaaag    120
gccgtgaacc gacccgtgtg gcggaaggtg ggggtggaag cgtggaagtg ctgaccaatc    180
agcgtgcgcg tgtggatggc ggtggcggct cggaagaaag ccgtattaat ctgccgattc    240
agacctatgg aatttcgtgt c                                              261
```

<210> SEQ ID NO 39
<211> LENGTH: 37
<212> TYPE: DNA
<213> ORGANISM: Artificial
<220> FEATURE:
<223> OTHER INFORMATION: primer

<400> SEQUENCE: 39
gacacggatc ccgtgaaacc agcccggaac agcgtgg    37

<210> SEQ ID NO 40
<211> LENGTH: 40
<212> TYPE: DNA
<213> ORGANISM: Artificial
<220> FEATURE:
<223> OTHER INFORMATION: primer

<400> SEQUENCE: 40
agaacctcca ccacccactt cgctgccacg ctgttccggg    40

<210> SEQ ID NO 41
<211> LENGTH: 40
<212> TYPE: DNA
<213> ORGANISM: Artificial
<220> FEATURE:
<223> OTHER INFORMATION: primer

<400> SEQUENCE: 41
tgggtggtgg aggttctaaa gtgagcgatc tgacccaggc    40

<210> SEQ ID NO 42
<211> LENGTH: 40
<212> TYPE: DNA
<213> ORGANISM: Artificial
<220> FEATURE:
<223> OTHER INFORMATION: primer

<400> SEQUENCE: 42
ctgccgcctc cccctttatt cgccgcctgg gtcagatcgc    40

<210> SEQ ID NO 43
<211> LENGTH: 40
<212> TYPE: DNA
<213> ORGANISM: Artificial
<220> FEATURE:
<223> OTHER INFORMATION: primer

<400> SEQUENCE: 43
gggggaggcg gcagccgtct gaaaggccgt gaaccgaccc    40

<210> SEQ ID NO 44
<211> LENGTH: 40
<212> TYPE: DNA
<213> ORGANISM: Artificial
<220> FEATURE:
<223> OTHER INFORMATION: primer

<400> SEQUENCE: 44
cttccacccc caccttccgc cacacgggtc ggttcacggc    40

<210> SEQ ID NO 45
<211> LENGTH: 40
<212> TYPE: DNA
<213> ORGANISM: Artificial
<220> FEATURE:
<223> OTHER INFORMATION: primer

```
<400> SEQUENCE: 45
gaaggtgggg gtggaagcgt ggaagtgctg accaatcagc                        40

<210> SEQ ID NO 46
<211> LENGTH: 40
<212> TYPE: DNA
<213> ORGANISM: Artificial
<220> FEATURE:
<223> OTHER INFORMATION: primer

<400> SEQUENCE: 46
caccgccatc cacacgcgca cgctgattgg tcagcacttc                        40

<210> SEQ ID NO 47
<211> LENGTH: 40
<212> TYPE: DNA
<213> ORGANISM: Artificial
<220> FEATURE:
<223> OTHER INFORMATION: primer

<400> SEQUENCE: 47
cgtgtggatg gcggtggcgg ctcggaagaa agccgtatta                        40

<210> SEQ ID NO 48
<211> LENGTH: 51
<212> TYPE: DNA
<213> ORGANISM: Artificial
<220> FEATURE:
<223> OTHER INFORMATION: primer

<400> SEQUENCE: 48
gacacgaatt cataggtctg aatcggcaga ttaatacggc tttcttccga g            51

<210> SEQ ID NO 49
<211> LENGTH: 79
<212> TYPE: PRT
<213> ORGANISM: Artificial
<220> FEATURE:
<223> OTHER INFORMATION: antigen

<400> SEQUENCE: 49

Arg Glu Thr Ser Pro Glu Gln Arg Gly Ser Glu Val Gly Gly Gly Gly
1               5                   10                  15

Ser Lys Val Ser Asp Leu Thr Gln Ala Ala Asn Lys Gly Gly Gly Gly
            20                  25                  30

Ser Arg Leu Lys Gly Arg Glu Pro Thr Arg Val Ala Glu Gly Gly Gly
        35                  40                  45

Gly Ser Val Glu Val Leu Thr Asn Gln Arg Ala Arg Val Asp Gly Gly
    50                  55                  60

Gly Gly Ser Glu Glu Ser Arg Ile Asn Leu Pro Ile Gln Thr Tyr
65                  70                  75

<210> SEQ ID NO 50
<211> LENGTH: 79
<212> TYPE: PRT
<213> ORGANISM: Artificial
<220> FEATURE:
<223> OTHER INFORMATION: antigen

<400> SEQUENCE: 50

Leu Arg Pro Ser Thr Ser Arg Ser Leu Tyr Ala Ser Gly Gly Gly Gly
1               5                   10                  15
```

Ser Ile Asn Glu Thr Ser Gln His His Asp Asp Leu Glu Gly Gly
            20                  25                  30

Gly Ser Ala Ile Asn Thr Glu Phe Lys Asn Thr Arg Thr Gly Gly Gly
                35                  40                  45

Gly Ser Glu Gln Leu Lys Gly Gln Gly Lys Ser Arg Leu Gly Gly Gly
    50                  55                  60

Gly Gly Ser Gln Arg Glu Glu Ala Glu Asn Thr Leu Gln Ser Phe
65                  70                  75

<210> SEQ ID NO 51
<211> LENGTH: 78
<212> TYPE: PRT
<213> ORGANISM: Artificial
<220> FEATURE:
<223> OTHER INFORMATION: antigen

<400> SEQUENCE: 51

Lys Lys Lys Trp Asn Leu Gly Ser Asn Ala Lys Asp Gly Gly Gly Gly
1               5                   10                  15

Ser Asp Gly Val Arg Gln Ser Arg Ala Ser Asp Lys Gly Gly Gly Gly
            20                  25                  30

Ser Cys Lys Gly Ser Gln Asn Lys Ser Lys Pro Leu Gly Gly Gly Gly
                35                  40                  45

Ser Val Lys Val Tyr Asp Tyr Gln Glu Asp Gly Ser Val Gly Gly Gly
    50                  55                  60

Gly Ser Glu Ala Lys Asn Ile Thr Trp Phe Lys Asp Gly Lys
65                  70                  75

<210> SEQ ID NO 52
<211> LENGTH: 78
<212> TYPE: PRT
<213> ORGANISM: Artificial
<220> FEATURE:
<223> OTHER INFORMATION: antigen

<400> SEQUENCE: 52

Asp Lys Asn Ile Gly Gly Asp Glu Asp Lys Gly Gly Gly Gly Ser
1               5                   10                  15

Glu Glu Met Gly Gly Ile Thr Gln Thr Pro Tyr Lys Gly Gly Gly Gly
            20                  25                  30

Ser Cys Tyr Pro Arg Gly Ser Lys Pro Glu Asp Ala Gly Gly Gly Gly
                35                  40                  45

Ser Asp His Leu Ser Leu Lys Glu Phe Ser Glu Leu Glu Gly Gly Gly
    50                  55                  60

Gly Ser Gly Gln Arg Asp Leu Tyr Ser Gly Leu Asn Gln Arg
65                  70                  75

<210> SEQ ID NO 53
<211> LENGTH: 79
<212> TYPE: PRT
<213> ORGANISM: Artificial
<220> FEATURE:
<223> OTHER INFORMATION: antigen

<400> SEQUENCE: 53

Val Gln Glu Gly Asn Glu Ser Tyr Gln Gln Ser Cys Gly Gly Gly Gly
1               5                   10                  15

Ser Glu Asp Ala His Phe Gln Cys Pro His Asn Ser Ser Gly Gly Gly
            20                  25                  30

Gly Ser Arg Lys Arg Trp Gln Asn Glu Lys Leu Gly Leu Asp Gly Gly

```
            35                  40                  45

Gly Gly Ser Glu Asp Ile Ser Arg Gly Leu Gln Gly Thr Tyr Gly Gly
     50                  55                  60

Gly Gly Ser Gly Pro Gly Glu Asp Pro Asn Gly Thr Leu Ile Ile
65                  70                  75

<210> SEQ ID NO 54
<211> LENGTH: 59
<212> TYPE: PRT
<213> ORGANISM: Artificial
<220> FEATURE:
<223> OTHER INFORMATION: antigen

<400> SEQUENCE: 54

Arg Glu Thr Ser Pro Glu Gln Arg Gly Ser Glu Val Leu Arg Pro Ser
1               5                   10                  15

Thr Ser Arg Ser Leu Tyr Ala Ser Lys Lys Trp Asn Leu Gly Ser
            20                  25                  30

Asn Ala Lys Asp Asp Lys Asn Ile Gly Gly Asp Glu Asp Lys Val
        35                  40                  45

Gln Glu Gly Asn Glu Ser Tyr Gln Gln Ser Cys
    50                  55

<210> SEQ ID NO 55
<211> LENGTH: 59
<212> TYPE: PRT
<213> ORGANISM: Artificial
<220> FEATURE:
<223> OTHER INFORMATION: antigen

<400> SEQUENCE: 55

Lys Val Ser Asp Leu Thr Gln Ala Ala Asn Lys Asn Ile Asn Glu Thr
1               5                   10                  15

Ser Gln His His Asp Asp Leu Glu Asp Gly Val Arg Gln Ser Arg Ala
            20                  25                  30

Ser Asp Lys Glu Glu Met Gly Gly Ile Thr Gln Thr Pro Tyr Lys Glu
        35                  40                  45

Asp Ala His Phe Gln Cys Pro His Asn Ser Ser
    50                  55

<210> SEQ ID NO 56
<211> LENGTH: 57
<212> TYPE: PRT
<213> ORGANISM: Artificial
<220> FEATURE:
<223> OTHER INFORMATION: antigen

<400> SEQUENCE: 56

Arg Leu Lys Gly Arg Glu Pro Thr Arg Val Ala Glu Ala Ile Asn Thr
1               5                   10                  15

Glu Phe Lys Asn Thr Arg Thr Cys Lys Gly Ser Gln Asn Lys Ser Lys
            20                  25                  30

Pro Leu Cys Tyr Pro Arg Gly Ser Lys Pro Glu Asp Ala Arg Lys Arg
        35                  40                  45

Trp Gln Asn Glu Lys Leu Gly Leu Asp
    50                  55

<210> SEQ ID NO 57
<211> LENGTH: 59
<212> TYPE: PRT
<213> ORGANISM: Artificial
```

<220> FEATURE:
<223> OTHER INFORMATION: antigen

<400> SEQUENCE: 57

Val Glu Val Leu Thr Asn Gln Arg Ala Arg Val Asp Glu Gln Leu Lys
1               5                   10                  15

Gly Gln Gly Lys Ser Arg Leu Gly Val Lys Val Tyr Asp Tyr Gln Glu
            20                  25                  30

Asp Gly Ser Val Asp His Leu Ser Leu Lys Glu Phe Ser Glu Leu Glu
        35                  40                  45

Glu Asp Ile Ser Arg Gly Leu Gln Gly Thr Tyr
    50                  55

<210> SEQ ID NO 58
<211> LENGTH: 60
<212> TYPE: PRT
<213> ORGANISM: Artificial
<220> FEATURE:
<223> OTHER INFORMATION: antigen

<400> SEQUENCE: 58

Glu Glu Ser Arg Ile Asn Leu Pro Ile Gln Thr Tyr Gln Arg Glu Glu
1               5                   10                  15

Ala Glu Asn Thr Leu Gln Ser Phe Glu Ala Lys Asn Ile Thr Trp Phe
            20                  25                  30

Lys Asp Gly Lys Gly Gln Arg Asp Leu Tyr Ser Gly Leu Asn Gln Arg
        35                  40                  45

Gly Pro Gly Glu Asp Pro Asn Gly Thr Leu Ile Ile
    50                  55                  60

<210> SEQ ID NO 59
<211> LENGTH: 177
<212> TYPE: DNA
<213> ORGANISM: Artificial
<220> FEATURE:
<223> OTHER INFORMATION: antigen encoding sequence

<400> SEQUENCE: 59
cgtgaaacca gcccggaaca gcgtggcagc gaagtgctgc gtccgagcac cagccgtagc    60
ctgtatgcga gcaagaaaaa atggaatctg ggcagcaatg cgaaagatga caaaaacatt   120
ggcggcgacg aggatgataa ggtgcaggaa ggcaacgaaa gctatcagca aagctgc      177

<210> SEQ ID NO 60
<211> LENGTH: 177
<212> TYPE: DNA
<213> ORGANISM: Artificial
<220> FEATURE:
<223> OTHER INFORMATION: antigen encoding sequence

<400> SEQUENCE: 60
aaagtgtcag acctgaccca ggcggcgaat aagaacatta cgaaaccag ccagcatcac    60 gatgatctgg aagatggcgt gcgtcagagc cgtgcgagcg ataaagaaga aatgggcggc   120
attacccaga ccccgtataa agaggatgca cattttcagt gcccgcataa tagcagc      177

<210> SEQ ID NO 61
<211> LENGTH: 171
<212> TYPE: DNA
<213> ORGANISM: Artificial
<220> FEATURE:
<223> OTHER INFORMATION: antigen encodin sequence

<400> SEQUENCE: 61
cgtctgaaag gccgtgaacc gacccgtgtg gcggaagcga ttaacaccga atttaagaat      60
acccgtacct gcaaaggcag ccagaataaa tcgaaaccgc tgtgctatcc gcgtggcagc     120
aaaccggaag atgcgcgtaa acggtggcag aatgaaaaac tgggcctgga t              171

<210> SEQ ID NO 62
<211> LENGTH: 177
<212> TYPE: DNA
<213> ORGANISM: Artificial
<220> FEATURE:
<223> OTHER INFORMATION: antigen encoding sequence

<400> SEQUENCE: 62
gtggaagtgc tgaccaatca gcgtgcgcgt gtggatgaac agctgaaagg ccagggcaaa      60
agccgtctgg gtgtgaaagt gtatgattat caggaagatg cagcgtgga tcatctgagc     120 ctgaaagaat ttagcgaact ggaagaagac atcagccgtg gctgcaggg cacctat        177

<210> SEQ ID NO 63
<211> LENGTH: 180
<212> TYPE: DNA
<213> ORGANISM: Artificial
<220> FEATURE:
<223> OTHER INFORMATION: antigen encoding sequence

<400> SEQUENCE: 63
gaagaaagtc gtattaatct gccgattcag acctatcagc gtgaggaagc ggaaaatacc      60
ctgcagtcgt ttgaagcgaa aaacattacc tggttcaaag atggcaaagg ccagcgggat     120
ctgtatagcg gcctgaacca acgtggtccg ggcgaagatc cgaatggcac cctgattatt     180

<210> SEQ ID NO 64
<211> LENGTH: 39
<212> TYPE: DNA
<213> ORGANISM: Artificial
<220> FEATURE:
<223> OTHER INFORMATION: primer

<400> SEQUENCE: 64
gacacggatc ccgtgaaacc agcccggaac agcgtggca                             39

<210> SEQ ID NO 65
<211> LENGTH: 40
<212> TYPE: DNA
<213> ORGANISM: Artificial
<220> FEATURE:
<223> OTHER INFORMATION: primer

<400> SEQUENCE: 65
ctggtgctcg gacgcagcac ttcgctgcca cgctgttccg                            40

<210> SEQ ID NO 66
<211> LENGTH: 40
<212> TYPE: DNA
<213> ORGANISM: Artificial
<220> FEATURE:
<223> OTHER INFORMATION: primer

<400> SEQUENCE: 66
gcgtccgagc accagccgta gcctgtatgc gagcaagaaa                            40

<210> SEQ ID NO 67
<211> LENGTH: 40

```
<212> TYPE: DNA
<213> ORGANISM: Artificial
<220> FEATURE:
<223> OTHER INFORMATION: primer

<400> SEQUENCE: 67
attgctgccc agattccatt ttttcttgct cgcatacagg                    40

<210> SEQ ID NO 68
<211> LENGTH: 40
<212> TYPE: DNA
<213> ORGANISM: Artificial
<220> FEATURE:
<223> OTHER INFORMATION: primer

<400> SEQUENCE: 68
tggaatctgg gcagcaatgc gaaagatgac aaaaacattg                    40

<210> SEQ ID NO 69
<211> LENGTH: 40
<212> TYPE: DNA
<213> ORGANISM: Artificial
<220> FEATURE:
<223> OTHER INFORMATION: primer

<400> SEQUENCE: 69
tatcatcctc gtcgccgcca atgtttttgt catctttcgc                    40

<210> SEQ ID NO 70
<211> LENGTH: 40
<212> TYPE: DNA
<213> ORGANISM: Artificial
<220> FEATURE:
<223> OTHER INFORMATION: primer

<400> SEQUENCE: 70
cggcgacgag gatgataagg tgcaggaagg caacgaaagc                    40

<210> SEQ ID NO 71
<211> LENGTH: 44
<212> TYPE: DNA
<213> ORGANISM: Artificial
<220> FEATURE:
<223> OTHER INFORMATION: primer

<400> SEQUENCE: 71
gacacgaatt cgcagctttg ctgatagctt tcgttgcctt cctg              44

<210> SEQ ID NO 72
<211> LENGTH: 43
<212> TYPE: DNA
<213> ORGANISM: Artificial
<220> FEATURE:
<223> OTHER INFORMATION: primer

<400> SEQUENCE: 72
gacacggatc caaagtgtca gacctgaccc aggcggcgaa taa                43

<210> SEQ ID NO 73
<211> LENGTH: 40
<212> TYPE: DNA
<213> ORGANISM: Artificial
<220> FEATURE:
<223> OTHER INFORMATION: primer

<400> SEQUENCE: 73
```
tgctggctgg tttcgttaat gttcttattc gccgcctggg                                    40

<210> SEQ ID NO 74
<211> LENGTH: 40
<212> TYPE: DNA
<213> ORGANISM: Artificial
<220> FEATURE:
<223> OTHER INFORMATION: primer

<400> SEQUENCE: 74
aacgaaacca gccagcatca cgatgatctg gaagatggcg                                    40

<210> SEQ ID NO 75
<211> LENGTH: 40
<212> TYPE: DNA
<213> ORGANISM: Artificial
<220> FEATURE:
<223> OTHER INFORMATION: primer

<400> SEQUENCE: 75
cgctcgcacg gctctgacgc acgccatctt ccagatcatc                                    40

<210> SEQ ID NO 76
<211> LENGTH: 40
<212> TYPE: DNA
<213> ORGANISM: Artificial
<220> FEATURE:
<223> OTHER INFORMATION: primer

<400> SEQUENCE: 76
gagccgtgcg agcgataaag aagaaatggg cggcattacc                                    40

<210> SEQ ID NO 77
<211> LENGTH: 40
<212> TYPE: DNA
<213> ORGANISM: Artificial
<220> FEATURE:
<223> OTHER INFORMATION: primer

<400> SEQUENCE: 77
catcctcttt atacggggtc tgggtaatgc cgcccatttc                                    40

<210> SEQ ID NO 78
<211> LENGTH: 40
<212> TYPE: DNA
<213> ORGANISM: Artificial
<220> FEATURE:
<223> OTHER INFORMATION: primer

<400> SEQUENCE: 78
agaccccgta taagaggat gcacattttc agtgcccgca                                     40

<210> SEQ ID NO 79
<211> LENGTH: 38
<212> TYPE: DNA
<213> ORGANISM: Artificial
<220> FEATURE:
<223> OTHER INFORMATION: primer

<400> SEQUENCE: 79
gacacgaatt cgctgctatt atgcgggcac tgaaaatg                                      38

<210> SEQ ID NO 80
<211> LENGTH: 34
<212> TYPE: DNA
<213> ORGANISM: Artificial

```
<220> FEATURE:
<223> OTHER INFORMATION: primer

<400> SEQUENCE: 80
gacacggatc ccgtctgaaa ggccgtgaac cgac                                34

<210> SEQ ID NO 81
<211> LENGTH: 40
<212> TYPE: DNA
<213> ORGANISM: Artificial
<220> FEATURE:
<223> OTHER INFORMATION: primer

<400> SEQUENCE: 81
tgttaatcgc ttccgccaca cgggtcggtt cacggccttt                          40

<210> SEQ ID NO 82
<211> LENGTH: 40
<212> TYPE: DNA
<213> ORGANISM: Artificial
<220> FEATURE:
<223> OTHER INFORMATION: primer

<400> SEQUENCE: 82
tggcggaagc gattaacacc gaatttaaga atacccgtac                          40

<210> SEQ ID NO 83
<211> LENGTH: 40
<212> TYPE: DNA
<213> ORGANISM: Artificial
<220> FEATURE:
<223> OTHER INFORMATION: primer

<400> SEQUENCE: 83
ttctggctgc ctttgcaggt acgggtattc ttaaattcgg                          40

<210> SEQ ID NO 84
<211> LENGTH: 40
<212> TYPE: DNA
<213> ORGANISM: Artificial
<220> FEATURE:
<223> OTHER INFORMATION: primer

<400> SEQUENCE: 84
tgcaaaggca gccagaataa atcgaaaccg ctgtgctatc                          40

<210> SEQ ID NO 85
<211> LENGTH: 40
<212> TYPE: DNA
<213> ORGANISM: Artificial
<220> FEATURE:
<223> OTHER INFORMATION: primer

<400> SEQUENCE: 85
tcttccggtt tgctgccacg cggatagcac agcggtttcg                          40

<210> SEQ ID NO 86
<211> LENGTH: 40
<212> TYPE: DNA
<213> ORGANISM: Artificial
<220> FEATURE:
<223> OTHER INFORMATION: primer

<400> SEQUENCE: 86
ggcagcaaac cggaagatgc gcgtaaacgg tggcagaatg                          40
```

<210> SEQ ID NO 87
<211> LENGTH: 47
<212> TYPE: DNA
<213> ORGANISM: Artificial
<220> FEATURE:
<223> OTHER INFORMATION: primer

<400> SEQUENCE: 87
gacacgaatt catccaggcc cagttttttca ttctgccacc gtttacg         47

<210> SEQ ID NO 88
<211> LENGTH: 42
<212> TYPE: DNA
<213> ORGANISM: Artificial
<220> FEATURE:
<223> OTHER INFORMATION: primer

<400> SEQUENCE: 88
gacacggatc cgtggaagtg ctgaccaatc agcgtgcgcg tg              42

<210> SEQ ID NO 89
<211> LENGTH: 40
<212> TYPE: DNA
<213> ORGANISM: Artificial
<220> FEATURE:
<223> OTHER INFORMATION: primer

<400> SEQUENCE: 89
gccctggcct ttcagctgtt catccacacg cgcacgctga                 40

<210> SEQ ID NO 90
<211> LENGTH: 40
<212> TYPE: DNA
<213> ORGANISM: Artificial
<220> FEATURE:
<223> OTHER INFORMATION: primer

<400> SEQUENCE: 90
gctgaaaggc cagggcaaaa gccgtctggg tgtgaaagtg                 40

<210> SEQ ID NO 91
<211> LENGTH: 40
<212> TYPE: DNA
<213> ORGANISM: Artificial
<220> FEATURE:
<223> OTHER INFORMATION: primer

<400> SEQUENCE: 91
tgccatcttc ctgataatca tacactttca cacccagacg                 40

<210> SEQ ID NO 92
<211> LENGTH: 40
<212> TYPE: DNA
<213> ORGANISM: Artificial
<220> FEATURE:
<223> OTHER INFORMATION: primer

<400> SEQUENCE: 92
atgattatca ggaagatggc agcgtggatc atctgagcct                 40

<210> SEQ ID NO 93
<211> LENGTH: 40
<212> TYPE: DNA
<213> ORGANISM: Artificial
<220> FEATURE:
<223> OTHER INFORMATION: primer

<400> SEQUENCE: 93
ttccagttcg ctaaattctt tcaggctcag atgatccacg                                    40

<210> SEQ ID NO 94
<211> LENGTH: 40
<212> TYPE: DNA
<213> ORGANISM: Artificial
<220> FEATURE:
<223> OTHER INFORMATION: primer

<400> SEQUENCE: 94
gaaagaattt agcgaactgg aagaagacat cagccgtggg                                    40

<210> SEQ ID NO 95
<211> LENGTH: 43
<212> TYPE: DNA
<213> ORGANISM: Artificial
<220> FEATURE:
<223> OTHER INFORMATION: primer

<400> SEQUENCE: 95
gacacgaatt cataggtgcc ctgcagccca cggctgatgt ctt                                43

<210> SEQ ID NO 96
<211> LENGTH: 44
<212> TYPE: DNA
<213> ORGANISM: Artificial
<220> FEATURE:
<223> OTHER INFORMATION: primer

<400> SEQUENCE: 96
gacacggatc cgaagaaagt cgtattaatc tgccgattca gacc                               44

<210> SEQ ID NO 97
<211> LENGTH: 40
<212> TYPE: DNA
<213> ORGANISM: Artificial
<220> FEATURE:
<223> OTHER INFORMATION: primer

<400> SEQUENCE: 97
ccgcttcctc acgctgatag gtctgaatcg gcagattaat                                    40

<210> SEQ ID NO 98
<211> LENGTH: 40
<212> TYPE: DNA
<213> ORGANISM: Artificial
<220> FEATURE:
<223> OTHER INFORMATION: primer

<400> SEQUENCE: 98
cagcgtgagg aagcggaaaa taccctgcag tcgtttgaag                                    40

<210> SEQ ID NO 99
<211> LENGTH: 40
<212> TYPE: DNA
<213> ORGANISM: Artificial
<220> FEATURE:
<223> OTHER INFORMATION: primer

<400> SEQUENCE: 99
ttgaaccagg taatgttttt cgcttcaaac gactgcaggg                                    40

<210> SEQ ID NO 100

```
<211> LENGTH: 40
<212> TYPE: DNA
<213> ORGANISM: Artificial
<220> FEATURE:
<223> OTHER INFORMATION: primer

<400> SEQUENCE: 100
cgaaaaacat tacctggttc aaagatggca aaggccagcg                              40

<210> SEQ ID NO 101
<211> LENGTH: 40
<212> TYPE: DNA
<213> ORGANISM: Artificial
<220> FEATURE:
<223> OTHER INFORMATION: primer

<400> SEQUENCE: 101
ttggttcagg ccgctataca gatcccgctg gcctttgcca                              40

<210> SEQ ID NO 102
<211> LENGTH: 40
<212> TYPE: DNA
<213> ORGANISM: Artificial
<220> FEATURE:
<223> OTHER INFORMATION: primer

<400> SEQUENCE: 102
atagcggcct gaaccaacgt ggtccgggcg aagatccgaa                              40

<210> SEQ ID NO 103
<211> LENGTH: 43
<212> TYPE: DNA
<213> ORGANISM: Artificial
<220> FEATURE:
<223> OTHER INFORMATION: primer

<400> SEQUENCE: 103
gacacgaatt caataatcag ggtgccattc ggatcttcgc ccg                          43

<210> SEQ ID NO 104
<211> LENGTH: 20
<212> TYPE: DNA
<213> ORGANISM: Artificial
<220> FEATURE:
<223> OTHER INFORMATION: DNA adjuvant

<400> SEQUENCE: 104
tccatgacgt tcctgacgtt                                                    20

<210> SEQ ID NO 105
<211> LENGTH: 12
<212> TYPE: PRT
<213> ORGANISM: Artificial
<220> FEATURE:
<223> OTHER INFORMATION: epitope

<400> SEQUENCE: 105

Arg Glu Thr Ser Pro Glu Gln Arg Gly Ser Glu Val
1               5                   10

<210> SEQ ID NO 106
<211> LENGTH: 10
<212> TYPE: PRT
<213> ORGANISM: Artificial
<220> FEATURE:
<223> OTHER INFORMATION: epitope
```

```
<400> SEQUENCE: 106

Lys Val Ser Asp Leu Thr Gln Ala Ala Asn
1               5                   10

<210> SEQ ID NO 107
<211> LENGTH: 12
<212> TYPE: PRT
<213> ORGANISM: Artificial
<220> FEATURE:
<223> OTHER INFORMATION: epitope

<400> SEQUENCE: 107

Arg Leu Lys Gly Arg Glu Pro Thr Arg Val Ala Glu
1               5                   10

<210> SEQ ID NO 108
<211> LENGTH: 12
<212> TYPE: PRT
<213> ORGANISM: Artificial
<220> FEATURE:
<223> OTHER INFORMATION: epitope

<400> SEQUENCE: 108

Val Glu Val Leu Thr Asn Gln Arg Ala Arg Val Asp
1               5                   10

<210> SEQ ID NO 109
<211> LENGTH: 12
<212> TYPE: PRT
<213> ORGANISM: Artificial
<220> FEATURE:
<223> OTHER INFORMATION: epitope

<400> SEQUENCE: 109

Glu Glu Ser Arg Ile Asn Leu Pro Ile Gln Thr Tyr
1               5                   10

<210> SEQ ID NO 110
<211> LENGTH: 1346
<212> TYPE: PRT
<213> ORGANISM: Homo sapiens

<400> SEQUENCE: 110

Met Lys Ser Pro Arg Arg Thr Thr Leu Cys Leu Met Phe Ile Val Ile
1               5                   10                  15

Tyr Ser Ser Lys Ala Ala Leu Asn Trp Asn Tyr Glu Ser Thr Ile His
                20                  25                  30

Pro Leu Ser Leu His Glu His Glu Pro Ala Gly Glu Glu Ala Leu Arg
            35                  40                  45

Gln Lys Arg Ala Val Ala Thr Lys Ser Pro Thr Ala Glu Glu Tyr Thr
        50                  55                  60

Val Asn Ile Glu Ile Ser Phe Glu Asn Ala Ser Phe Leu Asp Pro Ile
65                  70                  75                  80

Lys Ala Tyr Leu Asn Ser Leu Ser Phe Pro Ile His Gly Asn Asn Thr
                85                  90                  95

Asp Gln Ile Thr Asp Ile Leu Ser Ile Asn Val Thr Thr Val Cys Arg
            100                 105                 110

Pro Ala Gly Asn Glu Ile Trp Cys Ser Cys Glu Thr Gly Tyr Gly Trp
        115                 120                 125

Pro Arg Glu Arg Cys Leu His Asn Leu Ile Cys Gln Glu Arg Asp Val
        130                 135                 140
```

```
Phe Leu Pro Gly His His Cys Ser Cys Leu Lys Glu Leu Pro Pro Asn
145                 150                 155                 160

Gly Pro Phe Cys Leu Leu Gln Glu Asp Val Thr Leu Asn Met Arg Val
            165                 170                 175

Arg Leu Asn Val Gly Phe Gln Glu Asp Leu Met Asn Thr Ser Ser Ala
        180                 185                 190

Leu Tyr Arg Ser Tyr Lys Thr Asp Leu Glu Thr Ala Phe Arg Lys Gly
    195                 200                 205

Tyr Gly Ile Leu Pro Gly Phe Lys Gly Val Thr Val Thr Gly Phe Lys
210                 215                 220

Ser Gly Ser Val Val Thr Tyr Glu Val Lys Thr Thr Pro Pro Ser
225                 230                 235                 240

Leu Glu Leu Ile His Lys Ala Asn Glu Gln Val Val Gln Ser Leu Asn
                245                 250                 255

Gln Thr Tyr Lys Met Asp Tyr Asn Ser Phe Gln Ala Val Thr Ile Asn
            260                 265                 270

Glu Ser Asn Phe Phe Val Thr Pro Glu Ile Ile Phe Glu Gly Asp Thr
        275                 280                 285

Val Ser Leu Val Cys Glu Lys Glu Val Leu Ser Ser Asn Val Ser Trp
    290                 295                 300

Arg Tyr Glu Glu Gln Gln Leu Glu Ile Gln Asn Ser Ser Arg Phe Ser
305                 310                 315                 320

Ile Tyr Thr Ala Leu Phe Asn Asn Met Thr Ser Val Ser Lys Leu Thr
                325                 330                 335

Ile His Asn Ile Thr Pro Gly Asp Ala Gly Glu Tyr Val Cys Lys Leu
            340                 345                 350

Ile Leu Asp Ile Phe Glu Tyr Glu Cys Lys Lys Lys Ile Asp Val Met
        355                 360                 365

Pro Ile Gln Ile Leu Ala Asn Glu Glu Met Lys Val Met Cys Asp Asn
    370                 375                 380

Asn Pro Val Ser Leu Asn Cys Cys Ser Gln Gly Asn Val Asn Trp Ser
385                 390                 395                 400

Lys Val Glu Trp Lys Gln Glu Gly Lys Ile Asn Ile Pro Gly Thr Pro
                405                 410                 415

Glu Thr Asp Ile Asp Ser Ser Cys Ser Arg Tyr Thr Leu Lys Ala Asp
            420                 425                 430

Gly Thr Gln Cys Pro Ser Gly Ser Gly Thr Thr Val Ile Tyr Thr
        435                 440                 445

Cys Glu Phe Ile Ser Ala Tyr Gly Ala Arg Gly Ser Ala Asn Ile Lys
    450                 455                 460

Val Thr Phe Ile Ser Val Ala Asn Leu Thr Ile Thr Pro Asp Pro Ile
465                 470                 475                 480

Ser Val Ser Glu Gly Gln Asn Phe Ser Ile Lys Cys Ile Ser Asp Val
                485                 490                 495

Ser Asn Tyr Asp Glu Val Tyr Trp Asn Thr Ser Ala Gly Ile Lys Ile
            500                 505                 510

Tyr Gln Arg Phe Tyr Thr Thr Arg Arg Tyr Leu Asp Gly Ala Glu Ser
        515                 520                 525

Val Leu Thr Val Lys Thr Ser Thr Arg Glu Trp Asn Gly Thr Tyr His
    530                 535                 540

Cys Ile Phe Arg Tyr Lys Asn Ser Tyr Ser Ile Ala Thr Lys Asp Val
545                 550                 555                 560

Ile Val His Pro Leu Pro Leu Lys Leu Asn Ile Met Val Asp Pro Leu
```

-continued

```
                565                 570                 575
Glu Ala Thr Val Ser Cys Ser Gly Ser His His Ile Lys Cys Cys Ile
            580                 585                 590

Glu Glu Asp Gly Asp Tyr Lys Val Thr Phe His Thr Gly Ser Ser Ser
            595                 600                 605

Leu Pro Ala Ala Lys Glu Val Asn Lys Lys Gln Val Cys Tyr Lys His
            610                 615                 620

Asn Phe Asn Ala Ser Ser Val Ser Trp Cys Ser Lys Thr Val Asp Val
625                 630                 635                 640

Cys Cys His Phe Thr Asn Ala Ala Asn Asn Ser Val Trp Ser Pro Ser
            645                 650                 655

Met Lys Leu Asn Leu Val Pro Gly Glu Asn Ile Thr Cys Gln Asp Pro
            660                 665                 670

Val Ile Gly Val Gly Glu Pro Gly Lys Val Ile Gln Lys Leu Cys Arg
            675                 680                 685

Phe Ser Asn Val Pro Ser Ser Pro Glu Ser Pro Ile Gly Gly Thr Ile
            690                 695                 700

Thr Tyr Lys Cys Val Gly Ser Gln Trp Glu Glu Lys Arg Asn Asp Cys
705                 710                 715                 720

Ile Ser Ala Pro Ile Asn Ser Leu Leu Gln Met Ala Lys Ala Leu Ile
            725                 730                 735

Lys Ser Pro Ser Gln Asp Glu Met Leu Pro Thr Tyr Leu Lys Asp Leu
            740                 745                 750

Ser Ile Ser Ile Asp Lys Ala Glu His Glu Ile Ser Ser Ser Pro Gly
            755                 760                 765

Ser Leu Gly Ala Ile Ile Asn Ile Leu Asp Leu Leu Ser Thr Val Pro
            770                 775                 780

Thr Gln Val Asn Ser Glu Met Met Thr His Val Leu Ser Thr Val Asn
785                 790                 795                 800

Val Ile Leu Gly Lys Pro Val Leu Asn Thr Trp Lys Val Leu Gln Gln
            805                 810                 815

Gln Trp Thr Asn Gln Ser Ser Gln Leu Leu His Ser Val Glu Arg Phe
            820                 825                 830

Ser Gln Ala Leu Gln Ser Gly Asp Ser Pro Pro Leu Ser Phe Ser Gln
            835                 840                 845

Thr Asn Val Gln Met Ser Ser Met Val Ile Lys Ser His Pro Glu
            850                 855                 860

Thr Tyr Gln Gln Arg Phe Val Phe Pro Tyr Phe Asp Leu Trp Gly Asn
865                 870                 875                 880

Val Val Ile Asp Lys Ser Tyr Leu Glu Asn Leu Gln Ser Asp Ser Ser
            885                 890                 895

Ile Val Thr Met Ala Phe Pro Thr Leu Gln Ala Ile Leu Ala Gln Asp
            900                 905                 910

Ile Gln Glu Asn Asn Phe Ala Glu Ser Leu Val Met Thr Thr Thr Val
            915                 920                 925

Ser His Asn Thr Thr Met Pro Phe Arg Ile Ser Met Thr Phe Lys Asn
            930                 935                 940

Asn Ser Pro Ser Gly Gly Glu Thr Lys Cys Val Phe Trp Asn Phe Arg
945                 950                 955                 960

Leu Ala Asn Asn Thr Gly Gly Trp Asp Ser Ser Gly Cys Tyr Val Glu
            965                 970                 975

Glu Gly Asp Gly Asp Asn Val Thr Cys Ile Cys Asp His Leu Thr Ser
            980                 985                 990
```

```
Phe Ser Ile Leu Met Ser Pro Asp Ser Pro Asp Pro Ser Ser Leu Leu
        995                 1000                1005

Gly Ile Leu Leu Asp Ile Ile Ser Tyr Val Gly Val Gly Phe Ser
    1010                1015                1020

Ile Leu Ser Leu Ala Ala Cys Leu Val Val Glu Ala Val Val Trp
    1025                1030                1035

Lys Ser Val Thr Lys Asn Arg Thr Ser Tyr Met Arg His Thr Cys
    1040                1045                1050

Ile Val Asn Ile Ala Ala Ser Leu Leu Val Ala Asn Thr Trp Phe
    1055                1060                1065

Ile Val Val Ala Ala Ile Gln Asp Asn Arg Tyr Ile Leu Cys Lys
    1070                1075                1080

Thr Ala Cys Val Ala Ala Thr Phe Phe Ile His Phe Phe Tyr Leu
    1085                1090                1095

Ser Val Phe Phe Trp Met Leu Thr Leu Gly Leu Met Leu Phe Tyr
    1100                1105                1110

Arg Leu Val Phe Ile Leu His Glu Thr Ser Arg Ser Thr Gln Lys
    1115                1120                1125

Ala Ile Ala Phe Cys Leu Gly Tyr Gly Cys Pro Leu Ala Ile Ser
    1130                1135                1140

Val Ile Thr Leu Gly Ala Thr Gln Pro Arg Glu Val Tyr Thr Arg
    1145                1150                1155

Lys Asn Val Cys Trp Leu Asn Trp Glu Asp Thr Lys Ala Leu Leu
    1160                1165                1170

Ala Phe Ala Ile Pro Ala Leu Ile Ile Val Val Val Asn Ile Thr
    1175                1180                1185

Ile Thr Ile Val Val Ile Thr Lys Ile Leu Arg Pro Ser Ile Gly
    1190                1195                1200

Asp Lys Pro Cys Lys Gln Glu Lys Ser Ser Leu Phe Gln Ile Ser
    1205                1210                1215

Lys Ser Ile Gly Val Leu Thr Pro Leu Leu Gly Leu Thr Trp Gly
    1220                1225                1230

Phe Gly Leu Thr Thr Val Phe Pro Gly Thr Asn Leu Val Phe His
    1235                1240                1245

Ile Ile Phe Ala Ile Leu Asn Val Phe Gln Gly Leu Phe Ile Leu
    1250                1255                1260

Leu Phe Gly Cys Leu Trp Asp Leu Lys Val Gln Glu Ala Leu Leu
    1265                1270                1275

Asn Lys Phe Ser Leu Ser Arg Trp Ser Ser Gln His Ser Lys Ser
    1280                1285                1290

Thr Ser Leu Gly Ser Ser Thr Pro Val Phe Ser Met Ser Ser Pro
    1295                1300                1305

Ile Ser Arg Arg Phe Asn Asn Leu Phe Gly Lys Thr Gly Thr Tyr
    1310                1315                1320

Asn Val Ser Thr Pro Glu Ala Thr Ser Ser Ser Leu Glu Asn Ser
    1325                1330                1335

Ser Ser Ala Ser Ser Leu Leu Asn
    1340                1345

<210> SEQ ID NO 111
<211> LENGTH: 32
<212> TYPE: DNA
<213> ORGANISM: Artificial
<220> FEATURE:
```

<223> OTHER INFORMATION: primer

<400> SEQUENCE: 111
cgcggatccc ttcaggaaga tgttaccctg aa     32

<210> SEQ ID NO 112
<211> LENGTH: 32
<212> TYPE: DNA
<213> ORGANISM: Artificial
<220> FEATURE:
<223> OTHER INFORMATION: primer

<400> SEQUENCE: 112
cgcgaattca acatctattt tcttcttgca ct     32

<210> SEQ ID NO 113
<211> LENGTH: 826
<212> TYPE: PRT
<213> ORGANISM: Mus musculus

<400> SEQUENCE: 113

```
Met Ala Ala Ser Arg Gly Arg Ser Lys Lys Arg Ser Asn Leu Glu Leu
1               5                   10                  15

Ser Pro Asp Asn Leu Pro Leu Arg Ser Ser Gly Arg Gln Ala Lys Lys
            20                  25                  30

Lys Ala Val Glu Ile Pro Asp Glu Asp Glu Asp Gly Ser Ser Glu Lys
        35                  40                  45

Lys Tyr Arg Lys Cys Glu Lys Ala Gly Cys Thr Ala Ala Tyr Pro Val
    50                  55                  60

Cys Phe Ala Ser Ala Ser Glu Arg Cys Ala Lys Asn Gly Tyr Thr Ser
65                  70                  75                  80

Arg Trp Tyr His Leu Ser Cys Gly Glu His Phe Cys Asn Glu Cys Phe
                85                  90                  95

Asp His Tyr Tyr Arg Ser His Lys Asp Gly Tyr Asp Lys Tyr Ser Ala
            100                 105                 110

Trp Lys Arg Val Trp Thr Ser Asn Gly Lys Thr Glu Pro Ser Pro Lys
        115                 120                 125

Ala Phe Met Ala Asp Gln Gln Leu Pro Tyr Trp Val Gln Cys Thr Lys
    130                 135                 140

Pro Glu Cys Gly Lys Trp Arg Gln Leu Thr Lys Glu Ile Gln Leu Thr
145                 150                 155                 160

Pro His Met Ala Arg Thr Tyr Arg Cys Gly Met Lys Pro Asn Thr Ile
                165                 170                 175

Thr Lys Pro Asp Thr Pro Asp His Cys Ser Phe Pro Glu Asp Leu Arg
            180                 185                 190

Val Leu Glu Val Ser Asn His Trp Trp Tyr Pro Met Leu Ile Gln Pro
        195                 200                 205

Pro Leu Leu Lys Asp Ser Val Ala Ala Pro Leu Leu Ser Ala Tyr Tyr
    210                 215                 220

Pro Asp Cys Val Gly Met Ser Pro Ser Cys Thr Ser Thr His Arg Ala
225                 230                 235                 240

Thr Val Thr Ala Ala Thr Thr Thr Thr Gly Ser Ala Ser Pro Gly Glu
                245                 250                 255

Met Glu Pro Ser Lys Ala Ala Pro Ser Ser Leu Val Leu Gly Met Asn
            260                 265                 270

Arg Tyr Phe Gln Pro Phe Tyr Gln Pro Asn Glu Cys Gly Lys Ala Leu
        275                 280                 285
```

-continued

```
Cys Val Arg Pro Asp Val Met Glu Leu Asp Glu Leu Tyr Glu Phe Pro
            290                 295                 300

Glu Tyr Ser Arg Asp Pro Thr Met Tyr Leu Ala Leu Arg Asn Leu Ile
305                 310                 315                 320

Leu Ala Leu Trp Tyr Thr Asn Cys Lys Glu Ala Leu Thr Pro Gln Lys
                325                 330                 335

Cys Ile Pro His Ile Ile Val Arg Gly Leu Val Arg Ile Arg Cys Val
                340                 345                 350

Gln Glu Val Glu Arg Ile Leu Tyr Phe Met Thr Arg Lys Gly Leu Ile
            355                 360                 365

Asn Thr Gly Val Leu Thr Val Ala Ala Gly Gln His Leu Leu Pro Lys
        370                 375                 380

His Tyr His Asn Lys Ser Val Leu Val Val Gly Ala Gly Pro Ala Gly
385                 390                 395                 400

Leu Ala Ala Ala Arg Gln Leu His Asn Phe Gly Met Lys Val Thr Val
                405                 410                 415

Leu Glu Ala Lys Asp Arg Ile Gly Gly Arg Val Trp Asp Asp Lys Ser
                420                 425                 430

Phe Lys Gly Val Val Gly Arg Gly Pro Gln Ile Val Asn Gly Cys
                435                 440                 445

Ile Asn Asn Pro Val Ala Leu Met Cys Glu Gln Leu Gly Ile Ser Met
450                 455                 460

Arg Lys Leu Gly Glu Arg Cys Asp Leu Ile Gln Glu Gly Gly Arg Ile
465                 470                 475                 480

Thr Asp Pro Thr Val Asp Lys Arg Met Asp Phe His Phe Asn Ala Leu
                485                 490                 495

Leu Asp Val Val Ser Glu Trp Arg Lys Asp Lys Thr Leu Leu Gln Asp
                500                 505                 510

Val Pro Leu Gly Glu Lys Ile Glu Glu Ile Tyr Arg Ala Phe Val Lys
                515                 520                 525

Glu Ser Gly Ile Gln Phe Ser Glu Leu Glu Gly Gln Val Leu Gln Phe
            530                 535                 540

His Leu Ser Asn Leu Glu Tyr Ala Cys Gly Ser Ser Leu His Gln Val
545                 550                 555                 560

Ser Ala Arg Ser Trp Asp His Asn Glu Phe Phe Ala Gln Phe Ala Gly
                565                 570                 575

Asp His Thr Leu Leu Thr Pro Gly Tyr Ser Thr Ile Ile Glu Lys Leu
                580                 585                 590

Ala Glu Gly Leu Asp Ile Arg Leu Lys Ser Pro Val Gln Ser Ile Asp
            595                 600                 605

Tyr Thr Gly Asp Glu Val Gln Val Thr Thr Asp Gly Met Gly His
            610                 615                 620

Ser Ala Gln Lys Val Leu Val Thr Val Pro Leu Ala Ile Leu Gln Arg
625                 630                 635                 640

Gly Ala Ile Gln Phe Asn Pro Pro Leu Ser Glu Lys Lys Met Lys Ala
                645                 650                 655

Ile Asn Ser Leu Gly Ala Gly Ile Ile Glu Lys Ile Ala Leu Gln Phe
                660                 665                 670

Pro Tyr Arg Phe Trp Asp Ser Lys Val Gln Gly Ala Asp Phe Phe Gly
            675                 680                 685

His Val Pro Pro Ser Ala Ser Gln Arg Gly Leu Phe Ala Val Phe Tyr
            690                 695                 700
```

```
Asp Met Asp Ser Gln Gln Ser Val Leu Met Ser Val Ile Thr Gly Glu
705                 710                 715                 720

Ala Val Ala Ser Leu Arg Thr Met Asp Asp Lys Gln Val Leu Gln Gln
                725                 730                 735

Cys Met Gly Ile Leu Arg Glu Leu Phe Lys Glu Gln Glu Ile Pro Glu
            740                 745                 750

Pro Thr Lys Tyr Phe Val Thr Arg Trp Ser Thr Glu Pro Trp Ile Gln
        755                 760                 765

Met Ala Tyr Ser Phe Val Lys Thr Phe Gly Ser Gly Glu Ala Tyr Asp
    770                 775                 780

Ile Ile Ala Glu Glu Ile Gln Gly Thr Val Phe Phe Ala Gly Glu Ala
785                 790                 795                 800

Thr Asn Arg His Phe Pro Gln Thr Val Thr Gly Ala Tyr Leu Ser Gly
                805                 810                 815

Val Arg Glu Ala Ser Lys Ile Ala Ala Phe
            820                 825

<210> SEQ ID NO 114
<211> LENGTH: 10
<212> TYPE: PRT
<213> ORGANISM: Artificial
<220> FEATURE:
<223> OTHER INFORMATION: signature peptide

<400> SEQUENCE: 114

Lys Lys Tyr Arg Lys Cys Glu Lys Ala Gly
1               5                   10

<210> SEQ ID NO 115
<211> LENGTH: 10
<212> TYPE: PRT
<213> ORGANISM: Artificial
<220> FEATURE:
<223> OTHER INFORMATION: signature peptide

<400> SEQUENCE: 115

Ala Ala Ser Arg Gly Arg Ser Lys Lys Arg
1               5                   10

<210> SEQ ID NO 116
<211> LENGTH: 10
<212> TYPE: PRT
<213> ORGANISM: Artificial
<220> FEATURE:
<223> OTHER INFORMATION: signature peptide

<400> SEQUENCE: 116

Arg Ser Ser Gly Arg Gln Ala Lys Lys Lys
1               5                   10

<210> SEQ ID NO 117
<211> LENGTH: 10
<212> TYPE: PRT
<213> ORGANISM: Artificial
<220> FEATURE:
<223> OTHER INFORMATION: signature peptide

<400> SEQUENCE: 117

Val Arg Gly Leu Val Arg Ile Arg Cys Val
1               5                   10

<210> SEQ ID NO 118
<211> LENGTH: 10
```

<212> TYPE: PRT
<213> ORGANISM: Artificial
<220> FEATURE:
<223> OTHER INFORMATION: signature peptide

<400> SEQUENCE: 118

Lys Tyr Ser Ala Trp Lys Arg Val Trp Thr
1               5                   10

<210> SEQ ID NO 119
<211> LENGTH: 10
<212> TYPE: PRT
<213> ORGANISM: Artificial
<220> FEATURE:
<223> OTHER INFORMATION: signature peptide

<400> SEQUENCE: 119

Arg Ile Leu Tyr Phe Met Thr Arg Lys Gly
1               5                   10

<210> SEQ ID NO 120
<211> LENGTH: 10
<212> TYPE: PRT
<213> ORGANISM: Artificial
<220> FEATURE:
<223> OTHER INFORMATION: signature peptide

<400> SEQUENCE: 120

Met Ala Arg Thr Tyr Arg Cys Gly Met Lys
1               5                   10

<210> SEQ ID NO 121
<211> LENGTH: 100
<212> TYPE: PRT
<213> ORGANISM: Artificial
<220> FEATURE:
<223> OTHER INFORMATION: tandem polypeptide

<400> SEQUENCE: 121

Lys Lys Tyr Arg Lys Cys Glu Lys Ala Gly Gly Gly Gly Ser Ala
1               5                   10                  15

Ala Ser Arg Gly Arg Ser Lys Lys Arg Gly Gly Gly Ser Arg Ser
            20                  25                  30

Ser Gly Arg Gln Ala Lys Lys Lys Gly Gly Gly Gly Ser Val Arg Gly
            35                  40                  45

Leu Val Arg Ile Arg Cys Val Gly Gly Gly Ser Lys Tyr Ser Ala
            50                  55                  60

Trp Lys Arg Val Trp Thr Gly Gly Gly Gly Ser Arg Ile Leu Tyr Phe
65                  70                  75                  80

Met Thr Arg Lys Gly Gly Gly Gly Ser Met Ala Arg Thr Tyr Arg
                85                  90                  95

Cys Gly Met Lys
                100

<210> SEQ ID NO 122
<211> LENGTH: 322
<212> TYPE: DNA
<213> ORGANISM: Artificial
<220> FEATURE:
<223> OTHER INFORMATION: encoding seqence

<400> SEQUENCE: 122
gacacggatc caagaaatac cgtaaatgcg agaaagcagg aggtggcggc ggaagcgcgg      60

```
cttcccgtgg ccgttcaaaa aaacgtggcg gtggagggtc ccggagcagc ggccgtcagg    120
cgaaaaagaa gggtggtggg ggatctgtgc gtggcctggt gcgtattcgt tgcgttgggg    180
ggggtggatc aaaatactct gcgtggaaac gtgtgtggac cggcggaggc ggcagtcgta    240
tcctgtattt catgacccgt aaaggaggag ggggaggctc gatggcgcgt acctatcgtt    300
gtgggatgaa agaattcgtg tc                                             322
```

```
<210> SEQ ID NO 123
<211> LENGTH: 41
<212> TYPE: DNA
<213> ORGANISM: Artificial
<220> FEATURE:
<223> OTHER INFORMATION: primer

<400> SEQUENCE: 123
gacacggatc aagaaatac cgtaaatgcg agaaagcagg a                         41
```

```
<210> SEQ ID NO 124
<211> LENGTH: 40
<212> TYPE: DNA
<213> ORGANISM: Artificial
<220> FEATURE:
<223> OTHER INFORMATION: primer

<400> SEQUENCE: 124
gccgcgcttc cgccgccacc tcctgctttc tcgcatttac                          40
```

```
<210> SEQ ID NO 125
<211> LENGTH: 40
<212> TYPE: DNA
<213> ORGANISM: Artificial
<220> FEATURE:
<223> OTHER INFORMATION: primer

<400> SEQUENCE: 125
gcggaagcgc ggcttcccgt ggccgttcaa aaaaacgtgg                          40
```

```
<210> SEQ ID NO 126
<211> LENGTH: 40
<212> TYPE: DNA
<213> ORGANISM: Artificial
<220> FEATURE:
<223> OTHER INFORMATION: primer

<400> SEQUENCE: 126
ctgctccggg accctccacc gccacgtttt tttgaacggc                          40
```

```
<210> SEQ ID NO 127
<211> LENGTH: 40
<212> TYPE: DNA
<213> ORGANISM: Artificial
<220> FEATURE:
<223> OTHER INFORMATION: primer

<400> SEQUENCE: 127
agggtcccgg agcagcggcc gtcaggcgaa aaagaagggt                          40
```

```
<210> SEQ ID NO 128
<211> LENGTH: 40
<212> TYPE: DNA
<213> ORGANISM: Artificial
<220> FEATURE:
<223> OTHER INFORMATION: primer

<400> SEQUENCE: 128
```
gccacgcaca gatcccccac caccctttctt tttcgcctga            40

<210> SEQ ID NO 129
<211> LENGTH: 40
<212> TYPE: DNA
<213> ORGANISM: Artificial
<220> FEATURE:
<223> OTHER INFORMATION: primer

<400> SEQUENCE: 129
gggatctgtg cgtggcctgg tgcgtattcg ttgcgttggg            40

<210> SEQ ID NO 130
<211> LENGTH: 40
<212> TYPE: DNA
<213> ORGANISM: Artificial
<220> FEATURE:
<223> OTHER INFORMATION: primer

<400> SEQUENCE: 130
cagagtattt tgatccaccc ccccaacgc aacgaatacg            40

<210> SEQ ID NO 131
<211> LENGTH: 40
<212> TYPE: DNA
<213> ORGANISM: Artificial
<220> FEATURE:
<223> OTHER INFORMATION: primer

<400> SEQUENCE: 131
ggggtggatc aaaatactct gcgtggaaac gtgtgtggac            40

<210> SEQ ID NO 132
<211> LENGTH: 40
<212> TYPE: DNA
<213> ORGANISM: Artificial
<220> FEATURE:
<223> OTHER INFORMATION: primer

<400> SEQUENCE: 132
gatacgactg ccgcctccgc cggtccacac acgtttccac            40

<210> SEQ ID NO 133
<211> LENGTH: 40
<212> TYPE: DNA
<213> ORGANISM: Artificial
<220> FEATURE:
<223> OTHER INFORMATION: primer

<400> SEQUENCE: 133
gaggcggcag tcgtatcctg tatttcatga cccgtaaagg            40

<210> SEQ ID NO 134
<211> LENGTH: 40
<212> TYPE: DNA
<213> ORGANISM: Artificial
<220> FEATURE:
<223> OTHER INFORMATION: primer

<400> SEQUENCE: 134
atcgagcctc cccctcctcc tttacgggtc atgaaataca            40

<210> SEQ ID NO 135
<211> LENGTH: 40
<212> TYPE: DNA

<213> ORGANISM: Artificial
<220> FEATURE:
<223> OTHER INFORMATION: primer

<400> SEQUENCE: 135
gagggggagg ctcgatggcg cgtacctatc gttgtgggat           40

<210> SEQ ID NO 136
<211> LENGTH: 35
<212> TYPE: DNA
<213> ORGANISM: Artificial
<220> FEATURE:
<223> OTHER INFORMATION: primer

<400> SEQUENCE: 136
gacacgaatt ctttcatccc acaacgatag gtacg           35

<210> SEQ ID NO 137
<211> LENGTH: 100
<212> TYPE: PRT
<213> ORGANISM: Artificial
<220> FEATURE:
<223> OTHER INFORMATION: antigen

<400> SEQUENCE: 137

Gly Lys Leu Leu Gly Gln Gly Ala Phe Gly Gly Gly Gly Ser Pro
1               5                   10                  15
Asp Ser Pro Glu Thr Ser Lys Glu Val Gly Gly Gly Gly Ser Gly Gly
                20                  25                  30
Ser Val Lys Asp Gln Leu Lys Ala Gly Gly Gly Ser Arg Lys Tyr
            35                  40                  45
Thr Arg Gln Ile Leu Glu Gly Gly Gly Gly Ser Val Lys Leu Gly
        50                  55                  60
Asp Phe Gly Ala Ser Lys Gly Gly Gly Ser Met Asp Glu Gln Glu
65                  70                  75                  80
Ala Leu Asn Ser Ile Gly Gly Gly Gly Ser Leu Thr His His Phe Ala
                85                  90                  95
Gln Leu Met Tyr
            100

<210> SEQ ID NO 138
<211> LENGTH: 100
<212> TYPE: PRT
<213> ORGANISM: Artificial
<220> FEATURE:
<223> OTHER INFORMATION: antigen

<400> SEQUENCE: 138

Ala Gln Thr Gln Gly Thr Arg Arg Lys Val Gly Gly Gly Gly Ser Ser
1               5                   10                  15
Val Ala Ser Ala Val Lys Leu Asn Lys Gly Gly Gly Gly Ser Arg Asp
                20                  25                  30
Gly Ile Asp Asp Glu Ser Tyr Glu Gly Gly Gly Gly Ser Pro Asp Phe
            35                  40                  45
Lys Leu His Ile Ser Pro Ser Gly Gly Gly Ser Gly Gly Arg Lys
        50                  55                  60
Asn Ser Ser Asn Phe Lys Gly Gly Gly Ser Lys Gly Val Lys Glu
65                  70                  75                  80
Glu Val Lys Leu Ala Gly Gly Gly Gly Ser Lys Pro Val Met Ser Lys
                85                  90                  95

Val Met Glu Met
            100

<210> SEQ ID NO 139
<211> LENGTH: 100
<212> TYPE: PRT
<213> ORGANISM: Artificial
<220> FEATURE:
<223> OTHER INFORMATION: antigen

<400> SEQUENCE: 139

Ala Ala Asp Gly Gly Glu Glu Ala Gly Gly Gly Ser Gln Asp
1               5                   10                  15

Arg Val Ala Arg Ala Ala Gly Arg Glu Gly Gly Gly Ser Met Lys
                20                  25                  30

Phe Gly Lys Ser Leu Ser Ser Gln Gly Gly Gly Ser Lys Asp Leu
                35                  40                  45

Lys Lys Arg Leu Lys Leu Ile Gly Gly Gly Ser Glu Glu Arg Gln
            50                  55                  60

Ala Lys Arg Ala Arg Val Gly Gly Gly Ser Gly Asp Ser Ser Pro
65                  70                  75                  80

Glu Glu Gln Gln Glu Gly Gly Gly Ser Lys Ile Pro Val Ile Glu
                85                  90                  95

Gln Ala Ala Lys
            100

<210> SEQ ID NO 140
<211> LENGTH: 100
<212> TYPE: PRT
<213> ORGANISM: Artificial
<220> FEATURE:
<223> OTHER INFORMATION: antigen

<400> SEQUENCE: 140

Gln Lys Met Glu Val Gln Gly Asn Leu Phe Gly Gly Gly Ser Lys
1               5                   10                  15

Lys Lys His Ala Asn Asp Leu Gln His Gly Gly Gly Ser Glu Thr
                20                  25                  30

Tyr Asp Pro Glu Gly Lys Phe Leu Gly Gly Gly Ser Pro Lys Arg
                35                  40                  45

Asp Asp Asp Asn Ala Lys Gly Gly Gly Gly Ser Glu Lys Lys His
            50                  55                  60

Ser Ser Glu Thr Pro Gln Gly Gly Gly Ser Glu Lys Arg Asn Tyr
65                  70                  75                  80

Thr Asn Leu Lys Lys Gly Gly Gly Gly Ser Glu Arg Asn Glu Pro Tyr
                85                  90                  95

Asn Ile Val Asp
            100

<210> SEQ ID NO 141
<211> LENGTH: 100
<212> TYPE: PRT
<213> ORGANISM: Artificial
<220> FEATURE:
<223> OTHER INFORMATION: antigen

<400> SEQUENCE: 141

Asp Gly Val Tyr Ser Lys Lys Lys His Ala Gly Gly Gly Ser Arg
1               5                   10                  15

Ala Lys Lys Asn Asn Val Glu Lys Ile Gly Gly Gly Ser Lys Asn

```
                    20                  25                  30

Phe Met Glu Glu Lys Asp Lys Gln Gly Gly Gly Gly Ser Pro Lys Pro
                35                  40                  45

Asp Asp Ala Lys Ala Lys Gly Gly Gly Gly Gly Ser Asp Ala Gln Ile
        50                  55                  60

Lys Lys Gln Glu Asn Lys Gly Gly Gly Gly Ser Lys Lys Lys Ile Thr
65                  70                  75                  80

Asn His Ser Asn Arg Gly Gly Gly Gly Ser Glu Lys Arg Asn Tyr Thr
                85                  90                  95

Asn Leu Lys Lys
            100

<210> SEQ ID NO 142
<211> LENGTH: 100
<212> TYPE: PRT
<213> ORGANISM: Artificial
<220> FEATURE:
<223> OTHER INFORMATION: antigen

<400> SEQUENCE: 142

Lys Thr Asn Lys Thr Phe Lys Ile Lys Lys Gly Gly Gly Gly Ser Asn
1               5                   10                  15

Lys Lys Lys His Glu Asn Asp Leu Arg Gly Gly Gly Gly Ser Glu Thr
                20                  25                  30

Tyr Asp Pro Lys Gly Glu Phe Leu Gly Gly Gly Gly Ser Pro Gly Phe
            35                  40                  45

Leu Tyr Asn Glu Gln Asp Lys Gly Gly Gly Gly Ser Glu Lys Tyr Lys
        50                  55                  60

Pro Leu Ile Glu Gln Val Gly Gly Gly Ser Lys Thr Pro Glu Asn
65                  70                  75                  80

Ile Asn Ala Val Lys Gly Gly Gly Gly Ser Glu Lys Arg Asn Tyr Thr
                85                  90                  95

Asn Leu Lys Lys
            100

<210> SEQ ID NO 143
<211> LENGTH: 100
<212> TYPE: PRT
<213> ORGANISM: Artificial
<220> FEATURE:
<223> OTHER INFORMATION: antigen

<400> SEQUENCE: 143

Asn Lys Lys Lys His Glu Asn Asp Leu Lys Gly Gly Gly Gly Ser Glu
1               5                   10                  15

Thr Tyr Asp Pro Lys Gly Glu Phe Leu Gly Gly Gly Gly Ser Asp Thr
                20                  25                  30

Lys Asn Gln Gly Leu Lys Val Asp Gly Gly Gly Gly Ser Gly Glu Met
            35                  40                  45

Gly Leu Asp Phe Asp Arg Leu Gly Gly Gly Gly Ser Glu Lys Tyr Lys
        50                  55                  60

Pro Leu Ile Glu Gln Val Gly Gly Gly Ser Glu Lys Arg Asn Tyr
65                  70                  75                  80

Thr Asn Leu Lys Lys Gly Gly Gly Gly Ser Asp Arg Asn Glu Pro Tyr
                85                  90                  95

Asn Ile Val Asp
            100
```

<210> SEQ ID NO 144
<211> LENGTH: 69
<212> TYPE: PRT
<213> ORGANISM: Artificial
<220> FEATURE:
<223> OTHER INFORMATION: antigen

<400> SEQUENCE: 144

Lys Lys Tyr Arg Lys Cys Glu Lys Ala Gly Ala Gln Thr Gln Gly Thr
1               5                   10                  15

Arg Arg Lys Val Ala Ala Asp Gly Gly Glu Glu Ala Gln Lys Met
            20                  25                  30

Glu Val Gln Gly Asn Leu Phe Asp Gly Val Tyr Ser Lys Lys His
        35                  40                  45

Ala Lys Thr Asn Lys Thr Phe Lys Ile Lys Asn Lys Lys His
    50                  55                  60

Glu Asn Asp Leu Lys
65

<210> SEQ ID NO 145
<211> LENGTH: 71
<212> TYPE: PRT
<213> ORGANISM: Artificial
<220> FEATURE:
<223> OTHER INFORMATION: antigen

<400> SEQUENCE: 145

Ala Ala Ser Arg Gly Arg Ser Lys Arg Ser Val Ala Ser Ala Val
1               5                   10                  15

Lys Leu Asn Lys Gln Asp Arg Val Ala Arg Ala Gly Arg Glu Lys
            20                  25                  30

Lys Lys His Ala Asn Asp Leu Gln His Arg Ala Lys Lys Asn Asn Val
        35                  40                  45

Glu Lys Ile Asn Lys Lys His Gly Asn Asp Leu Arg Glu Thr Tyr
    50                  55                  60

Asp Pro Lys Gly Glu Phe Leu
65                  70

<210> SEQ ID NO 146
<211> LENGTH: 70
<212> TYPE: PRT
<213> ORGANISM: Artificial
<220> FEATURE:
<223> OTHER INFORMATION: antigen

<400> SEQUENCE: 146

Arg Ser Ser Gly Arg Gln Ala Lys Lys Arg Asp Gly Ile Asp Asp
1               5                   10                  15

Glu Ser Tyr Glu Met Lys Phe Gly Lys Ser Leu Ser Ser Gln Glu Thr
            20                  25                  30

Tyr Asp Pro Glu Gly Lys Phe Leu Lys Asn Phe Met Glu Glu Lys Asp
        35                  40                  45

Lys Gln Glu Thr Tyr Asp Pro Lys Gly Glu Phe Leu Asp Thr Lys Asn
    50                  55                  60

Gln Gly Leu Lys Val Asp
65                  70

<210> SEQ ID NO 147
<211> LENGTH: 69
<212> TYPE: PRT

<213> ORGANISM: Artificial
<220> FEATURE:
<223> OTHER INFORMATION: antigen

<400> SEQUENCE: 147

```
Val Arg Gly Leu Val Arg Ile Arg Cys Val Pro Asp Phe Lys Leu His
1               5                   10                  15

Ile Ser Pro Ser Lys Asp Leu Lys Lys Arg Leu Lys Leu Ile Pro Lys
                20                  25                  30

Arg Asp Asp Asp Asn Ala Lys Gly Pro Lys Pro Asp Asp Ala Lys Ala
            35                  40                  45

Lys Gly Pro Gly Phe Leu Tyr Asn Glu Gln Asp Lys Gly Glu Met Gly
        50                  55                  60

Leu Asp Phe Asp Arg
65
```

<210> SEQ ID NO 148
<211> LENGTH: 70
<212> TYPE: PRT
<213> ORGANISM: Artificial
<220> FEATURE:
<223> OTHER INFORMATION: antigen

<400> SEQUENCE: 148

```
Lys Tyr Ser Ala Trp Lys Arg Val Trp Thr Gly Gly Arg Lys Asn Ser
1               5                   10                  15

Ser Asn Phe Lys Glu Glu Arg Gln Ala Lys Arg Ala Arg Val Glu Lys
                20                  25                  30

Lys His Ser Ser Glu Thr Pro Gln Asp Ala Gln Ile Lys Lys Gln Glu
            35                  40                  45

Asn Lys Glu Lys Tyr Lys Pro Leu Ile Glu Gln Val Glu Lys Tyr Lys
        50                  55                  60

Pro Leu Ile Glu Gln Val
65                  70
```

<210> SEQ ID NO 149
<211> LENGTH: 70
<212> TYPE: PRT
<213> ORGANISM: Artificial
<220> FEATURE:
<223> OTHER INFORMATION: antigen

<400> SEQUENCE: 149

```
Arg Ile Leu Tyr Phe Met Thr Arg Lys Gly Lys Gly Val Lys Glu Glu
1               5                   10                  15

Val Lys Leu Ala Gly Asp Ser Ser Pro Glu Glu Gln Gln Glu Glu Lys
                20                  25                  30

Arg Asn Tyr Thr Asn Leu Lys Lys Lys Lys Ile Thr Asn His Ser
            35                  40                  45

Asn Arg Lys Thr Pro Glu Asn Ile Asn Ala Val Lys Glu Lys Arg Asn
        50                  55                  60

Tyr Thr Asn Leu Lys Lys
65                  70
```

<210> SEQ ID NO 150
<211> LENGTH: 70
<212> TYPE: PRT
<213> ORGANISM: Artificial
<220> FEATURE:
<223> OTHER INFORMATION: antigen

```
<400> SEQUENCE: 150

Met Ala Arg Thr Tyr Arg Cys Gly Met Lys Lys Pro Val Met Ser Lys
1               5                   10                  15

Val Met Glu Met Lys Ile Pro Val Ile Glu Gln Ala Ala Lys Glu Arg
            20                  25                  30

Asn Glu Pro Tyr Asn Ile Val Asp Glu Lys Arg Asn Tyr Thr Asn Leu
        35                  40                  45

Lys Lys Glu Lys Arg Asn Tyr Thr Asn Leu Lys Lys Asp Arg Asn Glu
    50                  55                  60

Pro Tyr Asn Ile Val Asp
65                  70

<210> SEQ ID NO 151
<211> LENGTH: 10
<212> TYPE: PRT
<213> ORGANISM: Artificial
<220> FEATURE:
<223> OTHER INFORMATION: epitope

<400> SEQUENCE: 151

Gly Lys Leu Leu Gly Gln Gly Ala Phe Gly
1               5                   10

<210> SEQ ID NO 152
<211> LENGTH: 10
<212> TYPE: PRT
<213> ORGANISM: Artificial
<220> FEATURE:
<223> OTHER INFORMATION: epitope

<400> SEQUENCE: 152

Pro Asp Ser Pro Glu Thr Ser Lys Glu Val
1               5                   10

<210> SEQ ID NO 153
<211> LENGTH: 10
<212> TYPE: PRT
<213> ORGANISM: Artificial
<220> FEATURE:
<223> OTHER INFORMATION: epitope

<400> SEQUENCE: 153

Gly Gly Ser Val Lys Asp Gln Leu Lys Ala
1               5                   10

<210> SEQ ID NO 154
<211> LENGTH: 10
<212> TYPE: PRT
<213> ORGANISM: Artificial
<220> FEATURE:
<223> OTHER INFORMATION: epitope

<400> SEQUENCE: 154

Arg Lys Tyr Thr Arg Gln Ile Leu Glu Gly
1               5                   10

<210> SEQ ID NO 155
<211> LENGTH: 10
<212> TYPE: PRT
<213> ORGANISM: Artificial
<220> FEATURE:
<223> OTHER INFORMATION: epitope

<400> SEQUENCE: 155
```

Val Lys Leu Gly Asp Phe Gly Ala Ser Lys
1               5                   10

<210> SEQ ID NO 156
<211> LENGTH: 10
<212> TYPE: PRT
<213> ORGANISM: Artificial
<220> FEATURE:
<223> OTHER INFORMATION: epitope

<400> SEQUENCE: 156

Met Asp Glu Gln Glu Ala Leu Asn Ser Ile
1               5                   10

<210> SEQ ID NO 157
<211> LENGTH: 10
<212> TYPE: PRT
<213> ORGANISM: Artificial
<220> FEATURE:
<223> OTHER INFORMATION: epitope

<400> SEQUENCE: 157

Leu Thr His His Phe Ala Gln Leu Met Tyr
1               5                   10

<210> SEQ ID NO 158
<211> LENGTH: 5
<212> TYPE: PRT
<213> ORGANISM: Artificial
<220> FEATURE:
<223> OTHER INFORMATION: linker

<400> SEQUENCE: 158

Gly Gly Gly Gly Ser
1               5

<210> SEQ ID NO 159
<211> LENGTH: 61
<212> TYPE: DNA
<213> ORGANISM: Artificial
<220> FEATURE:
<223> OTHER INFORMATION: multiple cloning site

<400> SEQUENCE: 159
gtggcggatc ctatcagatc tatcgggtac cgtatcgcgg ccgcttccat atggaattcg      60
g                                                                    61

<210> SEQ ID NO 160
<211> LENGTH: 61
<212> TYPE: DNA
<213> ORGANISM: Artificial
<220> FEATURE:
<223> OTHER INFORMATION: multiple cloning site

<400> SEQUENCE: 160
ccgaattcca tatggaagcg gccgcgatac ggtacccgat agatctgata ggatccgcca      60
c                                                                    61

<210> SEQ ID NO 161
<211> LENGTH: 8
<212> TYPE: PRT
<213> ORGANISM: Artificial
<220> FEATURE:
<223> OTHER INFORMATION: Beta-gal

<400> SEQUENCE: 161

```
Met Thr Met Ile Thr Asp Ser Leu
1               5

<210> SEQ ID NO 162
<211> LENGTH: 12
<212> TYPE: PRT
<213> ORGANISM: Artificial
<220> FEATURE:
<223> OTHER INFORMATION: linker

<400> SEQUENCE: 162

Glu Glu Gly Gly Gly Gly Ser Gly Gly Gly Gly Ser
1               5                   10

<210> SEQ ID NO 163
<211> LENGTH: 12
<212> TYPE: PRT
<213> ORGANISM: Artificial
<220> FEATURE:
<223> OTHER INFORMATION: linker

<400> SEQUENCE: 163

Gly Gly Gly Gly Ser Gly Gly Gly Gly Ser Glu Glu
1               5                   10

<210> SEQ ID NO 164
<211> LENGTH: 6
<212> TYPE: PRT
<213> ORGANISM: Artificial
<220> FEATURE:
<223> OTHER INFORMATION: linker

<400> SEQUENCE: 164

His His His His His His
1               5
```